United States Patent
Ghosh

(10) Patent No.: US 10,609,922 B2
(45) Date of Patent: *Apr. 7, 2020

(54) PROTECTION OF PROGENITOR CELLS AND REGULATION OF THEIR DIFFERENTIATION

(71) Applicant: Proteobioactives Pty Ltd, New South Wales (AU)

(72) Inventor: Peter Ghosh, Fairlight (AU)

(73) Assignee: Proteobioactives Pty Ltd, Brookvale, New South Wales (AU)

( * ) Notice: Subject to any disclaimer, the term of this patent is extended or adjusted under 35 U.S.C. 154(b) by 46 days.

This patent is subject to a terminal disclaimer.

(21) Appl. No.: 15/861,182

(22) Filed: Jan. 3, 2018

(65) Prior Publication Data

US 2018/0206480 A1 Jul. 26, 2018

Related U.S. Application Data

(63) Continuation of application No. 15/235,613, filed on Aug. 12, 2016, now Pat. No. 9,888,679, which is a continuation of application No. 12/746,343, filed as application No. PCT/AU2008/001795 on Dec. 4, 2008, now abandoned.

(30) Foreign Application Priority Data

Dec. 4, 2007 (AU) ................. 2007906607

(51) Int. Cl.
| | | |
|---|---|---|
| A01N 1/02 | (2006.01) | |
| C12N 5/077 | (2010.01) | |
| A61K 35/28 | (2015.01) | |
| A61K 31/737 | (2006.01) | |
| C12N 5/0775 | (2010.01) | |
| A61K 35/12 | (2015.01) | |

(52) U.S. Cl.
CPC .......... *A01N 1/0226* (2013.01); *A61K 31/737* (2013.01); *A61K 35/28* (2013.01); *C12N 5/0655* (2013.01); *C12N 5/0663* (2013.01); *A61K 35/12* (2013.01); *C12N 2501/90* (2013.01); *C12N 2506/1346* (2013.01)

(58) Field of Classification Search
None
See application file for complete search history.

(56) References Cited

U.S. PATENT DOCUMENTS

| 5,145,841 A | 9/1992 | Cullis-Hill et al. |
|---|---|---|
| 8,753,391 B2 * | 6/2014 | Lu .............. A61K 38/18 623/13.11 |
| 2003/0069639 A1 | 4/2003 | Sander et al. |

FOREIGN PATENT DOCUMENTS

| WO | WO-97/39104 A1 | 10/1997 |
|---|---|---|
| WO | WO-2004/110475 A1 | 12/2004 |
| WO | WO-2006/032092 A1 | 3/2006 |
| WO | WO-2006/085209 A1 | 8/2006 |
| WO | WO-2012/101544 A1 | 8/2012 |
| WO | WO-2014/089623 A1 | 6/2014 |

OTHER PUBLICATIONS

Alsalameh, et al., "Identification of Mesenchymal Progenitor Cells in Normal and Osteoarthritic Human Articular Cartilage," Arthritis & Rheumatism, vol. 50, No. 5, May 2004, pp. 1522-1532.
Augello et al., "Cell therapy using allogeneic bone marrow mesenchymal stem cells prevents tissue damage in collagen-induced arthritis," Arthritis Rheum, 56(4): 1175-1186 (2007).
Cool et al., "Heparan sulfate regulation of progenitor cell fate," J. Cell Biochem., 99(4):1040-1051 (2006).
English translation of Chinese Office Action dated Aug. 3, 2012.
English Translation of Chinese Office Action dated Dec. 7, 2011 in Chinese Patent Application No. 200880126107.3.
English translation of Chinese Office Action dated Mar. 12, 2012.
Ghosh, "The Pathobiology of Osteoarthritis and the Rationale for the Use of Pentosan Polysulfate for Its Treatment," Seminars in Arthritis and Rheumatism, vol. 28, No. 4, Feb. 1999, pp. 211-267.
Ghosh, P., et al., "Pentosan polysulfate promotes proliferation and chondrogenic differentiation of adult human bone marrow-derived mesenchymal precursor cells" Arthritis Research & Therapy 2010, 12:R28, pp. 1-17.
Goldschlager et al. "Cervical motion preservation using mesenchymal progenitor cells and pentosan polysulfate, a novel chondrogenic agent: preliminary study in an ovine model," Neurosurg Focus 28(6):E4, pp. 1-8 (2010).
Guan et al., "Effects of rapid cooling on articular cartilage," Cryobiology, 52(3): 430-439 (2006).
Ingram, D. et al., "Identification of a novel hierarchy of endothelial progenitor cells using human peripheral and umbilical cord blood" Blood, 2004, 104, pp. 2752-2760.
Kode et al., "Mesenchymal stem cells: immunobiology and role in immunomodulation and tissue regeneration," Cytotherapy, 11(4): 377-391 (2009).
Luyten et al., "Mesenchymal stem cells in osteoarthritis," Curr Opin Rheumatol, 16(5): 599-603 (2004).
Munteanu, S., et al. "Calcium Pentosan Polysulfate Inhibits the Catabolism of Aggrecan in Articular Cartilage Explant Cultures" Arthritis & Rheumatism, 2000, 43(10): pp. 2211-2218.

(Continued)

*Primary Examiner* — David W Berke-Schlessel
(74) *Attorney, Agent, or Firm* — Foley Hoag LLP

(57) ABSTRACT

The present invention relates to the use of polysulfated polysaccharides in combination with progenitor cells to improve the viability of the progenitor cells including improving the cryopreservation of the progenitor cells and provides novel compositions, methods and uses. The present invention also relates to the use of polysulfated polysaccharides to regulate the proliferation and differentiation of progenitor cells.

13 Claims, 39 Drawing Sheets

Specification includes a Sequence Listing.

(56) References Cited

OTHER PUBLICATIONS

Ng et al., "HelinxTM-treated peripheral blood mononuclear cells (PBMC) with anotosalen hydrochloride maintain their biological functions post-cryopreservation," Blood, 98(11):332b (English Abstract).
Oehme et al., "Mesenchymal progenitor cells combined with pentosan polysulfate mediating disc regeneration at the time of microdiscectomy: a preliminary study in an ovine model," *J Neurosurg Spine*, 20(6): 657-669 (2014).
Opolka, A., et al. "Collagen IX is indispensable for timely maturation of cartilage during fracture repair in mice" Matrix Biology, 2007, pp. 85-95, online Oct. 3, 2006.
Pihlajamaa, et al., "Characterization of Recombinant Amino-terminal NC4 Domain of Human Collagen IX," The Journal of Biological Chemistry, 2004, 279(23): 24265-24273.
San Antonio, et al. Dev Biol. 1987; 123:17-24.
Zhang et al., "Low molecular weight heparin on the role of VEGF in rabbits proliferative capacity of MSCs," Sichuan Medical Journal, 27(4):331-333 (English Abstract only).

\* cited by examiner

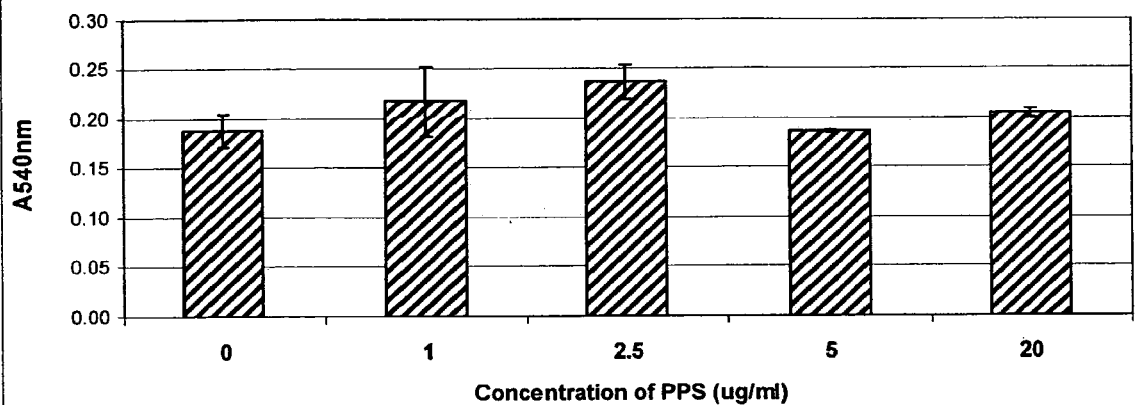
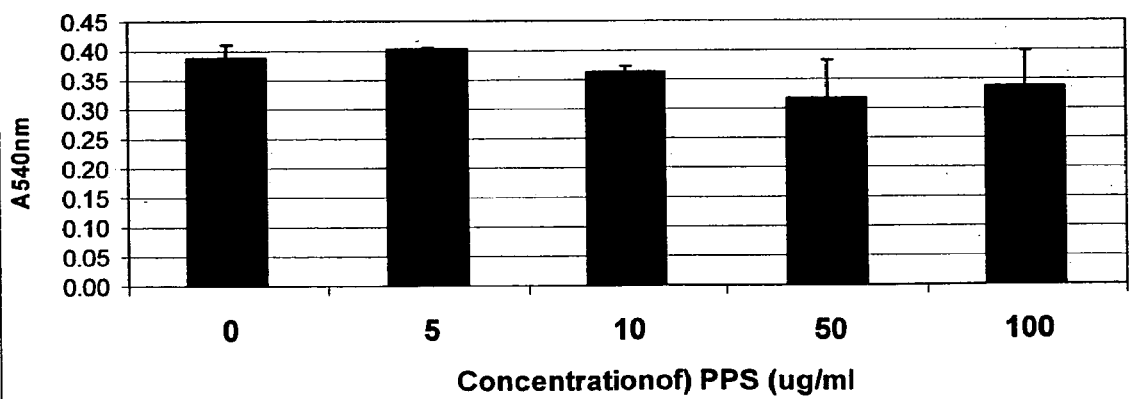
Figure 3

The Effects of Pentosan Polysulfate on Human progenitor cells Apoptosis induced by the addition of a combination of 30ng/ml IL-4 and 30,000U/ml IFN-gamma. After 5 day culture progenitor cell viability was determined by Annexin V staining and analysis by Flow Cytometry

The Effects of Pentosan Polysulfate on Human progenitor cells (M111sP4) Differentiation into bone using osteogenic media culture conditions and the Cresolphthalein Complexone Mineralisation Assay. Data = Means ± SEM

A   In Vitro Mineral Production of M111s P4 +/- PPS (relative to DNA Conc)

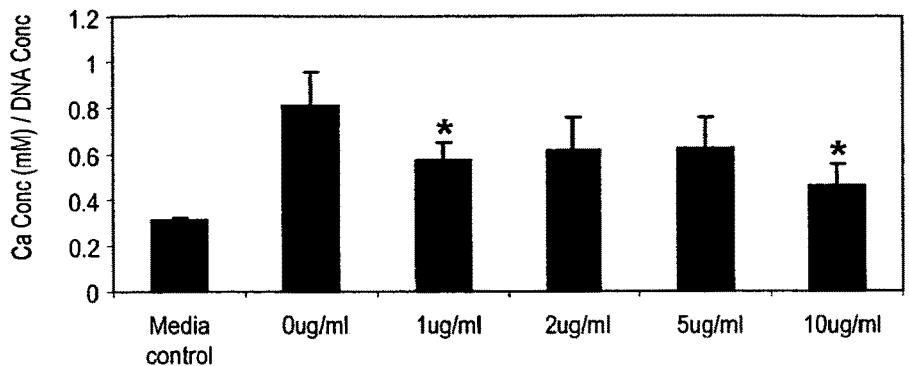

B   In Vitro Mineral Production of M111s P4 +/- PPS - Photomicrographs of Osteogenic Cultures

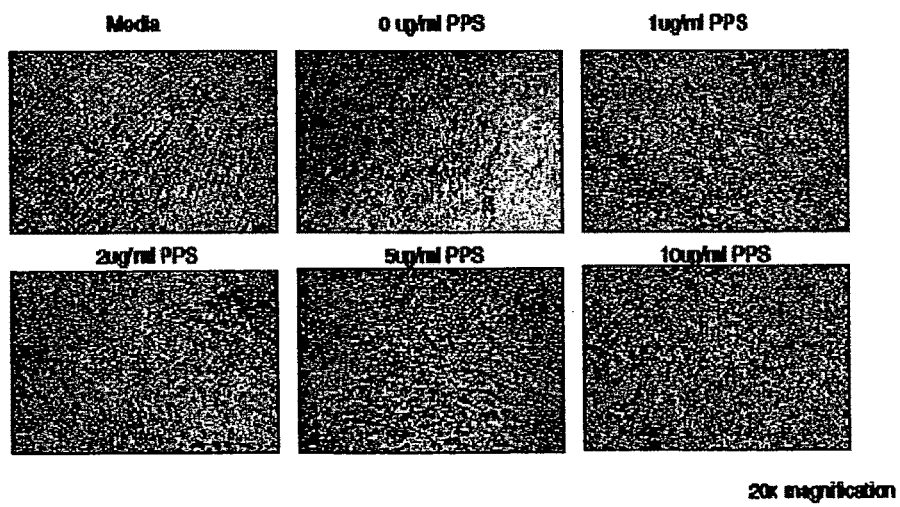

Figure 7

The Effects of Pentosan Polysulfate on Human progenitor cells (M111sP4) Differentiation into Adipocytes using adipogenic media culture conditions and the Oil Red-O dye Assay. Data = Means ± SEM

A In Vitro Adipocyte formation (Oil Red O Staining) of M111 cells P4 - Cultured with PPS - (Relative to DNA)

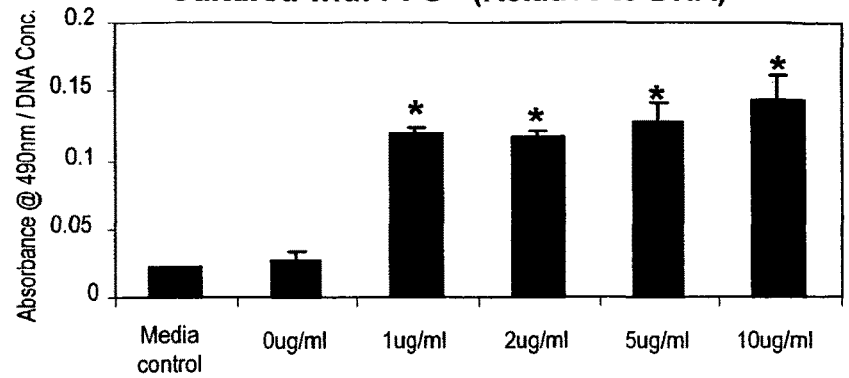

B In Vitro Adipocyte formation (Oil Red O Staining) of M111 cells P4 - Cultured with PPS –Photomicrographs of Adipocyte Cultures

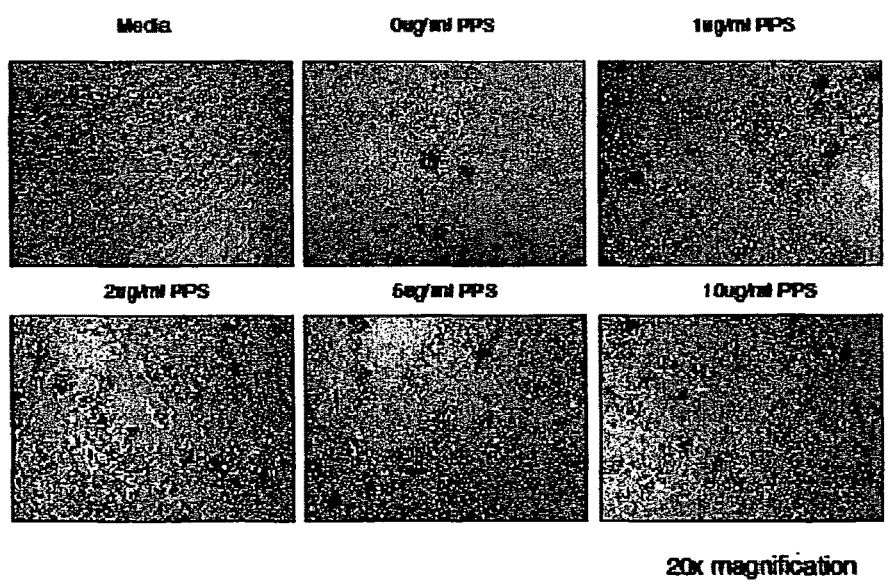

20x magnification

Figure 8

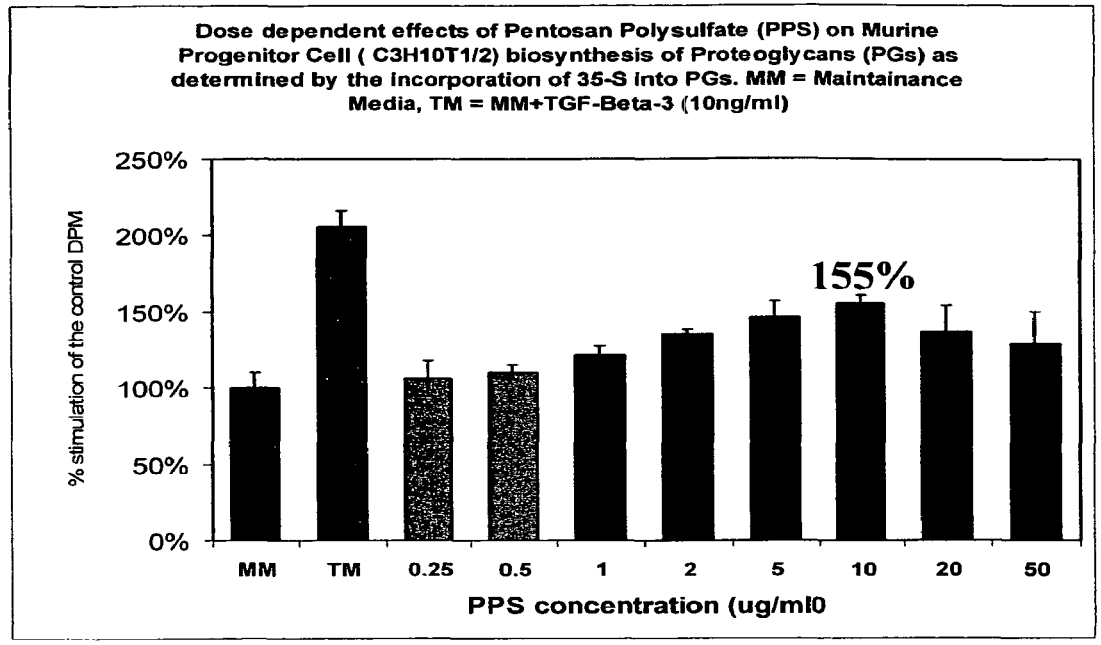
PG SYNTHESIS
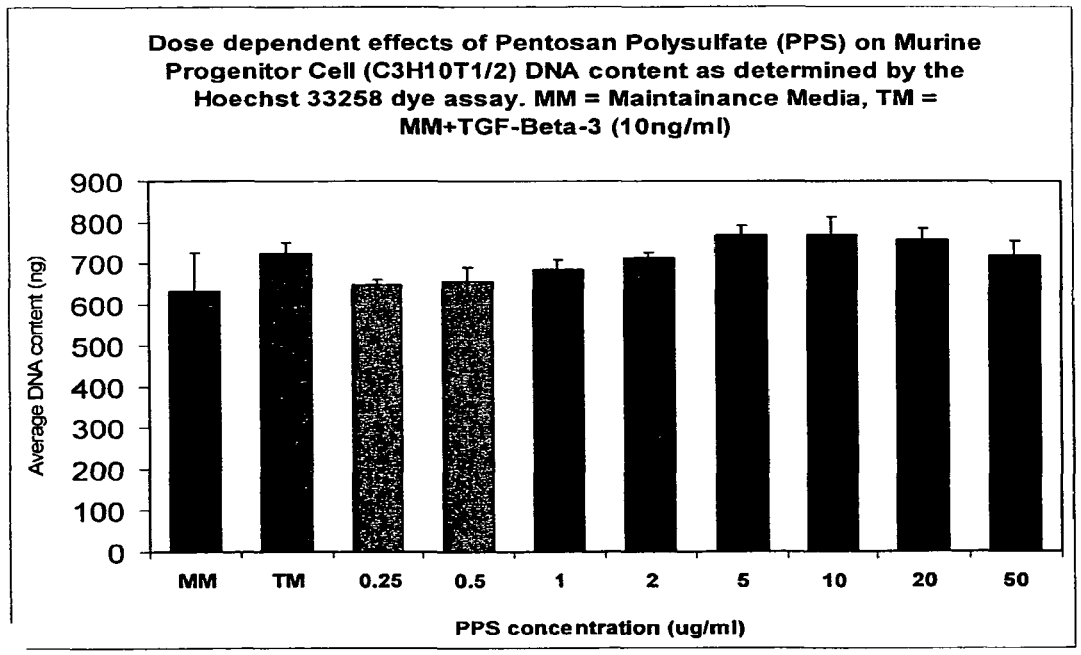
DNA CONTENT (Cell numbers)
Figure 9

Dose dependent effects of Pentosan Polysulfate (PPS) on Murine Progenitor Cell (ATDC5) biosynthesis of Proteoglycans (PGs) in pellet culture + Maintainance Media as determined by the incorporation of 35-S into PGs/ug DNA.

Gene Expression by ATDC5 cells in 6-day pellet culture with treatment of different concentration of PPS in Maintenance Medium (MM)

Dose dependent effects of Heparin on Murine Progenitor Cell (ATDC5) biosynthesis of Proteoglycans (PGs) in pellet culture as determined by the incorporation of 35-S into PGs/ug DNA. MM = in Maintainance Media, DM = in MM+Insulin(10ug/ml)

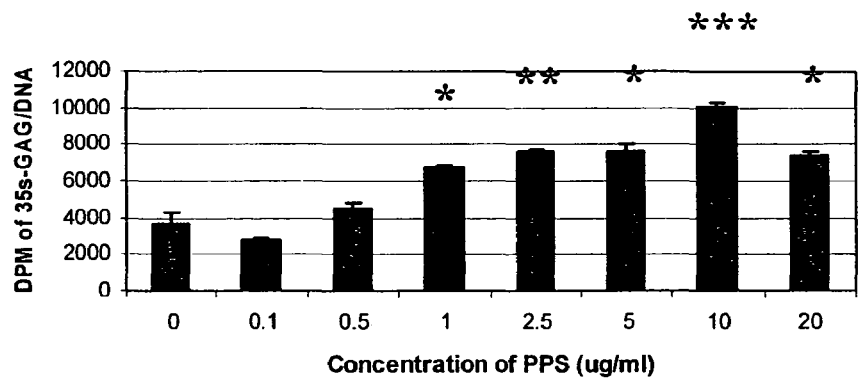
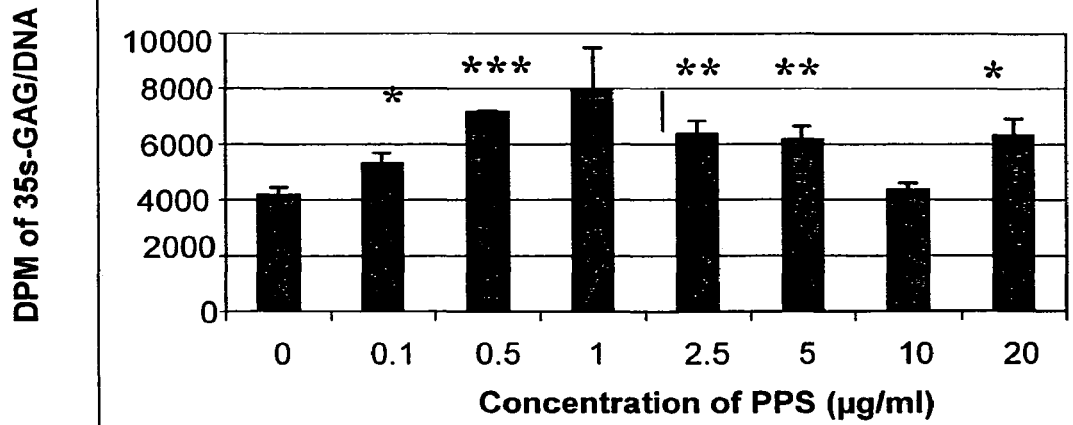
Figure 16

Figure 18
A
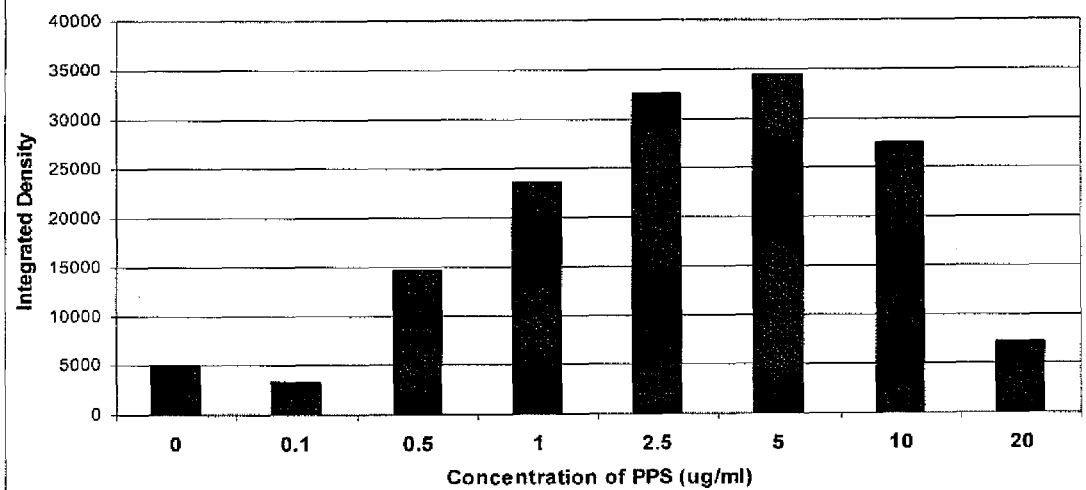
Histoimmunostaining for Type II Collagen produced by micromass cultures of human Progenitor Cells cultured for 10 days in the presence of various concentrations of Pentosan Polysulfate (PPS)
B
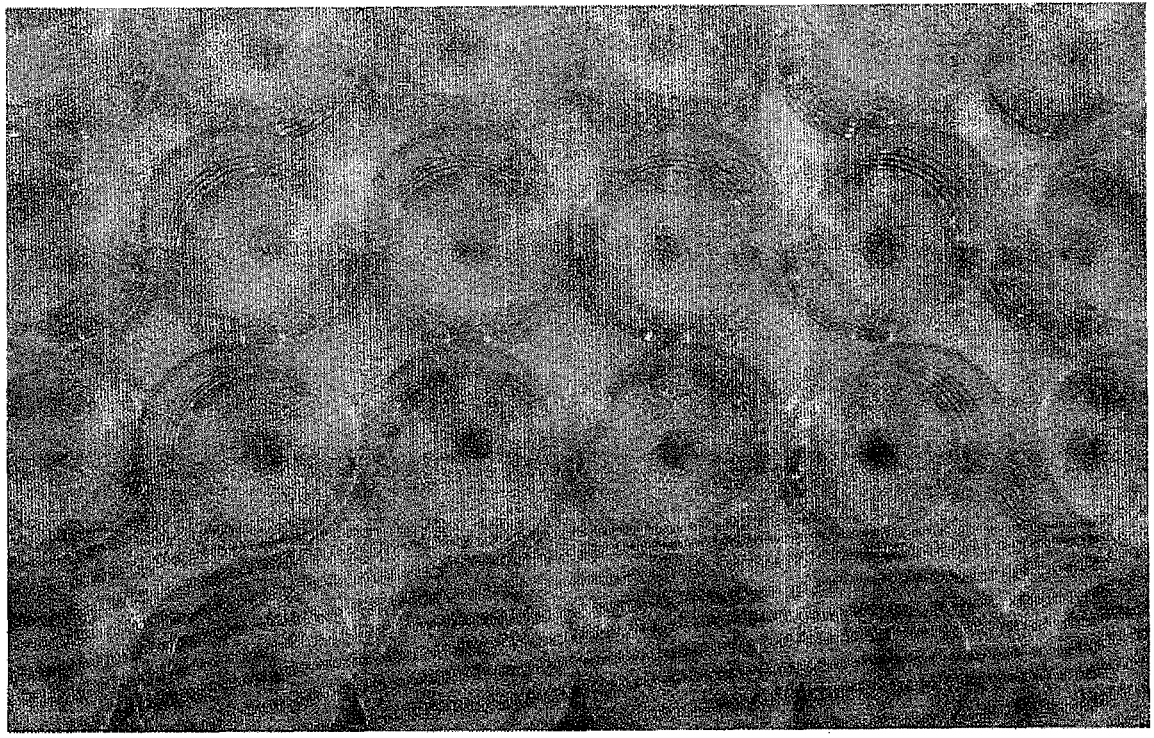

The Effects of Pentosan Polysulfate and Hyaluronic Acid alone and in combination on Normal Human Progenitor Cell Proliferation in monolayer cultures using the WST-1 mitochondral dehydrogenase cleavage assay.

Day 3

The Effects of Pentosan Polysulfate and Hyaluronic Acid alone and in combination on Normal Human Progenitor Cell Proliferation in monolayer cultures using the WST-1 mitochondral dehydrogenase cleavage assay.

Figure 20 (cont)

The Effects of Pentosan Polysulfate and Hyaluronic Acid alone and in combination on Normal Human Progenitor Cell Proliferation in monolayer cultures using the WST-1 mitochondral dehydrogenase cleavage assay.

FOLD INCREASE BETWEEN DAY 3 AND DAY 5

PPS

| | 0 | 0.5 | 1 | 1.25 | 2.5 | 5 | 10 | 25 | 50 | 100 |
|---|---|---|---|---|---|---|---|---|---|---|
| 0 | 1.367027 | 1.548069 | 1.572297 | 1.508635 | 1.522537 | 1.502618 | 1.535914 | 1.614484 | 1.632636 | 1.660059 |
| 0.5 | 1.549488 | 1.508876 | 1.560079 | 1.545529 | 1.540284 | 1.594191 | 1.798056 | 1.762891 | 1.612277 | 1.588902 |
| 1 | 1.579163 | 1.577823 | 1.629972 | 1.574172 | 1.698446 | 1.584639 | 1.632116 | 1.651837 | 1.72907 | 1.658346 |
| 1.25 | 1.789258 | 1.584628 | 1.62107 | 1.649523 | 1.714708 | 1.576569 | 1.628595 | 1.801045 | 1.697402 | 1.773875 |
| 2.5 | 1.779931 | 1.848244 | 1.705617 | 1.753231 | 1.82839 | 1.856705 | 1.660392 | 1.683915 | 2.068846 | 1.839103 |
| 5 | 1.811285 | 1.596678 | 1.618922 | 1.623561 | 1.817339 | 1.785522 | 1.715203 | 1.755084 | 1.724094 | 1.956152 |
| 10 | 1.714555 | 1.654457 | 1.728899 | 1.680408 | 1.843235 | 1.749089 | 1.767347 | 1.782298 | 1.763858 | 1.777877 |
| 25 | 1.887239 | 1.670588 | 1.701167 | 1.616021 | 1.769157 | 1.723982 | 1.691715 | 1.832902 | 1.740039 | 1.949161 |
| 50 | 1.781377 | 1.722955 | 1.718569 | 1.780917 | 1.924024 | 1.795398 | 1.795477 | 1.694828 | 1.632392 | 1.891473 |
| 100 | 1.791899 | 1.877337 | 1.77907 | 1.9375 | 1.726356 | 1.744098 | 1.961135 | 1.800952 | 1.606155 | 2.155804 |

HA

Effects of PPS alone and in combination with PBA-1202P on 35S-PG synthesis (DPM)/microgram DNA by mouse ATDC5 cell monolayer cultures expressed as percentage of control maintainance medium (MM)

Reverse Transcription-PCR detection of Runx 2, MPG, HAS3 and CD44 gene expression in ATDC5 cells cultured for 2-days with a serial combinations of PPS and PBA-1202P.

Reverse Transcription-PCR detection of Runx 2, Smad2 and Smad4 gene expression in ATDC5 cells cultured for 2-days with a serial combinations of PPS and PBA-1202P.

Figure 35

```
<210>  2
<211>  245
<212>  PRT
<213>  Homo sapiens

<400>  2

Ala Val Lys Arg Arg Pro Arg Phe Pro Val Asn Ser Asn Ser Asn Gly
1               5                   10                  15

Gly Asn Glu Leu Cys Pro Lys Ile Arg Ile Gly Gln Asp Asp Leu Pro
            20                  25                  30

Gly Phe Asp Leu Ile Ser Gln Phe Gln Val Asp Lys Ala Ala Ser Arg
            35                  40                  45

Arg Ala Ile Gln Arg Val Val Gly Ser Ala Thr Leu Gln Val Ala Tyr
    50                  55                  60

Lys Leu Gly Asn Asn Val Asp Phe Arg Ile Pro Thr Arg Asn Leu Tyr
65                  70                  75                  80

Pro Ser Gly Leu Pro Glu Glu Tyr Ser Phe Leu Thr Thr Phe Arg Met
                85                  90                  95

Thr Gly Ser Thr Leu Lys Lys Asn Trp Asn Ile Trp Gln Ile Gln Asp
            100                 105                 110

Ser Ser Gly Lys Glu Gln Val Gly Ile Lys Ile Asn Gly Gln Thr Gln
            115                 120                 125

Ser Val Val Phe Ser Tyr Lys Gly Leu Asp Gly Ser Leu Gln Thr Ala
    130                 135                 140

Ala Phe Ser Asn Leu Ser Ser Leu Phe Asp Ser Gln Trp His Lys Ile
145                 150                 155                 160

Met Ile Gly Val Glu Arg Ser Ser Ala Thr Leu Phe Val Asp Cys Asn
                165                 170                 175

Arg Ile Glu Ser Leu Pro Ile Lys Pro Arg Gly Pro Ile Asp Ile Asp
            180                 185                 190

Gly Phe Ala Val Leu Gly Lys Leu Ala Asp Asn Pro Gln Val Ser Val
            195                 200                 205

Pro Phe Glu Leu Gln Trp Met Leu Ile His Cys Asp Pro Leu Arg Pro
    210                 215                 220

Arg Arg Glu Thr Cys His Glu Leu Pro Ala Arg Ile Thr Pro Ser Gln
225                 230                 235                 240

Thr Thr Asp Glu Arg
                245
```

Figure 36

```
<210>  5
<211>  678
<212>  PRT
<213>  Homo sapiens

<400>  5

Met Ala Trp Thr Ala Arg Asp Arg Gly Ala Leu Gly Leu Leu Leu Leu
1               5                   10                  15
Gly Leu Cys Leu Cys Ala Ala Gln Arg Gly Pro Pro Gly Glu Gln Gly
            20                  25                  30
Pro Pro Gly Pro Pro Gly Pro Pro Gly Val Pro Gly Ile Asp Gly Ile
        35                  40                  45
Asp Gly Asp Arg Gly Pro Lys Gly Pro Pro Gly Pro Pro Gly Pro Ala
    50                  55                  60
Gly Glu Pro Gly Lys Pro Gly Ala Pro Gly Lys Pro Gly Thr Pro Gly
65                  70                  75                  80
Ala Asp Gly Leu Thr Gly Pro Asp Gly Ser Pro Gly Ser Ile Gly Ser
                85                  90                  95
Lys Gly Gln Lys Gly Glu Pro Gly Val Pro Gly Ser Arg Gly Phe Pro
            100                 105                 110
Gly Arg Gly Ile Pro Gly Pro Pro Gly Pro Pro Gly Thr Ala Gly Leu
        115                 120                 125
Pro Gly Glu Leu Gly Arg Val Gly Pro Val Gly Asp Pro Gly Arg Arg
    130                 135                 140
Gly Pro Pro Gly Pro Pro Gly Pro Pro Gly Pro Arg Gly Thr Ile Gly
145                 150                 155                 160
Phe His Asp Gly Asp Pro Leu Cys Pro Asn Ala Cys Pro Pro Gly Arg
                165                 170                 175
Ser Gly Tyr Pro Gly Leu Pro Gly Met Arg Gly His Lys Gly Ala Lys
            180                 185                 190
Gly Glu Ile Gly Glu Pro Gly Arg Gln Gly His Lys Gly Glu Glu Gly
        195                 200                 205
Asp Gln Gly Glu Leu Gly Glu Val Gly Ala Gln Gly Pro Pro Gly Ala
    210                 215                 220
Gln Gly Leu Arg Gly Ile Thr Gly Ile Val Gly Asp Lys Gly Glu Lys
225                 230                 235                 240
Gly Ala Arg Gly Leu Asp Gly Glu Pro Gly Pro Gln Gly Leu Pro Gly
                245                 250                 255
Ala Pro Gly Asp Gln Gly Gln Arg Gly Pro Pro Gly Glu Ala Gly Pro
            260                 265                 270
Lys Gly Asp Arg Gly Ala Glu Gly Ala Arg Gly Ile Pro Gly Leu Pro
        275                 280                 285
Gly Pro Lys Gly Asp Thr Gly Leu Pro Gly Val Asp Gly Arg Asp Gly
    290                 295                 300
Ile Pro Gly Met Pro Gly Thr Lys Gly Glu Pro Gly Lys Pro Gly Pro
305                 310                 315                 320
Pro Gly Asp Ala Gly Leu Gln Gly Leu Pro Gly Val Pro Gly Ile Pro
                325                 330                 335
Gly Ala Lys Gly Val Ala Gly Glu Lys Gly Ser Thr Gly Ala Pro Gly
            340                 345                 350
Lys Pro Gly Gln Met Gly Asn Ser Gly Lys Pro Gly Gln Gln Gly Pro
        355                 360                 365
Pro Gly Glu Val Gly Pro Arg Gly Pro Gln Gly Leu Pro Gly Ser Arg
    370                 375                 380
Gly Glu Leu Gly Pro Val Gly Ser Pro Gly Leu Pro Gly Lys Leu Gly
385                 390                 395                 400
Ser Leu Gly Ser Pro Gly Leu Pro Gly Leu Pro Gly Pro Pro Gly Leu
                405                 410                 415
Pro Gly Met Lys Gly Asp Arg Gly Val Val Gly Glu Pro Gly Pro Lys
            420                 425                 430
Gly Glu Gln Gly Ala Ser Gly Glu Glu Gly Glu Ala Gly Glu Arg Gly
        435                 440                 445
Glu Leu Gly Asp Ile Gly Leu Pro Gly Pro Lys Gly Ser Ala Gly Asn
    450                 455                 460
Pro Gly Glu Pro Gly Leu Arg Gly Pro Glu Gly Ser Arg Gly Leu Pro
465                 470                 475                 480
Gly Val Glu Gly Pro Arg Gly Pro Pro Gly Pro Arg Gly Val Gln Gly
                485                 490                 495
Glu Gln Gly Ala Thr Gly Leu Pro Gly Val Gln Gly Pro Pro Gly Arg
            500                 505                 510
Ala Pro Thr Asp Gln His Ile Lys Gln Val Cys Met Arg Val Ile Gln
        515                 520                 525
Glu His Phe Ala Glu Met Ala Ala Ser Leu Lys Arg Pro Asp Ser Gly
    530                 535                 540
Ala Thr Gly Leu Pro Gly Arg Pro Gly Pro Pro Gly Pro Pro Gly Pro
545                 550                 555                 560
Pro Gly Glu Asn Gly Phe Pro Gly Gln Met Gly Ile Arg Gly Leu Pro
                565                 570                 575
Gly Ile Lys Gly Pro Pro Gly Ala Leu Gly Leu Arg Gly Pro Lys Gly
            580                 585                 590
Asp Leu Gly Glu Lys Gly Glu Arg Gly Pro Pro Gly Arg Gly Pro Asn
        595                 600                 605
Gly Leu Pro Gly Ala Ile Gly Leu Pro Gly Asp Pro Gly Pro Ala Ser
    610                 615                 620
Tyr Gly Arg Asn Gly Arg Asp Gly Glu Arg Gly Pro Pro Gly Val Ala
625                 630                 635                 640
Gly Ile Pro Gly Val Pro Gly Pro Pro Gly Pro Pro Gly Leu Pro Gly
                645                 650                 655
Phe Cys Glu Pro Ala Ser Cys Thr Met Gln Ala Gly Gln Arg Ala Phe
            660                 665                 670
Asn Lys Gly Pro Asp Pro
        675
```

FIGURE 37

```
              10              20              30          40              50              60          70
Bovine  PRFPVNSNSN  GENELCPKVR  IGQDDLPGFD  LISQFQIDKA  ASRRAIQRVV  GSTALQVAYK  LGNNVDFRIP
human   PRFPVNSNSN  GGNELCPKIR  IGQDDLPGFD  LISQFQVDKA  ASRRAIQRVV  GSATLQVAYK  LGNNVDFRIP
mouse   ARFPANSISN  GGSELCPKIR  IGQDDLPGFD  LISQFQIEKA  ASRRTIQRVV  GSTALQVAYK  LGSNVDFRIP
chick   SRLPVTLGAR  QRTDLCPTIR  IGQDDLPGFD  LISQFQIEKA  ASQGIVQRVV  GSTALQVAYK  LGPNVDFRIP
SEQ ID            R                    IGQDDLPGFD  LISQFQIDKA(128)         K   LGNNVDFRI(125)

80              90             100         110             120             130         140
bovine  TRHLYPNGLP  EEYSFLTTFR  MTGSTLEKHW  SIWQIQDSSG  KEQVGVKING  QTKSVSFSYK  GLDGSLQTAA
human   TRNLYPSGLP  EEYSFLTTFR  MTGSTLKKNW  NIWQIQDSSG  KEQVGIKING  QTQSVVFSYK  GLDGSLQTAA
mouse   TRHLYPSGLP  EEYSFLTTFR  MTGSTLEKHW  NIWQIQDSAG  REQVGVKING  QTKSVAFSYK  GLDGSLQTAA
chick   TSAIYSNGLP  DEYSFLTTFR  MTGATLQKYW  TIWQIQDSSG  KEQVGVNLNG  PMKSVEFSYK  GVDGSLQTAS
SEQ ID  RHLYPNGLP   EEYSFLTTFR    KHW      SIWQIQDSSG  K(127)       KSVSFSYK    G(123)
                                  M(129)                                          K   GLDGSLQTAA 150             160             170         180             187
bovine  FSNLPSLFDS  QWHKIMIGVE  RSSATLFVDC  NRIESLPIKP  RGQIDVD
human   FSNLSSLFDS  QWHKIMIGVE  RSSATLFVDC  NRIESLPIKP  RGPIDID
mouse   FLNLPSLFDS  RWHKLMIGVE  RTSAILFIDC  IRIESLPIKP  RGQIDAD
chick   FLHLPFLFDS  QWHKLMISVE  TTSVTLFIDC  IKVETLNIKP  KGKISVD
SEQ ID              KIMIGVE     RS(124)     RIESLPIKP   RG(126)
        FSNKQSKFDS  QWHKI(130)  RSSATLFVDC  NRI(131)
```

Bovine = SEQ ID NO: 1
Human = SEQ ID NO: 2
Mouse = SEQ ID NO: 8
Chick = SEQ ID NO: 6

PROTECTION OF PROGENITOR CELLS AND REGULATION OF THEIR DIFFERENTIATION

RELATED APPLICATIONS

This application is a Continuation Application of U.S. patent application Ser. No. 15/235,613, filed Aug. 12, 2016, which is a Continuation Application of U.S. patent application Ser. No. 12/746,343, filed Sep. 28, 2010 which is the National Stage of International Application No. PCT/AU2008/001795, filed on Dec. 4, 2008, which claims the benefit of Australian Patent Application Serial No. 2007906607, filed on Dec. 4, 2007; the entire contents of each of which applications are incorporated herein by reference.

SEQUENCE LISTING

The instant application contains a Sequence Listing which has been submitted electronically in ASCII format and is hereby incorporated by reference in its entirety. Said ASCII copy, created on Oct. 25, 2016, is named PRR-001.02_SL.txt and is 30,748 bytes in size.

FIELD OF THE INVENTION

The present invention relates to the use of polysulfated polysaccharides in combination with progenitor cells to improve the viability of the progenitor cells including improving the cryopreservation of the progenitor cells and provides novel compositions, methods and uses. The present invention also relates to the use of polysulfated polysaccharides to regulate the proliferation and differentiation of progenitor cells.

BACKGROUND OF THE INVENTION

Human progenitor cells are the immature cells that give rise to all of the different types of mature cells that make up the organs and tissues of the adult body. The transition from progenitor cell to mature, specialised adult cell is via a process called differentiation.

Progenitor cells in the body take different pathways of differentiation in response to different stimuli from their environment. Similarly, progenitor cells in the laboratory can be stimulated to differentiate along different pathways by exposing them to various combinations of biochemicals. With appropriate stimuli, progenitor cells can differentiate into, among other tissues, blood cells, bone, cartilage, fat, blood vessels or heart muscle. Because of this, great interest is given to the use of progenitor cells as the basis of treatments to repair and re-grow of a range of tissues and organs.

Progenitor cells exist in the embryo and also in adult tissues such as bone marrow, fat, skin and dental pulp, though in much smaller relative numbers than in the embryo. The two types of adult progenitor cells are haematopoietic, which give rise to new bone marrow and blood cells, and non-haematopoietic, which give rise to solid organs and tissues, such as bone, heart and cartilage. Haematopoietic-type adult progenitor cells can be readily obtained from bone marrow and are already being used clinically. However, technology related to non-haematopoietic-type adult progenitor cells is much less developed due to the difficulty of obtaining sufficient numbers of these cells and of growing them in the laboratory.

In order to use progenitor cells in therapy it is necessary to be able to successfully store the progenitor cells prior to their use. The progenitor cells must be stored in such a way that they are effectively preserved and their viability is maintained. In general, the progenitor cells are cryopreserved for storage and thawed prior to use.

Cryogenic preservation (storage below $-100°$ C.) of cell cultures is widely used to maintain backups or reserves of cells without the associated effort and expense of feeding and caring for them. The success of the freezing process depends on four critical areas, proper handling of the cultures, controlled freezing, proper storage and an appropriate cryoprotective agent. The last point is particularly important and a suitable agent can assist in maintaining the viability of the cells.

In a clinical setting, it is particularly important that following cryopreservation, the cells remain viable and any increase in the viability of the cells will boost the effect of the treatment.

In addition, in order for the progenitor cells to be therapeutically effective it is necessary for them to differentiate into the required cell type. Thus, there is also a need to develop effective regulators of progenitor cell differentiation to ensure that the progenitor cells differentiate into the required cell type.

Furthermore, there is also a need to develop effective regulators of progenitor cell proliferation. It is often desirable for the progenitor cells to proliferate both in vitro and in vivo.

Therefore, there remains a need for agent(s) which can protect the progenitor cells during cryopreservation, enhance their viability, regulate their differentiation and/or regulate their proliferation.

SUMMARY OF THE INVENTION

The present inventors have now found that polysulfated polysaccharides or biologically active molecular fragments thereof can improve the viability of progenitor cells. In particular, present inventors have found that polysulfated polysaccharides or biologically active molecular fragments thereof can enhance cryopreservation of progenitor cells.

The present inventors have also found that polysulfated polysaccharides or biologically active molecular fragments thereof can regulate the proliferation of progenitor cells.

The present inventor has also found that polysulfated polysaccharides or biologically active molecular fragments thereof can regulate the differentiation of progenitor cells. Regulation may be upregulation or downregulation. It has been found that polysulfated polysaccharides or biologically active molecular fragments thereof can regulate differentiation into chondrocytes, osteoblasts, and adipocytes. In particular, it has been found that polysulfated polysaccharides or biologically active molecular fragments thereof can induce chondrogenesis.

These findings indicate that polysulfated polysaccharides or biologically active molecular fragments thereof can be used in combination with progenitor cells to improve or enhance the viability of the progenitor cells after cryopreservation and can be used in combination with progenitor cells in in vitro and in vivo methods and uses.

These unexpected findings therefore open up the possibility of using the polysulfated polysaccharides or a biologically active molecular fragment thereof in a number of new applications. For example, by regulating differentiation, particularly chondrogenesis, it is possible, among other things, to rebuild cartilage and intervertebral discs, prevent the degradation of joints and enhance the repair of avascular connective tissues. Prior to the present invention, it was not known that the polysulfated polysaccharides could regulate differentiation of progenitor cells, particularly chondrogenesis. Furthermore, by regulating proliferation, it is possible to control the production of progenitor cells both in vitro and in vivo. While the use of polysulfated polysaccharides in relation to osteo arthritis (OA) treatments per se has been published, it was not previously known that polysulfated polysaccharide have advantageous cryopreservation properties in relation to progenitor cells or that they can regulate differentiation and/or cell proliferation of said cells. Therefore, this opens up new treatment avenues that were not considered before.

As used herein a "biologically active molecular fragment" is a portion of a molecule of the invention which maintains a defined activity of the full-length molecule, namely in one embodiment to be able to enhance viability, to regulate cell differentiation and/or to regulate cell proliferation.

Accordingly, in a first embodiment, the present invention provides a composition comprising a progenitor cell together with a polysulfated polysaccharide or biologically active molecular fragment thereof.

In a further embodiment, the present invention provides a composition comprising progenitor cells, and a polysulfated polysaccharide or biologically active molecular fragment thereof, together with a carrier medium.

The carrier medium may be a culture medium, bioscaffold, cryopreservation medium, physiological media and/or a pharmaceutically acceptable carrier.

In a further embodiment, the present invention provides a composition comprising progenitor cells and a polysulfated polysaccharide or biologically active molecular fragment thereof, together with a cryopreservation medium.

The composition may be used both in vitro and in vivo.

The composition can contain any number of progenitor cells. In a further embodiment, the present invention contains about 1000 to about $1 \times 10^{10}$ progenitor cells. In a further embodiment, the present invention contains about $1 \times 10^5$–$1 \times 10^9$ cells. In a further embodiment, the present invention contains 100,000 to about $5 \times 10^8$ progenitor cells. In a further embodiment, the present invention contains about 500,000 to about $2 \times 10^8$ progenitor cells, about $1 \times 10^6$ to about $2 \times 10^8$ progenitor cells, or about $1 \times 10^6$ to about $1 \times 10^8$ progenitor cells. In a yet further embodiment, the composition contains about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, or $9 \times 10^8$ progenitor cells. In a yet further embodiment, the composition contains about $1 \times 10^8$ progenitor cells.

In one embodiment, the concentration of the polysulfated polysaccharide in the composition will depend on the number of cells in the composition. Thus, in one embodiment, the concentration of the polysulfated polysaccharide in the composition is from 500 ng/ml/million cells-10 mg/ml/million cells, or 500 ng/ml/million cells-2000 μg/ml/million cells, 1 μg/ml/million cells-1000 μg/ml/million cells, or 1 μg/ml/million cells-500 μg/ml/million cells.

In a further embodiment, the polysulfated polysaccharide concentration is in the range of 500 ng-10 μg/ml/million cells; 1 μg-10 μg/ml/million cells; 1 μg-8 μg/ml/million cells; 1 μg-6 μg/ml/million cells; 1 μg-5 μg/ml/million cells; 1 μg-3 μg/ml/million cells; 2 μg-6 μg/ml/million cells; 2.5 μg-5 μg/ml/million cells; or 3 μg-5 μg/ml/million cells. In a further embodiment, the polysulfated polysaccharide concentration is in the range of 1 μg-100 μg/ml/million cells; 1 μg-50 μg/ml/million cells; 1 μg-20 μg/ml/million cells; 1 μg-15 μg/ml/million cells; 10 μg-100 μg/ml/million cells; 20 μg-100 μg/ml/million cells; or 50 μg-100 μg/ml/million cells. In a further embodiment, the polysulfated polysaccharide concentration is in the range of 1 μg-1000 μg/ml/million cells; 100 μg-800 μg/ml/million cells; 100 μg-600 μg/ml/million cells; 100 μg-500 μg/ml/million cells; 200 μg-500 μg/ml/million cells. In a further embodiment the polysulfated polysaccharide concentration is in the range of 250 μg-500 μg/ml/million cells.

In one embodiment, the polysulfated polysaccharide concentration comprises 500 ng, 1 μg, 2 μg, 2.5 μg, 10 μg, 15 μg, 20 μg, 30 μg, 40 μg, 50 μg, 60 μg, 70 μg, 80 μg, 90 μg, 100 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg, 1000 μg, 1050 μg, 1100 μg, 1150 μg, 1200 μg, 1250 μg, 1300 μg, 1350 μg, 1400 μg, 1450 μg, 1500 μg, 1550 μg, 1600 μg, 1650 μg, 1700 μg, 1750 μg, 1800 μg, 1850 μg, 1900 μg, 1950 μg, or 2000 μg/ml/million cells. In a further embodiment, the polysulfated polysaccharide concentration comprises polysulfated polysaccharide concentrations comprise 200 μg/ml/million cells, 250 μg/ml/million cells, 300 μg/ml/million cells, 400 μg/ml/million cells, or 500 μg/ml/million cells. In a yet further embodiment, the polysulfated polysaccharide concentration comprises 250 μg/ml/million cells or 500 μg/ml/million cells.

Alternatively, the concentration of the polysulfated polysaccharide is independent of the number of cells in the composition. Thus in a further embodiment of the present invention the concentration of the polysulfated polysaccharide in the composition is from 500 ng/ml-10 mg/ml; 500 ng/ml-2000 μg/ml; 1 μg/ml-1000 μg/ml; or 1 μg/ml-500 μg/ml.

In a further embodiment, the polysulfated polysaccharide concentration is in the range of 500 ng-10 μg/ml; 1 μg-10 μg/ml; 1 μg-8 μg/ml; 1 μg-6 μg/ml; 1 μg-5 μg/ml; 1 μg-3 μg/ml; 2 μg-6 μg/ml; 2.5 μg-5 μg/ml; or 3 μg-5 μg/ml. In a further embodiment, the polysulfated polysaccharide concentration is in the range of 1 μg-100 μg/ml; 1 μg-50 μg/ml; 1 μg-20 μg/ml; 1 μg-15 μg/ml; 10 μg-100 μg/ml; 20 μg-100 μg/ml; or 50 μg-100 μg/ml. In a further embodiment, the polysulfated polysaccharide concentration is in the range of 1 μg-1000 μg/ml; 100 μg-800 μg/ml; 100 μg-600 μg/ml; 100 μg-500 μg/ml; 200 μg-500 μg/ml. In a further embodiment, the polysulfated polysaccharide concentration is in the range of 1 mg-1000 μg/ml; 100 μg-800 μg/ml; 100 μg-600 μg/ml; 100 μg-500 μg/ml; 200 μg-500 μg/ml. In a further embodiment, the polysulfated polysaccharide concentration is in the range of 250 μg-500 μg/ml.

Further polysulfated polysaccharide concentration comprises 500 ng, 1 μg, 2 μg, 2.5 μg, 5 μg, 10 μg, 15 μg, 20 μg, 30 μg, 40 μg, 50 μg, 60 μg, 70 μg, 80 μg, 90 μg, 100 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg, 1000 μg, 1050 μg, 1100 μg, 1150 μg, 1200 μg, 1250 μg, 1300 μg, 1350 μg, 1400 μg, 1450 μg, 1500 μg, 1550 μg, 1600 μg, 1650 μg, 1700 μg, 1750 μg, 1800 μg, 1850 μg, 1900 μg, 1950 μg, or 2000 μg/ml. Further polysulfated polysaccharide concentrations comprise 200 μg/ml, 250 μg/ml, 300 μg/ml, 400 μg/ml, or 500 μg/ml. Further polysulfated polysaccharide concentrations comprise 250 μg/ml and 500 μg/ml.

Further compositions contain a total polysulfated polysaccharide content of 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, 60 mg, 70 mg, 80 mg, 90 mg, or 100 mg. Further compositions contain a total polysulfated polysaccharide content of 15-70 mg, 20-60 mg, or 25-50 mg.

A further embodiment comprises about $1\times10^6$-$1\times10^8$ progenitor cells and 25-50 mg polysulfated polysaccharide. A further embodiment contains $1\times10^8$ progenitor cells and 25-50 mg/ml polysulfated polysaccharide.

In a further embodiment, the polysulfated polysaccharide may be administered in an amount such as to produce a concentration of the polysulfated polysaccharide in the biological compartment of 0.01 to 100 micrograms/ml biological media, for example 0.1 to 50 micrograms per ml biological media, 0.1 to 50 micrograms per ml biological media, 0.1 to 10 micrograms per ml biological media, 1 to 10 micrograms per ml biological media, 2 to 8 micrograms per ml biological media, 4 to 6 micrograms per ml biological media, or 4, 5, or 6 micrograms per ml biological media.

By biological compartment, it is meant an area of the body such as the intervertebral disk, muscle, synovial joints, intra synovial tissue (meniscus, synovium), extra synovial tissue (capsule), intra tendon, extra tendon, cardium, pericardium, cardiac muscle, and/or intra adipose tissue, intra-ligamentum, extra-ligamentum, intra-dermal, subdermal, intra-peritoneally, intra-venously, intra-arterally. The biological media will depend on the biological compartment. Biological media includes blood, serum, plasma, synovial fluid, peritoneal fluid, serous fluid, or adipose tissues. Thus, for example, in a further embodiment, the polysulfated polysaccharide may be administered in an amount such as to produce a concentration of the polysulfated polysaccharide in the synovial joints of 1 to 10 micrograms per ml synovial fluid.

Carrier Medium

The composition may contain a carrier medium. In one embodiment, the carrier medium is an aqueous solution. The medium may optionally contain further components which preserves the normal physiological structure and functions of the cells, particularly in relation to maintaining their environmental osmolarity, pH, integrity and fluidity of its plasma membrane and intra-cellular organelles.

Suitable carriers for this invention include those conventionally used alone and in combination, e.g., water, saline, aqueous dextrose, lactose, Ringer's solution, Krebs mammalian Ringer solution, Earles's solution, Gey's solution, Simm's solution, Tyrode solution, hyaluronan, physiological buffered saline (PBS), Locke's solution, Hank's solution, Clark and Lubs buffer, buffers; buffers composed of MES-NaOH, HEPES-NaOH, TRICINE-NaOH, EPPS-NaOH, BICINE-NaOH, Tris(hydroxymethyl)aminomethane-HCl, Glycine-NaOH, sodium bicarbonte-$CO_2$, sodium carbonate-bicarbonate, sodium cacodylate, sodium hydrogen maleate-NaOH; culture media such as, Eagle's medium, Dulbecco's medium or buffer, McCoy's medium, Click's medium, Ames' medium, alpha MEM, DMEM, Ham's F12, Ham's F10, RPMI-1640CMRL 1066, and 1415 NCTC 135; commercial specialist cell line media eg Stemline® and Megacell® or commercial cryopreservation agents such as Profreeze® and CryoStor®.

Thus, in one embodiment, the carrier medium is an aqueous medium which may optionally further include one or more of the following components:

organic and/or inorganic salts;
buffers
proteins such as BSA or transferin;
growth factors and cytokines, including insulin like growth factor, insulin, fibroblast like growth factors; BMP-TGF-beta super family (eg, BMP-2, BMP-7, BMP-8, TGF beta) and fibroblast growth factor family, IGF, FGF, EGF, PDGF, VEGF;
animal sera including FBS, new-born calf, all other mammalian species;
cryopreservation agents such as Profreeze® and CryoStor®;
cryoprotectorants, including dimethyl sulfoxide (DMSO), glycerol, trehalose, sucrose and other sugars or dimethylacetamide;
carbohydrates;
vitamins/co-factors;
hormones
antibiotics
attachment factors;
amino acids;
plasma expanders like dextran;
plasma both human and other mammalian species;
plasma substitute;
hyaluronan and/or hyaluronic acid, both natural or cross linked.

Thus, in one embodiment, the carrier medium comprises an aqueous media selected from water, saline, aqueous dextrose, lactose, a buffered solution, hyaluronan and glycols, physiological buffered saline (PBS), Ringer's solution, Locke's solution, Hank's solution, minimum essential medium, minimum essential medium alpha (alpha MEM), or DMEM.

In one embodiment, the carrier medium comprises alpha MEM. In an alternative embodiment, the carrier medium comprises DMEM. In an alternative embodiment, the carrier medium comprises HAMS 12.

The carrier medium may additionally comprise cryopreservation agents such as propriety preparations like Profreeze® or CryoStor®.

In an alternative embodiment, the carrier medium may comprise cryopreservation agents such as propriety preparations like Profreeze® or CryoStor® as the aqueous solution. In this embodiment, the composition does not contain carriers like water, saline, aqueous dextrose, lactose, Ringer's solution, a buffered solution, hyaluronan, physiological buffered saline (PBS), Locke's solution, Hank's solution, alpha MEM; DMEM; or HAMS F12 and instead comprises a cryopreservation agents such as propriety preparations like Profreeze® or CryoStor®, optionally in combination with one or more cryoprotectorants such as dimethyl sulfoxide (DMSO), glycerol, trehalose, sucrose and other sugars or dimethylacetamide. As an example, the carrier medium may comprise or consist of Profreeze® and DMSO.

The carrier medium may act as a culture medium and may be supplemented with organic and/or inorganic salts, carbohydrates, vitamins, amino acids and/or other entities which fulfil the nutritional requirements of the cell allowing them to divide and function normally in vitro. In one embodiment, the carrier medium further comprises serum and/or protein supplements. Thus, the culture media may be supplemented with proteins, including but not limited to BSA or transferin. In addition to, or instead of, the culture medium may be supplemented with serum, for example foetal or neonatal blood which contain growth factors, eg foetal calf serum. Recipes for the preparation and method of use of these media are well known to those skilled in the art. Suitable media can be found in Adams RLP. Cell culture for Biochemists. Elsevier/North-Holland Biomedical Press, Amsterdam, N.Y., Oxford. 1980, pp 84-97 and pp 246-260. (ISBN 0-444-80199-5), and Dawson R M C, Elliott D C, Elliott W H and Jones K M, Data for Biochemical Research (Third Edition), Clarendon Press, Oxford, 2002, pp 417-448 (ISBN 0-19-855299-8) the contents of which are incorporated in its entirety.

In one embodiment, the carrier medium acts as a cryopreservation medium. Cryopreservation media for freeze-thawing cells includes the use of the commonly known carriers and/or culture media including the aqueous media described herein (either alone or in combination with serum protein supplements). Alternatively, the carrier medium may comprise or include propriety preparations such as Profreeze® and CryoStor®. To function as a carrier medium, in general compounds are added which protect the cell membrane and organelles from damage by ice crystals formed during the freeze-thawing process.

Thus, in a further embodiment, the carrier medium further comprises one or more cryoprotectorants. Suitable agents or cryoprotectorants include dimethyl sulfoxide (DMSO), glycerol, sucrose and other sugars. Examples of suitable agents can be found in Brudder S, Jaiswal N, Hainsworth S, WO9739104; Farrant, J. 1980. General observations on cell preservation. In: M. J. Ashwood-Smith and J. Farrant, Eds. Low Temperature Preservation in Medicine and Biology, Pitman Medical Limited, Kent, England, p. 1-18; Frederick V, et al. Recovery, survival and functional evaluation by transplantation of frozen-thawed mouse germ cells. Human Reprod. 2004, 19: 948-53, Pegg D E, Principles of Cryopreservation. Methods Mol Biol. 2007; 368: 39-57, the contents of which are incorporated by reference. Thus, in a further embodiment, the carrier medium further comprises an agent or cryoprotectorant selected from one or more of dimethyl sulfoxide (DMSO), glycerol, sucrose and other sugars. Alternative cryoprotectants include dimethylacetamide as an alternative to glycerol, trehalose and/or sucrose. In a further embodiment, the carrier medium comprises conventional cryoprotectants, optionally in combination with growth factors and/or differentiation factors. Examples of suitable carrier mediums can be found in WO9832333, WO9739104 or WO1997/039104.

In a yet further embodiment, the carrier medium further comprises a propriety preparations such as Profreeze® and CryoStor®. Profreeze is sold by Lonza-BioWhittaker as freezing medium containing components of non-animal origin.

The carrier medium may be supplemented with the agents or protectorants discussed herein, in particular DMSO, glycerol, sucrose and other sugars, and further in particular DMSO. In a particular embodiment, the carrier medium includes Profreeze®™ CDNAO Freezing Medium, optionally in combination with DMSO. In a further embodiment, the carrier medium comprises Alpha MEM, Profreeze®™ CDNAO Freezing Medium and DMSO.

The present invention contemplates and includes the possibility that the carrier medium fulfils multiple requirements. Thus, the carrier medium may function as both a culture medium and a cryopreservation medium. Equally, the carrier medium may function as both a cryopreservation medium and a pharmaceutically acceptable carrier.

The carrier medium may comprise dimethylsulfoxide (DMSO) and/or glycerol. In one embodiment, the carrier medium comprises dimethylsulfoxide (DMSO). In a further embodiment, the composition comprises 1-20% DMSO. In a yet further embodiment, the composition comprises 1-15% DMSO, 5-15% DMSO, 1-10% DMSO, 5% DMSO, 7.5% DMSO, 10% DMSO, 15% DMSO or 20% DMSO. In a particular embodiment, the DMSO is high purity grade DMSO.

Some cells may be adversely affected by prolonged contact with DMSO. This can be reduced or eliminated by adding the DMSO to the cell suspension at 4° C. and removing it immediately upon thawing. Alternatively, a lower concentration of DMSO can be used.

As a further possibility the carrier medium may comprise glycerol instead of DMSO. Thus, in an alternative embodiment, the carrier medium may comprise glycerol. In one embodiment, the glycerol is present at a concentration of 1-30%, 1-20%, 5-20%, 1-15%, 5-15%, 1-10% or 5-10%.

In one embodiment, the medium contains DMSO or glycerol in combination with DMEM, HETA-Starch and/or human serum components and/or other bulking agents.

In one embodiment, the carrier medium is acceptable for injection and does not affect the functionality of the cells. In one embodiment, the medium contains serum. In a further embodiment, the medium is a serum free medium.

In one embodiment, the carrier medium contains serum, in one embodiment human serum components. In an embodiment, the carrier medium further comprises foetal bovine serum (FBS). In one embodiment, the composition comprises 1-50% FBS. In a further embodiment, the composition comprises 1-20% FBS, 1-10% FBS, 5% FBS, 7.5% FBS, 10% FBS, 15% FBS or 20% FBS. Alternatively, suitable serum includes BSA, transferin and/or egg yolk proteins at the same possible concentrations.

An example of a serum based cryopreservation medium would be a carrier medium comprising an aqueous solution such as Ringer's solution, physiological buffered saline (PBS), Locke's solution, Hank's solution, alpha MEM, DMEM or HAMS F12 together with a cryoprotectorant such as dimethyl sulfoxide (DMSO), glycerol, trehalose, sucrose and other sugars or dimethylacetamide and serum such as FBS.

Thus, an example serum based cryopreservation medium would be a carrier medium comprising DMEM or alpha MEM, DMSO and serum (using, for example, foetal bovine serum).

The carrier medium may also be serum free and/or protein free and may be a chemically defined media. Examples of serum free media include, KnockOut™ Serum Replacement, KnockOut™ D-MEM, StemPro®-34 SFM.

An example of a serum-free medium would be a carrier medium comprising an aqueous solution such as Ringer's solution, physiological buffered saline (PBS), Locke's solution, Hank's solution, alpha MEM, DMEM or HAMS F12 together with a cryoprotectorant such as dimethyl sulfoxide (DMSO), glycerol, trehalose, sucrose and other sugars or dimethylacetamide and a cryopreservation medium such as propriety preparations like Profreeze® or CryoStor®.

Thus, an example serum based cryopreservation medium would be a carrier medium comprising alpha MEM, DMSO and Profreeze® or simply DMSO and Profreeze®.

In one embodiment, the carrier medium comprises Profreeze®. Profreeze® is a serum-free freezing medium and is specifically formulated for cryopreserving cells that have been propagated in serum-free media. This protein-free, non-animal component medium is free of natural animal proteins and maintains high cell viability upon recovery from frozen storage. In a further embodiment, the carrier medium comprises Profreeze® together with DMSO, with the DMSO optionally at 7.5 or 15%. Alternatively, the carrier medium may include CryoStor®.

In one embodiment, the medium may contain buffers. Buffers include DMEM, phosphate buffers, or CMF-PBS. Commonly used physiological buffers are all encompassed by the present invention. Example buffers can be found in the literature, for example, Lelong I H and Rebel G. pH drift of "physiological buffers" and culture media used for cell incubation during in vitro studies. J Pharmacol Toxicol Methods. 1998; 39: 203-210; John A Bontempo. Development of Biopharmaceutical Parenteral Dosage Forms. in Drugs and the Pharmaceutical Sciences. Marcel Dekker Inc, NY (ISBN: 0-8247-9981-X): pp 91-108, the contents of which are incorporated herein by reference.

The medium may optionally further comprise saccharides including dextran, trehalose, sucrose or dimethylacetamide (DMA).

In one embodiment, the composition comprises progenitor cells; polysulfated polysaccharides and a carrier medium comprising:
 an aqueous medium selected from water, saline, aqueous dextrose, lactose, Ringer's solution, a buffered solution, hyaluronan, glycols, physiological buffered saline (PBS), Locke's solution, Hank's solution, alpha MEM, DMEM, or HAMS F12;
 a cryopreservation medium, including Profreeze® or CryoStor; and
 a cryoprotectorant selected from dimethylsulfoxide (DMSO) and/or glycerol.

In one embodiment, the cryopreservation medium is Profreeze®.

In one embodiment, the aqueous medium is alpha MEM or DMEM.

In one embodiment the cryoprotectorant is DMSO.

In one embodiment, the aqueous medium is present in 1-99%, about 10%, about 20%, about 30%, about 40%, about 50%, about 60%, about 70%, about 80%, or about 90%.

In one embodiment, the cryopreservation medium is present in 1-99%, about 10%, about 20%, about 30%, about 40%, about 50%, about 60%, about 70%, about 80%, or about 90%.

In one embodiment, the cryoprotectorant is present in an amount of 1-50%, 1-30%, 1-15%, 1-10%, 1-7.5%, 2.5%, 5%, 7.5%, 10%, 12.5%, 15%, 17.5% or 20%.

In a further embodiment, there is provided progenitor cells together with a polysulfated polysaccharide or biologically active molecular fragment thereof, cryopreserved in about 5 mL of Profreeze®™ CDNAO Freezing Medium, 7.5% DMSO, and 50% Alpha MEM. Cell concentrations at the time of cryopreservation may be $90 \times 10^6$ cells/cryobags to $180 \times 10^6$ cells/cryobag in 5 mL of freezing medium.

In yet another embodiment, the carrier medium comprises a support matrix. The support matrix can otherwise be referred to as biomatrix or bioscaffold.

In another embodiment, the present invention provides a method of enhancing cryopreservation of progenitor cells, comprising exposing the progenitor cells to a polysulfated polysaccharide or biologically active molecular fragment thereof.

In another embodiment, the present invention provides the use of a polysulfated polysaccharide or biologically active molecular fragment thereof to enhance the cryopreservation of progenitor cells.

In another embodiment, the present invention provides a method of improving the viability of progenitor cells, comprising exposing a polysulfated polysaccharide or biologically active molecular fragment thereof to the progenitor cells.

In another embodiment, the present invention provides the use of a polysulfated polysaccharide or biologically active molecular fragments thereof to improve the viability of progenitor cells.

In another embodiment, the present invention provides the use of a polysulfated polysaccharide as a cryopreservation agent.

In a further embodiment, the present invention provides the use of a composition as defined herein to enhance the cryopreservation of progenitor cells. In another embodiment, the present invention provides a method of improving the viability of progenitor cells, comprising cryofreezing a composition as defined herein and subsequently thawing the composition.

Thus, for the first time, it has been shown that the addition of polysulfated polysaccharides to cryogenic media does not have an adverse effect on the progenitor cells and does not have a detrimental effect on their viability. In fact, the addition of polysulfated polysaccharides to cryogenic media has been shown to enhance viability of the progenitor cells.

Furthermore, it has been shown that the addition of polysulfated polysaccharides to progenitor cells maintains or improves the viability of the progenitor cells per se. Thus, in a further embodiment there is provided the use of polysulfated polysaccharides to maintain or improve the viability of progenitor cells. In a further embodiment, there is provided a method of maintaining or improving the viability of progenitor cells comprising contacting a polysulfated polysaccharide to the progenitor cell.

It has also been found that polysulfated polysaccharides or biologically active molecular fragments thereof can regulate the proliferation of progenitor cells.

Thus, in another embodiment, the present invention provides a method of regulating the proliferation of progenitor cells, comprising exposing a polysulfated polysaccharide or biologically active molecular fragment thereof to a progenitor cell.

In another embodiment, the present invention provides the use of a polysulfated polysaccharide or biologically active molecular fragment thereof to regulate the proliferation of progenitor cells.

In a further embodiment, the present invention provides the use of a composition as defined herein to increase proliferation. Thus, in another embodiment, the present invention provides a method of regulating the proliferation of progenitor cells, comprising using a composition as defined herein. In another embodiment, the present invention provides the use of a composition as defined herein to regulate the proliferation of progenitor cells.

In one embodiment, proliferation is increased or unregulated.

Thus, for the first time, it has been shown that the use of polysulfated polysaccharides with progenitor cells can improve the proliferation of the progenitor cells. The polysulfated polysaccharides stimulate progenitor cell proliferation in a concentration dependent manner. Polysulfated polysaccharides can therefore be used in applications where it is desired to proliferate the cells. For example, in vitro proliferation of progenitor cells would be useful for expansion of the colony for application in the field of bioengineering. As an example, a bioscaffold could be impregnated with a colony of progenitor cells and perfused by a culture medium at 37° C. containing polysulfated polysaccharide(s). This would promote proliferation to further engraft and fill the scaffold thereby providing a more functional substitute tissue. As a further example, a pre-shaped (tubular or hemi-spherical) bioscaffold could be seeded with autologous or allogeneic progenitor cells and perfused with media containing polysulfated polysaccharide(s) to eventually produce a trachea or joint surface for transplantation in a host where these cartilages are defective.

Further information on these uses can be found in Chen F H and Tuan R S. Mesenchymal cells in rhematic diseases. Arthritis research and Therapy. 2008; 10: 223-239.

In vivo polysulfated polysaccharide stimulation of proliferation would be advantageous to facilitate engraftment into large defects (such as in joint cartilage) or compartments denuded of viable endogenous resident cells (eg the centre of the intervertebral disc) thereby reducing the time required for repair and reconstitution of the defect. Since progenitor cells are also a bountiful source of anti-inflammatory cytokines and immunosuppressive factors (see for example Aggarwal S and Pittenger A, Human progenitor cells modulate allogeneic immune cell responses. Blood. 2005; 105: 1815-1822, Tyndale A, et al. Immunomodulatory properties of progenitor cells: a review based on an interdisciplinary meeting held at the Kennedy Institute of Rheumatology Division, London, UK, 31 Oct. 2005. Arthritis Res Ther. 2007; 9: 301-15; Jorgensen C, et al. Multipotent mesenchymal stromal cells in articular disease. Best Practice and Research Clinical Rheumatology. 2008; 22: 269 284) their proliferation at sites of inflammation or antigenic response following injection would increase the potential for suppression of these unwanted cellular processes.

It has also been found that polysulfated polysaccharides can regulate differentiation of progenitor cells. The differentiation can be upregulated or downregulated.

In one embodiment there is provided a method of regulating differentiation of progenitor cells by exposing a polysulfated polysaccharide or biologically active molecular fragment thereof to a progenitor cell.

In a further embodiment, there is provided the use of a polysulfated polysaccharide or biologically active molecular fragment thereof to regulate the differentiation of progenitor cells.

The present invention regulates differentiation of progenitor cells. The cells of the present invention can differentiate into chondrocyte, osteoblast, and adipocyte lineages and in one embodiment can differentiate into cell types of different lineages, including bone, cartilage, adipose, muscle, tendon, and stroma.

In particular, in one embodiment of the present invention, the polysulfated polysaccharides or biologically active molecular fragments thereof can regulate differentiation into chondrocytes. In a further embodiment, the polysulfated polysaccharides or biologically active molecular fragments thereof can regulate differentiation into osteoblasts. In a yet further embodiment, the polysulfated polysaccharides or biologically active molecular fragments thereof can regulate differentiation into adipocytes. In a further embodiment, the polysulfated polysaccharides or biologically active molecular fragments thereof can regulate differentiation into fibrochondrocytes. In a further embodiment, the polysulfated polysaccharides or biologically active molecular fragments thereof can regulate differentiation into tenocytes. In a further embodiment, the polysulfated polysaccharides or biologically active molecular fragments thereof can regulate differentiation into cardiocytes.

In particular, it has been found that polysulfated polysaccharides or biologically active molecular fragments thereof can regulate and induce chondrogenesis.

In a further embodiment, the present invention regulates chondrogenesis in progenitor cells which support chondrocyte phenotype differentiation and survival. Therefore, in one aspect, the present invention relates to the formation of chondrocytes or fibrochondrocytes.

In a further embodiment the polysulfated polysaccharide upregulates differentiation. In an alternative embodiment, the polysulfated polysaccharide downregulates differentiation.

In one embodiment of the present invention there is provided a method of regulating chondgrogenesis in progenitor cells comprising applying a polysulfated polysaccharides to a progenitor cell.

In a further embodiment there is provided the use of a polysulfated polysaccharide to regulate chondrogenesis in progenitor cells.

In a further embodiment there is provided the use of a polysulfated polysaccharide to down regulate osteogenesis in progenitor cells.

In a further embodiment there is provided the use of a polysulfated polysaccharide to prevent osteogenesis by progenitor cells. This method or use may find application where production of bone would be harmful to the host such as at soft tissue sites which require flexibility and movement for normal function eg. muscle (heart), stroma, supportive connective tissues etc. or at sites where bone could impinge or entrap nerve fibres/roots or blood vessels leading to parathesis, paralysis, ischemia and potential irreversible tissue injury.

In a further embodiment there is provided a method of treating a cell to undergo chondrogenesis comprising contacting a progenitor cell with an effective amount of a polysulfated polysaccharide or a biologically active molecular fragment thereof, for a time and under conditions that stimulate the cell to differentiate.

Progenitor Cells

The term "progenitor cell" is intended to encompass any multipotent cell. Thus, the term progenitor cell encompasses adult and embrionic stem cells.

In one embodiment, the progenitor cell is a mesenchymal progenitor cell.

In a further embodiment, the progenitor cell is an endogenous or exogenous embryonic or adult mesenchymal or mesenchymal progenitor cell. In a further embodiment, progenitor cell is a multipotent stromal cell. In a further embodiment, the cell is an adult undifferentiated mesenchymal cell.

In a further embodiment, the progenitor cell is a chondroprogenitor cell.

In one embodiment, the progenitor cells are derived from bone marrow. Alternatively, the progenitor cells are derived from cartilage, synovial tissue, muscle, adipose tissue, skin, umbilical cord, dental pulp, or other available sources.

In one embodiment the progenitor cell is a somatic cell, such as connective tissue cells repressed from differentiation by endogenous factors.

In a further embodiment, the progenitor cells are a population of cells enriched for Stro-$1^{bri}$, or homogeonous Stro-$1^{bri}$ cells, or Stro-$1^{bri}$ progeny cells.

Polysulfated Polysaccharides

The polysulfated polysaccharide family can be considered to be any naturally occurring or semi-synthetic/synthetic polysulfated polysaccharide or a biologically active fragment thereof that contains two or more sugar rings or carbohydrate structures to which one or more sulfate ester groups are covalently attached as exemplified by heparin and pentosan polysulfate.

According to one embodiment, the polysulfated polysaccharide or biologically active fragment thereof can be selected from, but are not limited to, naturally occurring high molecular weight heparin, low molecular weight heparins, heparan sulfate, pentosan polysulfate, chondroitin polysulfate, chitosan polysulfate, dermatan polysulfate sulodexide, dextran polysulfate, polysulfated insulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

In a further embodiment, the polysulfated polysaccharides include: pentosan polysulfate chondroitin polysulfate, chitosan polysulfate, dextran polysulfate and heparin (high and low molecular weight).

In a yet further embodiment, the polysulfated polysaccharides are pentosan polysulfate, dextran polysulfate and heparin.

In a yet further embodiment, the polysulfated polysaccharides are pentosan polysulfate, the sodium salt of pentosan polysulfate (NaPPS), the magnesium salt of pentosan polysulfate (MgPPS), and/or the calcium salt of pentosan polysulfate (CaPPS).

One particular polysulfated polysaccharide is pentosan polysulfate (PPS) or its sodium salt. Pentosan polysulfate has been shown to improve the viability of progenitor cells, enhance the cryopreservation of progenitor cells, regulate the proliferation of progenitor cells and/or regulate the differentiation of progenitor cells. Pentosan polysulfate has been shown to upregulate differentiation and in particular induce chondrogenesis.

An alternative polysulfated polysaccharide is dextran polysulfate. Dextran polysulfate has been shown to downregulate or repress differentiation and in particular downregulate or repress chondrogenesis.

Uses

The progenitor cells of the present invention can differentiate into a number of cell types including chondrocytes, fibrochondrocytes, osteoblasts and adipocytes.

Since progenitor cells can differentiate into chondrocytes or fibrochondrocytes, these cells are useful in the production of extracellular matrix. Extracellular matrix may be suitable for transplantation into a connective tissue defect in a subject in need of such a treatment.

The present invention can be used to induce cartilage repair, restoration or matrix neogenesis and attenuate its catabolism by administering a polysulfated polysaccharide or a biologically active molecular fragment thereof in combination with progenitor cells.

In a further embodiment, the compositions of the present invention can also be used as an immunosuppressant, anti-catabolic or anti-inflammatory agent. As an example, the composition of the present invention may be used in the treatment of rheumatoid arthritis.

The methods discussed herein can be used in vivo or in vitro. In vivo, the inserted progenitor cells may, among other things, rebuild cartilage in-situ. In addition, the resident progenitor cells in the joints may also be stimulated to rebuild cartilage in-situ thus forming an effective directed treatment.

In vitro, the present invention allows for the production of cartilage within a biomatrix that can subsequently be implanted into a patient. This could be used to generate cartilage to partially or totally replace articulating joint surfaces, for the replacement of cartilaginous/fibrocartilagenous tissues or any other tissues that might benefit from this process which have been injured or arise from genetic abnormalities that require surgical correction.

The present invention also finds use with patients that may not benefit from the medical or surgical treatments currently available. For example, many sportspersons or individuals who have suffered from acute injury caused by trauma may have cartilage/fibrocartilagenous defects which are symptomatic. The present invention provides a method that could be used to stimulate growth of new cartilage to replace the defective tissue. This can either be done in vivo by stimulating progenitor cell growth in the joint in-situ or in vitro via a suitable bioscaffold which is shaped so as to fit into the defect and subsequently inserted into the defect; or by both in vivo and in vitro methods. Alternatively it could be used with older patients with established joint degeneration such as in osteoarthritis of the peripheral joints and spine where the present invention could be used to stimulate growth of new cartilage to replace the defective tissue and prevent progression of osteophytes and reduce the inflammation which is often the cause of symptoms of these disorders.

In one embodiment, the present invention has identified compound(s) that can act as both a cryopreservation agent and as an agent which can regulate differentiation. In a further embodiment, the present invention has identified compound(s) that can act as both a cryopreservation agent and as an agent which can regulate proliferation. In a further embodiment, the present invention has identified compound (s) that which can regulate proliferation and regulate differentiation. In a further embodiment, the present invention has identified compound(s) that can act as a cryopreservation agent, as an agent which can regulate proliferation and as an agent which can regulate proliferation. Such multi-use compounds have not been previously found in relation to progenitor cells.

The present invention has identified families of molecules or their biologically active fragments that can independently or in combination with each other enhance the cryopreservation of progenitor cells, regulate their cell proliferation and or regulate their differentiation; thus, these molecules can be used in combination with progenitor cells in therapeutic treatment.

In particular, the present invention allows the progenitor cells to differentiate into chondrocytes/fibroblasts thereby allowing for the formation of cartilage or fibrocartilage. Therefore, the use of progenitor cells and polysulfated polysaccharide can be used to treat degenerative diseases, to treat cartilage/fibrocartilage defect and/or to preventing or minimising the progression of degenerative diseases and cartilage defects.

The present invention has identified a novel composition. This composition has therapeutic use and can be advantageously used either in vivo or in vitro. In one embodiment, the method is carried out in vivo. Alternatively, the method is carried out in vitro.

Therefore, in one embodiment of the present invention there is provided a composition as described herein for use as a medicament.

In a further embodiment of the present invention there is provided a composition as described herein for use in the treatment of any disease that is affected by a breakdown or reduction of cartilage, including diseases of the musculo-skeletal system including rheumatoid arthritis (RA), osteoarthritis (OA), and intervertebral disc degeneration (DD), degenerative diseases, and method of inducing cartilage repair, restoration or matrix neogenesis.

In a further embodiment of the present invention there is provided a composition as described herein for use in the treatment of any disease that is affected by a breakdown or reduction of cartilage, including diseases of the musculo-skeletal system including rheumatoid arthritis (RA), osteoarthritis (OA), and intervertebral disc degeneration (DD), degenerative diseases, and method of inducing cartilage repair, restoration or matrix neogenesis.

In a further embodiment of the present invention there is provided a composition as described herein for use in the treatment of any disease where the differentiation of progenitor cells via osteogenesis is unwanted. For example, bone formation is often unwanted for soft tissue repair such as intra-discal injection. Leakage of the cells from a disc into the spinal canal or onto the adjacent organs (eg oesophagus) can be disastrous. One example of this was seen when BMP-2 was placed in the disc space to promote spinal fusion (new bone). It was found that the use of recombinant bone morphogenetic proteins resulted in life threatening complications, due to ectopic bone formation adjacent to the disc space which caused airway and neurological compression.

In a further embodiment of the present invention there is provided a composition as described herein for use in the treatment of a disease that is affected by a breakdown or reduction of adipose tissue.

In a further embodiment of the present invention there is provided the use of a composition as described herein for the manufacture of a medicament for the treatment of any disease that is affected by a breakdown or reduction of cartilage, including diseases of the musculoskeletal system including rheumatoid arthritis (RA), osteoarthritis (OA), and intervertebral disc degeneration (DD), degenerative diseases, and method of inducing cartilage repair, restoration or matrix neogenesis.

Therefore, according to one embodiment of the present invention there is provided a method of treating, mitigating, reducing or preventing any disease that is affected by a breakdown or reduction of cartilage such as diseases of the musculoskeletal system including rheumatoid arthritis (RA), osteoarthritis (OA), and intervertebral disc degeneration (DD), degenerative diseases, and method of inducing cartilage repair, restoration or matrix neogenesis, comprising administering a therapeutically effective amount of a composition as defined herein.

Examples of such an application would be to inject the composition of the present invention into joints of individuals with cartilage or disc lesions or systemically for other less accessible sites, allowing the preparation to perfuse the tissue and cells thereby exerting its unique biological effects. Applications could include treating individuals who may not have clinical defined disease (often OA or related disorders) but have sustained a traumatic injury to joint tissues through, for example, sport or work-related activity.

The methods and uses of the present invention could also serve as a prophylactic method following arthroscopic or open surgery where cartilage or meniscal excision/debridement was necessary. It is well established that with time such post surgical patients will generally progress to exhibit symptomatic OA requiring medical treatment. It is not unlikely that by diminishing cartilage degradation symptoms may also improved because of the reduction in production of antigens which promote inflammation.

Thus, use of the compositions of the present invention discussed herein to regulate differentiation and/or cell proliferation of progenitor cells introduced into the patient can be used to treat, mitigate, reduce or prevent any disease that is affected by a breakdown or reduction of cartilage. Specific diseases include diseases of the musculoskeletal system including rheumatoid arthritis (RA), osteoarthritis (OA), and intervertebral disc degeneration (DD), degenerative diseases, and method of inducing cartilage repair, restoration or matrix neogenesis.

In one embodiment the composition is administered intravenously. According to a yet further embodiment, the composition is administered systemically. According to a yet further embodiment, the composition is administered intra-articularly. According to a yet further embodiment, the composition is administered intra-discally. According to a yet further embodiment, the composition is administered systemically.

In one embodiment is the method of injecting a polysulfated polysaccharide, in combination with progenitor cells, into the joint(s) of the patient. The polysulfated polysaccharide helps regulate differentiation and/or proliferation of the progenitor cells.

It has additionally been found that polysulfated polysaccharides of the present invention can also produce, upregulate or stimulate the production of hyaluronan or hyaluronic acid (HA) in the differentiated cells. The hyaluronic acid (HA) can be produced in an animal or cell, namely an animal in vivo or in a cell in vitro.

This unexpected finding means that the compositions of the present invention can be used to replace HA lost in joints, particularly synovial fluid, ether due to normal wear and tear, degenerative diseases or other acute traumas. As synovial fluid degenerates, its ability to protect and lubricate joints is reduced. This degrades the joint further and can also stimulate the production of autoantigens which causes yet further damage. In the past, one way of overcoming or at least mitigating this problem has been to replace the synovial fluid.

However, the present invention provides a means of stimulating the production of hyaluronan or hyaluronic acid (HA) without the need to replace the synovial fluid itself. The compositions of the present invention can be contacted with progenitor cells, which then differentiate into mesenchymal cells (e.g. chondrocytes or fibroblasts) to increase the production of HA. The HA is formed in situ and can be used to replace HA lost in synovial fluid which treats, reduces or at least mitigates the damage caused by the degenerative diseases or tissue degradation.

Thus, according to a further embodiment, the present invention relates to a method of producing, upregulating or stimulating the production of hyaluronan (HA), comprising administering a composition as defined herein.

In one embodiment of the present invention, the compositions methods and uses can be used to treat arthritis or other degenerative diseases. However, in an alternative embodiment, the present invention excludes methods to treat arthritis or other degenerative diseases. Specifically, in one aspect, the present invention includes the use of a polysulfated polysaccharide or biologically active molecular fragment thereof in combination with progenitor cells to treat arthritis or other degenerative diseases.

Thus, in one embodiment of the present invention, there is provided a method of treating a patient suffering from diseases of the musculoskeletal system including rheumatoid arthritis (RA), osteoarthritis (OA), and intervertebral disc degeneration (DD); degenerative diseases, osteoarthritis of synovial joints, ophthalmology, prevention of post-surgical abdominal adherences, skin treatment and repair and restoration of the function of the extracellular matrix; or for inducing cartilage repair, restoration or matrix neogenesis; comprising administering a composition as defined herein, to regulate differentiation and/or proliferation of the progenitor cells.

The patient or subject can be a human or animal patient. In one embodiment, the patient is a mammal including a human, horse, dog, cat, sheep, cow, or primate. In one embodiment the patient is a human. The patient may suffer from a degenerative disease and/or a cartilage defect. The patient may be an athlete or may have been subjected to a trauma causing joint damage.

The present invention encompasses methods of treatment involving polysulfated polysaccharides and progenitor cells. The present invention also encompasses the polysulfated polysaccharides and progenitor cells for use as a medicament; the use of the polysulfated polysaccharides and progenitor cells in the manufacture of a medicament for the treatments as discussed herein; and also compositions and formulations containing the polysulfated polysaccharides and progenitor cells.

Combination Therapies

The present invention has also identified for the first time polypeptides or a biologically active fragment thereof which can also regulate differentiation and cell proliferation, particularly regulate chondrogenesis and cell proliferation. The polypeptide is a non-collagenous NC4 domain of alpha IX collagen or a biologically active molecular fragment thereof (hereinafter NC4). The term "a biologically active fragment" is synonymous with the term "a biologically active molecular fragment".

Surprisingly, this invention has discovered that while the two separate families can exert their regulation of chondrogenesis and cell proliferation independently when combined together they can act synergistically, not only to increase their individual effects but to afford greater specificity of action.

These unexpected findings opens up the possibility of using a polysulfated polysaccharide in combination with NC4, in a number of new applications since by regulating chondrogenesis, it is possible, among other things, to rebuild cartilage and intervertebral discs, prevent the degradation of joints and enhance the repair of avascular connective tissues. Prior to the present invention, it was not known that a combination of a polysulfated polysaccharides and NC4 could regulate chondrogenesis and cell proliferation, and it was certainly not known that the combination would have a synergistic effect.

Accordingly, in a further embodiment, the present invention provides a composition comprising progenitor cells together with a polysulfated polysaccharide or biologically active molecular fragment thereof and NC4 or a biologically active molecular fragment thereof.

In a further embodiment, the composition further comprises a carrier medium, culture medium, cryopreservation medium and/or pharmaceutically acceptable carrier.

Thus, in a further embodiment, the present invention provides a composition comprising progenitor cells, a polysulfated polysaccharide or biologically active molecular fragment thereof and NC4 or a biologically active molecular fragment thereof, together with a carrier medium.

The carrier medium may be a culture medium, cryopreservation medium or pharmaceutically acceptable carrier.

Any reference to the compositions of the present invention which relate to progenitor cells and polysulfated polysaccharides also relate to composition containing progenitor cells, polysulfated polysaccharides and NC4, including the concentrations, cell numbers and/or types and amounts of optional further ingredients. In addition, the methods and uses of the compositions as defined herein also relate to the composition including both a polysulfated polysaccharide and NC4.

Thus, according to a further embodiment of the present invention, there is provided a method of regulating chondrogenesis and/or cell proliferation comprising administering a composition comprising progenitor cells, a polysulfated polysaccharide or biologically active molecular fragment thereof and NC4 or a biologically active molecular fragment thereof.

Thus, in another embodiment, the present invention provides a method of regulating the proliferation of progenitor cells, comprising exposing a polysulfated polysaccharide or biologically active molecular fragment thereof and NC4 or a biologically active molecular fragment thereof to a progenitor cell.

Thus, in another embodiment, the present invention provides a method of regulating differentiation of progenitor cells by exposing a polysulfated polysaccharide or biologically active molecular fragment thereof and NC4 or a biologically active molecular fragment thereof to the progenitor cells.

In one embodiment, the biologically active molecular fragment of NC4 has at least 65% amino acid identity to a fragment of SEQ ID NO:1.

In a further embodiment, the biologically active molecular fragment of NC4 has at least 65% amino acid identity to a fragment of SEQ ID NO:2.

In a yet further embodiment, the biologically active molecular fragment of NC4 has at least 65% amino acid identity to a fragment of SEQ ID NO:3, SEQ ID NO:4, SEQ ID NO:5, SEQ ID NO:6, SEQ ID NO:7, SEQ ID NO 8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

In a further embodiment, biologically active molecular fragment of NC4 has at least 65%, 70%, 75%, 80%, 85%, 90%, 95%, 98%, 99%, 100% amino acid identity to the frangments listed above.

It is also possible to administer or use the compositions of the present invention as part of a combination therapy. For example the polysaccharide(s) of the present invention may be administered in combination with one or more other compounds. These compounds may be a structure modifying osteoarthritis drug (SMOADs).

The present invention extends to combination therapies for use in the treatment of the diseases discussed herein. Particularly, in one example, the present invention extends to the use of a polysulfated polysaccharide in combination with a further agent for use in the treatment of various degenerative conditions. It should be understood that these agents can be administered at the same time or a different time. Thus the combination therapy may comprise the active agents being administered at the same time either in a single formulation or in multiple formulations administered at the same or different times. Equally, the combination therapy may comprise the active agents being administered in different formulations at different times. The formulations could be administered sequentially and may be separated by a period of time including hours, days, weeks and months.

The present invention also extends to the use of the polysulfated polysaccharides as discussed herein in combination with one or more growth factors. The present invention further extends to the methods, uses, formulations and/or compositions as disclosed herein in combination with one or more growth factors. Possible growth factors include insulin like growth factor, insulin, fibroblast like growth factors; BMP-TGF-beta super family (eg, BMP-2, BMP-7, BMP-8, TGF beta) and fibroblast growth factor family, IGF, FGF, EGF, PDGF and VEGF.

BRIEF DESCRIPTION OF THE FIGURES

FIG. 3. Effects of different concentrations of Pentosan Polysulfate (PPS) on progenitor cell viability following cryopreservation in liquid nitrogen and rapidly thawing as described in FIG. 1. Cell viability was determined using the mitochondrial dehydrogenase MTT assay. Data shown=Means±SD
*=p<0.05 relative to control values FIG. 4. The Effects of Pentosan Polysulfate (PPS) on Human Progenitor cell Proliferation. Primary human progenitor cells were cultured in 24 well plates in growth media supplemented with PPS at the indicated concentrations. At various time intervals (day 1, 3, 6), the growth media was removed and replaced with phenol red free media containing the tetrazolium salt WST-1 for 2 hours at 37° C./5% CO2. WST-1 is cleaved by mitochondrial dehydrogenase in viable cells to produce a formazan dye that can be detected using an ELISA plate reader at a wavelength of 450 nm. Absorbance at 450 nm for each time point is shown for all concentrations of PPS. A statistically significant increase in proliferation was observed on day 6 at concentrations of PPS in excess of 1 µg/ml (* p<0.01, ANOVA).

FIG. 7. The Effects of Pentosan Polysulfate (PPS) on Human progenitor cell Differentiation: Mineralisation Assay. Primary human progenitor cells were cultured in 96 wells plates in non-osteoinductive growth media (media control) or in osteoinductive conditions (alpha☐MEM supplemented with 10% FCS, 100 microM L-ascorbate-2-phosphate, dexamethasone 10$^{-7}$M and 3 mM inorganic phosphate) in the presence of PPS at the indicated concentrations. On day 28, the concentration of acid solubilisd calcium per well was determined using the Cresolphthalein Complexone method. (A) The concentration of acid solubilised calcium per microg of DNA/well was determined following the assessment of the total amount of DNA per well using a fluorogenic DNA stain (Hoeshst 33258). A statistically significant decrease in mineralised matrix formation was observed when concentrations of PPS of 1 ug/ml and 100 ug/ml were used (* p<0.01, ANOVA). (B) Phase-contrast photomicrographs of mineralised cultures at x20 magnification.

FIG. 8. The Effects of Pentosan Polysulfate (PPS) on Human progenitor cell Differentiation: Adipocyte Formation. Primary progenitor cells were cultured in 96 well plates in non-adipogenic growth media (media control) or under adipogenic conditions (0.5 mM methylisobutylmethylxanthine, 0.5 µM hydrocortisone, and 60 µM indomethacin) in the presence of PPS at the indicated concentrations. On day 28, the presence of lipid laden adipocytes was determined using the lipophilic dye Oil Red O. The relative amount of solubilised lipid per µg of DNA/well was determined following the assessment of the total amount of DNA per well using a fluorogenic DNA stain (Hoeshst 33258). (A) A statistically significant increase in adipocyte number was observed at concentrations of PPS in excess 1 ug/ml (* p<0.01, ANOVA). (A) Phase-contrast photomicrographs of Oil Red O labeled adipocytes at x20 magnification.

FIG. 9. Concentration dependent effects of Pentosan Polysulfate (PPS) on Murine Progenitor Cell (progenitor cells C3H10T1/2) biosynthesis of Proteoglycans (PGs) and DNA content when grown in monolayer cultures. Data shown=Means±SD.

FIG. 16. A bar graph showing the concentration dependent effects of PPS on proteoglycan synthesis by murine progenitor cells (C3H10T1-2) in micromass cultures for 6 days and 9 days. PPS was included in the media (Ham's F12+10% FCS) and was changed every 48 hours. $^{35}$S—SO$_4$ was added 24 hours before culture termination. Synthesis normalized to DNA content. * P<0.05, P<0.005, *P<0.0005 relative to controls.

FIG. 18. A: Bar graph showing the Pentosan Polysulfate (PPS) concentration dependent stimulation of type II collagen production by human progenitor cells in micromass cultures for 10 days as determined by scanning and digital analysis of the immuno stained micromass culures shown in B. (see text for details).

FIG. 31 shows that rhNC4 stimulated PG synthesis by the progenitor ATDC5 cells in the presence and absence of insulin, but more effectively at the higher concentrations in the absence of insulin.

FIG. 32 shows the concentration dependent stimulation of PG synthesis by Murine ATDC5 progenitor cells in the presence of PPS.

FIG. 35. SEQ ID NO:1—Amino acid sequence for full length human NC4 without signal peptide.

FIG. 36. SEQ ID NO:2—Amino acid sequence for truncated hNC4 obtained during expression from *K. lactis* cultures by action of putative by proline endopeptidase.

FIG. 37. A sequence composition between bovine human, murine and chick NC4 sequences.

Figure 1:
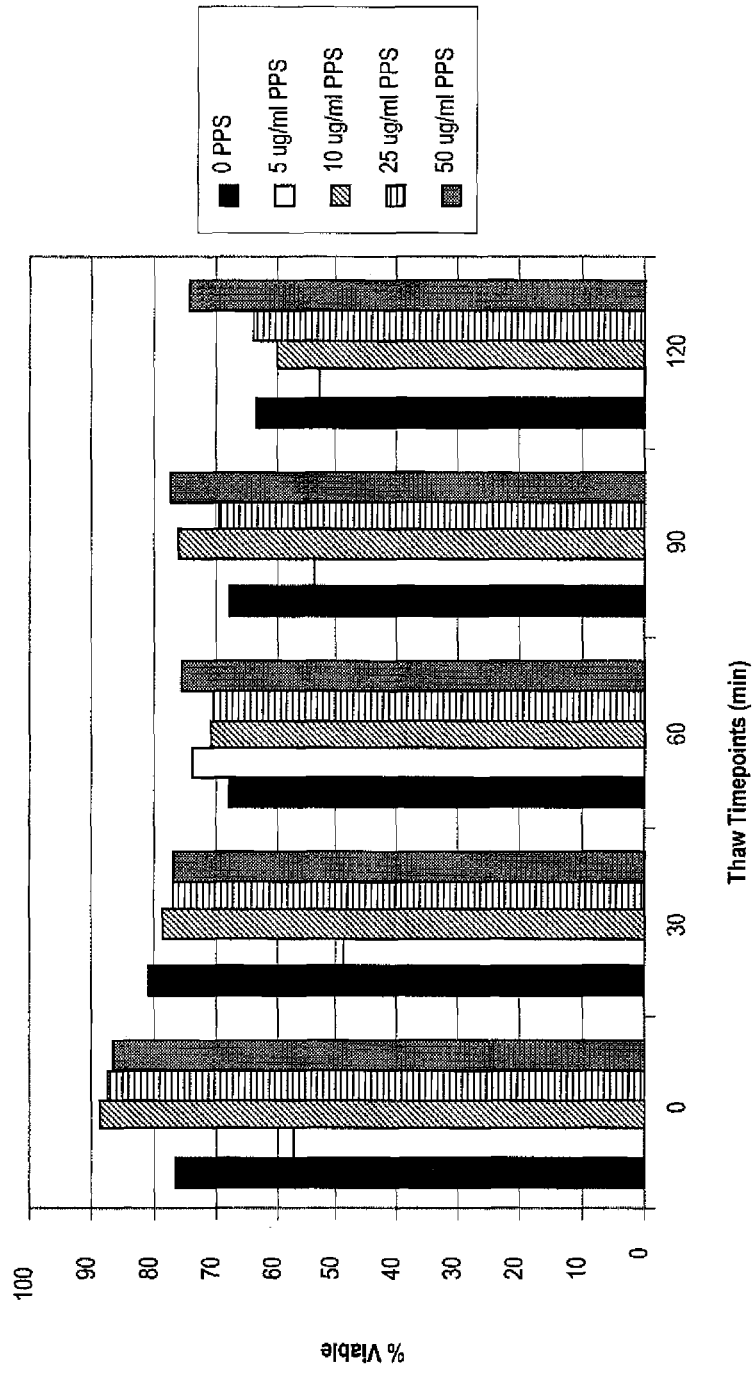
FIG. 1. The Effects of Pentosan Polysulfate (PPS) on Normal Human MSCs Freeze/Thaw Viabilities. MSCs were rapidly thawed in a 37° C. water bath and washed twice with HHF (HBSS containing 5% (v/v) Foetal Calf Serum). The cells were subsequently seeded into multiple T-75 flasks at 8,000 cells/cm$^2$. The cells were grown until 70-80% confluent, trypsinised and cryopreserved at cell concentrations of 50×10$^6$/ml in Profreeze®/7.5% DMSO supplemented with PPS at the indicated concentrations. Ampoules were retrieved from liquid nitrogen storage and rapidly thawed, gently mixed and 10 ul samples removed at time=0, 30, 60, 90 and 120 minutes. To each cell sample, 290 ul of trypan blue was added and cell counts/viability testing performed. PPS did not adversely affect cell viability.

DETAILED DESCRIPTION OF THE ILLUSTRATED AND EXEMPLIFIED EMBODIMENTS OF THE INVENTION

As used in the specification and claims, the singular form "a", "an" and "the" include plural references unless the context clearly dictates otherwise. For example, the term "a polypeptide" includes a plurality of polypeptides, including mixtures thereof.

As used herein the term "derived from" shall be taken to indicate that a specified integer are obtained from a particular source albeit not necessarily directly from that source.

A "composition" is intended to mean a combination of active agent and another compound or composition, inert (for example, a detectable agent or label) or active, such as an adjuvant.

Unless the context requires otherwise or specifically stated to the contrary, integers, steps, or elements of the invention recited herein as singular integers, steps or elements clearly encompass both singular and plural forms of the recited integers, steps or elements.

The embodiments of the invention described herein with respect to any single embodiment shall be taken to apply mutatis mutandis to any other embodiment of the invention described herein.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally equivalent products, compositions and methods are clearly within the scope of the invention, as described herein.

The present invention is performed without undue experimentation using, unless otherwise indicated, conventional techniques of molecular biology, microbiology, virology, recombining DNA technology, peptide synthesis in solution, solid phase peptide synthesis, and immunology. Such procedures are described, for example, in the following texts that are incorporated herein by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp35-81; Sproat et al., pp 83-115; and Wu et al., pp 135151;
4. Nucleic Acid Hybridization: A Practical Approach (B. D. Hames & S. J. Higgins, eds., 1985) IRL Press, Oxford, whole of text;
5. Perbal, B., A Practical Guide to Molecular Cloning (1984);
6. Wiinsch, E., ed. (1974) Synthese von Peptiden in Houben-Weyls Metoden der Organischen Chemie (Miiler, E., ed.), vol. 15, 4th edn., Parts 1 and 2, 30 Thieme, Stuttgart.
7. Handbook of Experimental Immunology, Vols. I-IV (D. M. Weir and C. C. Blackwell, eds., 1986, Blackwell Scientific Publications)

Progenitor Cells

The present invention relates to progenitor cells. In its broadest embodiment, the term progenitor cells is intended to encompass any multipotent cell. Thus, the term progenitor cell encompasses adult and embrionic stem cell.

The progenitor cell may be a mesenchymal progenitor cell.

The progenitor cell may be an endogenous or exogenous embryonic or adult mesenchymal or mesenchymal progenitor cell. The progenitor cell may be a multipotent stromal cell. The progenitor cell may be an adult undifferentiated mesenchymal cell.

The progenitor cell may be a chondroprogenitor cell.

The progenitor cells may be derived from bone marrow. Alternatively, the progenitor cells may be derived from cartilage, synovial tissue, muscle, adipose tissue, skin, umbilical cord, dental pulp, or other available sources.

The progenitor cells may be a somatic cell, such as connective tissue cells repressed from differentiation by endogenous factors.

In a further embodiment, the progenitor cells are a population of cells enriched for Stro-$1^{bri}$, or homogeneous Stro-$1^{bri}$ cells, or Stro-$1^{bri}$ progeny cells.

One type of progenitor cell is a mesenchymal progenitor cell (MPC). Originally derived from bone marrow, MPCs and MPC-like cells have been identified to exist in and can be isolated from a large number of adult tissues, where they are postulated to carry out the function of replacing and regenerating local cells that are lost to normal tissue turnover, injury, or aging. These tissues include adipose, periosteum, synovial membrane, synovial fluid (SF), muscle, dermis, deciduous teeth, pericytes, trabecular bone, infrapatellar fat pad, and articular cartilage.

MPCs may be defined retrospectively by a constellation of characteristics in vitro, including a combination of phenotypic markers and multipotential differentiation functional properties.

Although plastic adherence serves as the most commonly used and simple isolation procedure for mesenchymal cells, various positive and negative surface markers (for example, Stro-1, CD146/melanoma cell adhesion molecule, CD271/low-affinity nerve growth factor, and stage-specific embryonic antigen-4) have also been used to enrich MPC yield and homogeneity. In addition, a further panel of surface markers, including CD140b (platelet-derived growth factor receptor-D), CD340 (HER-2/erbB2), and CD349 (frizzled-9) in conjunction with CD217 can also be used for MPC enrichment.

Further progenitor cells include murine progenitor cells, including cell lines C3H10T1/2 and ATDC5 or M111 progenitor cells. C3H10T1/2 are progenitor stem cell line derived from bone marrow of female C3H/He mouse strain with fibroblast-like morphology. ATDC5 cells are mouse embryonic derived chondroprogenitor cell line with epithelial-like morphololy.

The C3H10T1/2 cell line was established in 1973 from 14- to 17-day-old C3H mouse embryos. These cells display fibroblastic morphology in cell culture and are functionally similar to mesenchymal stem cells. Inhibiting methylation in in C3H10T1/2 cells with 5-azacytidine produces stable morphological and biochemical features of muscle, adipose, bone, or cartilage cells It is suggested that this phenotypic alteration results from activation of endogenous genes in response to blocking methylation. In addition it has been shown that bone morphogenic protein 4 (BMP4), a member of the transforming growth factor type-beta superfamily, can induce commitment of C3H10T1/2 cells to preadipocytes that, when subjected to an adipocyte differentiation protocol, develop into cells of the adipocyte phenotype (Tang Qi-Qun, Otto T C, Lane M D. Commitment of C3H10T1/2 pluripotent stem cells to the adipocyte lineage. Pro Natl Acad Sci USA, 2004; 101: 9607-9611). The ATDC5 cell line was originally isolated from a differentiating culture of AT805 teratocarcinoma. ATDC5 cells express a fibroblastic cell phenotype in a growing phase. Further information on the ATDC5 cell line can be found in Atsumi T, Miwa Y, Kimata K, Ikawa Y. A chondrogenic cell line derived from a differentiating culture of AT805 teratocarcinoma cells. Cell Differ Dev. 1990; 30: 109-16.

The progenitor cells may be a population of cells enriched for Stro-$1^{bri}$. The progenitor cells may be homogeonous Stro-$1^{bri}$ cells, or Stro-$1^{bri}$ progeny cells.

Stro-$1^{bri}$ cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are typically capable of differentiating into germ lines such as mesoderm and/or endoderm and/or ectoderm. Thus, Stro-$1^{bri}$ cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. Stro-$1^{bri}$ cells may thus be non-hematopoietic progenitor cells which divide to yield daughter cells that are either stem cells or are precursor cells which in time will irreversibly differentiate to yield a phenotypic cell.

In a further embodiment, the Stro-$1^{bri}$ cells are enriched from a sample obtained from a subject, e.g., a subject to be treated or a related subject or an unrelated subject (whether of the same species or different). The terms 'enriched', 'enrichment' or variations thereof are used herein to describe a population of cells in which the proportion of one particular cell type or the proportion of a number of particular cell types is increased when compared with the untreated population.

In a further embodiment, the cells used in the present invention express one or more markers individually or collectively selected from the group consisting of $TNAP^+$, $VCAM-1^+$, $THY-1^+$, $STRO-2^+$, $CD45^+$, $CD146^+$, $3G5^+$ or any combination thereof.

By "individually" is meant that the invention encompasses the recited markers or groups of markers separately, and that, notwithstanding that individual markers or groups of markers may not be separately listed herein the accompanying claims may define such marker or groups of markers separately and divisibly from each other.

By "collectively" is meant that the invention encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

In one embodiment, the Stro-$1^{bri}$ cells are additionally one or more of $TNAP^+$, $VCAM-1^+$, $THY-1^+$, $STRO-2^+$ and/or $CD146^+$.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This terms means that the marker is expressed at a relatively very low level by that cell, and that it generates a very low signal when detectably labelled or is undetectable above background levels.

The term "bright", when used herein, refers to a marker on a cell surface that generates a relatively high signal when detectably labelled. Whilst not wishing to be limited by theory, it is proposed that "bright" cells express more of the target marker protein (for example the antigen recognised by STRO-1) than other cells in the sample. For instance, STRO-1$^{bri}$ cells produce a greater fluorescent signal, when labelled with a FITC-conjugated STRO-1 antibody as determined by fluorescence activated cell sorting (FACS) analysis, than non-bright cells (STRO-1$^{dull/dim}$). In one embodiment, "bright" cells constitute at least about 0.1% of the most brightly labelled bone marrow mononuclear cells contained in the starting sample. In other embodiments, "bright" cells constitute at least about 0.1%, at least about 0.5%, at least about 1%, at least about 1.5%, or at least about 2%, of the most brightly labelled bone marrow mononuclear cells contained in the starting sample. In a further embodiment, STRO-1$^{bright}$ cells have 2 log magnitude higher expression of STRO-1 surface expression relative to "background", namely cells that are STRO-1$^-$. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In a further embodiment, the TNAP is BAP. In a further embodiment, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in a further embodiment, the Stro-1$^{bri}$ cells are capable of giving rise to clonogenic CFU-F.

In one embodiment, a significant proportion of the multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another embodiment, the Stro-1$^{bri}$ cells are not capable of giving rise, upon culturing, to hematopoietic cells.

In one embodiment, the cells are taken from the subject to be treated, cultured in vitro using standard techniques and used to obtain expanded cells for administration to the subject as an autologous or allogeneic composition. In an alternative embodiment, cells of one or more of the established human cell lines are used. In another useful embodiment of the invention, cells of a non-human animal (or if the patient is not a human, from another species) are used.

The present invention also contemplates use of supernatant or soluble factors obtained or derived from Stro-1$^{bri}$ cells and/or progeny cells thereof (the latter also being referred to as expanded cells) which are produced from in vitro culture in combination with the progenitor cells. Expanded cells of the invention may a have a wide variety of phenotypes depending on the culture conditions (including the number and/or type of stimulatory factors in the culture medium), the number of passages and the like. In certain embodiments, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an embodiment, progeny cells useful for the methods of the invention are obtained by isolating TNAP$^+$STRO-1$^+$ multipotential cells from bone marrow using magnetic beads labelled with the STRO-3 antibody, and then culture expanding the isolated cells (see Gronthos et al. *Blood* 85: 929-940, 1995 for an example of suitable culturing conditions).

In one embodiment, such expanded cells (progeny) (optionally at least after 5 passages) can be TNAP$^-$, CC9$^+$, HLA class I$^+$, HLA class II$^-$, CD14$^-$, CD19$^-$, CD3$^-$, CD11a$^-$c$^-$, CD31$^-$, CD86$^-$, CD34$^-$ and/or CD80$^-$. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9$^-$). In one embodiment, expanded cells still have the capacity to differentiate into different cell types.

In one embodiment, an expended cell population used to obtain supernatant or soluble factors, or cells per se, comprises cells wherein at least 25%, in a further embodiment at least 50%, of the cells are CC9+.

In another embodiment, an expanded cell population used to obtain supernatant or soluble factors, or cells per se, comprises cells wherein at least 40%, in a further embodiment at least 45%, of the cells are STRO-1$^+$.

In a further embodiment, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD10, CD13, SCF, PDGF-R, EGF-R, IGF1-R, NGF-R, FGF-R, Leptin-R (STRO-2=Leptin-R), RANKL, STRO-1$^{bright}$ and CD146 or any combination of these markers.

In one embodiment, progeny cells derived from STRO-1$^{bri}$ cells are positive for the marker Stro-1$^{dim}$. These cells are referred to as Tissue Specific Committed Cells (TSCCs) and are more committed to differentiation than STRO-1$^{bri}$ cells are therefore less able to respond inductive factors. Non-limiting examples of the lineages to which TSCCs may be committed include hepatocyte progenitors, which are pluripotent for bile duct epithelial cells and hepatocytes; neural restricted cells, which can generate glial cell precursors that progress to oligodendrocytes and astrocytes, and neuronal precursors that progress to neurons; precursors for cardiac muscle and cardiomyocytes, glucose-responsive insulin secreting pancreatic beta cell lines. Other committed precursor cells include but are not limited to chondrocytes, osteoblasts, odontoblast, dentin-producing and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, osteoclast and haemopoietic-supportive stroma, cardiac muscle, smooth muscle, skeletal muscle, pericyte, vascular, epithelial, glial, neuronal, astrocyte and oligodendrocyte cells. Precursors include those that specifically can lead to connective tissue particularly including adipose, areolar, osseous, cartilaginous, elastic and fibrous connective tissues.

In another embodiment, the progeny cells are Multipotential Expanded STRO-1$^+$ Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising progenitor cells from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-1$^{bright}$, 3G5$^+$, VCAM-1, THY-1, CD146 and STRO-2.

MEMPS can be distinguished from freshly harvested Stro-1$^{bri}$ cells in that they are positive for the marker STRO-1$^{bri}$ and negative for the marker Alkaline phosphatase (ALP). In contrast, freshly isolated Stro-1$^{bri}$ cells are positive for both STRO-1$^{bri}$ and ALP. In a further embodiment of the present invention, at least 15%, 20%, 30%, 40%, 50%, 60%, 70%, 80%, 90% or 95% of the administered cells have the phenotype STRO-1$^{bri}$, ALP$^-$. In a further embodiment the MEMPS are positive for one or more of the markers Ki67, CD44 and/or CD49c/CD29, VLA-3, α3β1. In yet a further embodiment the MEMPs do not exhibit TERT activity and/or are negative for the marker CD18.

The Stro-1$^{bri}$ cell starting population may be derived from any one or more tissue types including bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing the present invention, separation of cells carrying any given cell surface marker can be effected by a number of different methods, however, certain methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. The separation techniques preferably maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix.

Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

It is preferred that the method for isolating Stro-1$^{bri}$ cells, for example, comprises a first step being a solid phase sorting step utilising for example magnetic activated cell sorting (MACS) recognising high level expression of STRO-1. A second sorting step can then follow, should that be desired, to result in a higher level of precursor cell expression. This second sorting step might involve the use of two or more markers.

The method obtaining Stro-1$^{bri}$ cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable Stro-1$^{bri}$ cell population has been obtained, it may be cultured or expanded by any suitable means to obtain MEMPs.

In one embodiment, the cells are taken from the subject to be treated, cultured in vitro using standard techniques and used to obtain supernatant or soluble factors or expanded cells for administration to the subject as an autologous or allogeneic composition. In an alternative embodiment, cells of one or more of the established human cell lines are used to obtain the supernatant or soluble factors. In another useful embodiment of the invention, cells of a non-human animal (or if the patient is not a human, from another species) are used to obtain supernatant or soluble factors.

The invention can be practised using cells from any non-human animal species, including but not limited to non-human primate cells, ungulate, canine, feline, lagomorph, rodent, avian, and fish cells. Primate cells with which the invention may be performed include but are not limited to cells of chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Examples of lagomorph species with which the invention may be performed include domesticated rabbits, jack rabbits, hares, cottontails, snowshoe rabbits, and pikas. Chickens (*Gallus gallus*) are an example of an avian species with which the invention may be performed.

Cells useful for the methods of the invention may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.).

Genetically-Modified Cells

In one embodiment, the Stro-1$^{bri}$ cells and/or progeny cells thereof are genetically modified, e.g., to express and/or secrete a protein of interest, e.g., a protein providing a therapeutic and/or prophylactic benefit, e.g., insulin, glucagon, somatostatin, trypsinogen, chymotrypsinogen, elastase, carboxypeptidase, pancreatic lipase or amylase or a polypeptide associated with or causative of enhanced angiogenesis or a polypeptide associated with differentiation of a cell into a pancreatic cell or a vascular cell.

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply mutatis mutandis to the present embodiment of the invention.

In one embodiment, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present invention, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the invention will be apparent to the skilled artisan and are described, for example, in Ausubel et al (In: Current Protocols in Molecular Biology, Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for the method of the present invention in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Invitrogen Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al., *J Virol.* 56:2731-2739 (1992); Johann et al, *J Virol.* 65:1635-1640 (1992); Sommerfelt et al, *Virol.* 76:58-59 (1990); Wilson et al, *J. Virol.* 63:274-2318 (1989); Miller et al., *J. Virol.* 65:2220-2224 (1991); PCT/US94/05700; Miller and Rosman *BioTechniques* 7:980-990, 1989; Miller, A. D. *Human Gene Therapy* 7:5-14, 1990; Scarpa et al *Virology* 75:849-852, 1991; Burns et al. *Proc. Natl. Acad. Sci USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al. *Molec. Cell. Biol.* 5:3988-3996, 1988; Vincent et al. (1990) Vaccines 90 (Cold Spring Harbor Laboratory Press); Carter *Current Opinion in Biotechnology* 5:533-539, 1992; Muzyczka. *Current Topics in Microbiol, and Immunol.* 158:97-129, 1992; Kotin, Human Gene Therapy 5:793-801, 1994; Shelling and Smith *Gene Therapy* 7:165-169, 1994; and Zhou et al. *J Exp. Med.* 179:1867-1875, 1994.

Additional viral vectors useful for delivering an expression construct of the invention include, for example, those derived from the pox family of viruses, such as vaccinia virus and avian poxvirus or an alphavirus or a conjugate virus vector (e.g. that described in Fisher-Hoch et al., *Proc. Natl Acad. Sci. USA* 56:317-321, 1989).

In a further embodiment, the progenitor cells are a population of cells enriched for Stro-3$^{bri}$, or homogeonous Stro-3$^{bri}$ cells, or Stro-3$^{bri}$ progeny cells.

Polysulfated Polysaccharides

The present invention also relates to the use of polysulfated polysaccharide compounds. The polysulfated polysaccharide family can be considered to be any naturally occurring or semi-synthetic/synthetic polysulfated polysaccharide or a biologically active fragment thereof that contains two or more sugar rings or carbohydrate structures to which one or more sulfate ester groups are covalently attached as exemplified by heparin and pentosan polysulfate.

Examples of polysulfated polysaccharides falling within the scope of the present invention are naturally occurring high molecular weight heparin, low molecular weight heparins, heparan sulfate, pentosan polysulfate, chondroitin polysulfate, chitosan polysulfate, dermatan polysulfate sulodexide, dextran polysulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

A specific list of polysulfated polysaccharides are pentosan polysulfate, calcium pentosan polysulfate, magnesium pentosan polysulfate, sodium pentosan polysulfate, polysulfated chondroitin and dextran polysulfate.

Further examples of the polysaccharides suitable for the present invention include polysulfated polysaccharides, polysulfated dextran, polysulfated cyclodextran, polysulfated chondroitin, and pentosan polysulfate as its alkali metal or alkaline earth metal salt, for example its calcium or sodium salt, transition metals such as copper and zinc and noble metals such as platinum. Further examples are polysulfated polysaccharide derivatives of homopolysaccharides or heteropolysaccharides, which can be linear or branched. The sugars may come from but are not limited to pentoses or hexoses such as galactose, mannose, glucose, rhanose, fructose, sorbose, xylose, D-arabinose, ribose, L-arabinose, glucuronic acid and their derivatives.

The present invention also encompasses biologically active molecular fragments of polysulfated polysaccharides or analogues or derivatives of polysulfated polysaccharides.

One polysulfated polysaccharide is pentosan polysulfate (PPS). The basic structure of PPS consists of pentoses, i. e. (1+4) linked beta-D-xylopyranose units containing glucuronic acid groups at statistically every 10th unit.

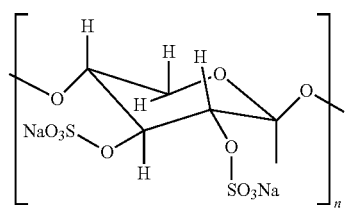

Shown below is the structural formula of pentosan polysulfate (PPS) isolated from beechwood hemicellulose (*Fagus silvatica*). This formula shows that the linear xylan (pentosan) backbone of pentosan polysulfate contains on average one 4-O-methyl-glucuronate side chain linked to the 2-position on every tenth xylose (pentose) ring.

The calcium and magnesium derivatives of PPS (CaPPS or MgPPS) is when R=SO$_3$—Ca+1/2 or Mg$^+$1/2. The sodium derivative is when R=SO$_3$—Na.

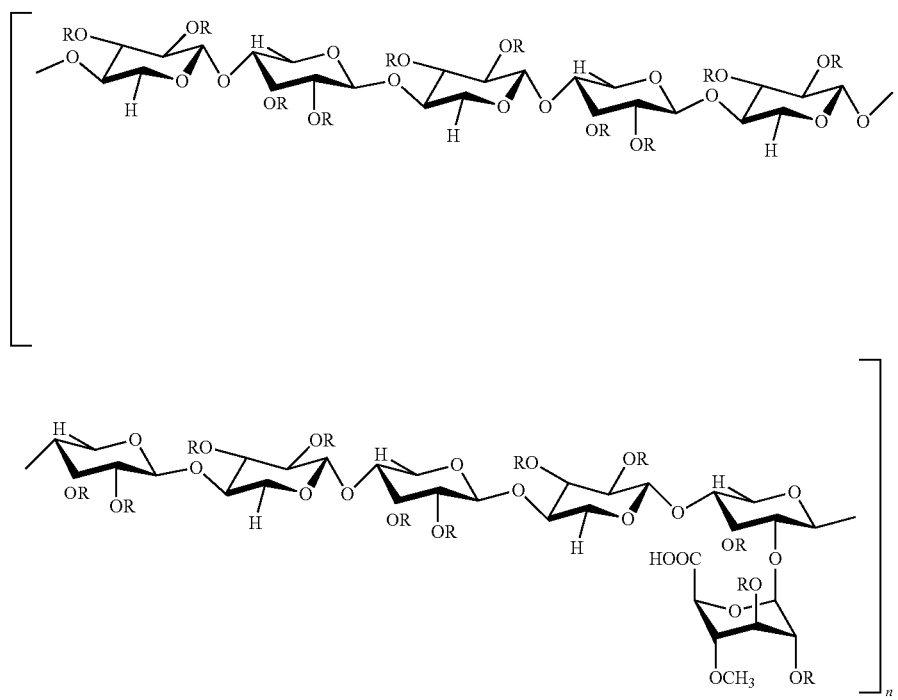

Pentosan polysulfate as its calcium or sodium salt has an average molecular weight of about 5700 Daltons and a sulphur content of about 16%. This compound has been known since the early 1960s to be a synthetic heparinoid and an anti-thrombotic agent.

The particular complexing ions may be selected from the group consisting of the alkali metals, e. g. $Na^+$, and $K^+$, alkaline earth metals, e. g. $Ca^{2+}$, $Zn^{2+}$, $Mg^{2+}$, $Ba^{2+}$, as well as $Ag^+$, $Au^+$, $Pb^{2+}$, $Cu^+$, $Au^{2+}$, $Pd^{2+}$, $Pd^{4+}$, $Pt^{4+}$, $Pt^{2+}$, trivalent metal ions, and quaternary ammonium compound complexes. Examples of the latter compounds are pyridinium chloride, tetraalkyl ammonium chloride, choline chloride, cetylpyridinium chloride, N-cetyl-N, N, N-trialkylammonium chloride or their derivatives. In one particular embodiment, the calcium complex is used.

Preparation of the polysulfate polysaccharide-metal complexes is described in detail in U.S. Pat. No. 5,668,116, the entire disclosure of which is incorporated herein by reference.

Further information relating to polysulfate polysaccharides and PPS can be found in WO02/41901, the entire disclosure of which is incorporated herein by reference. Further information can also be found in Semin Arthritis Rheum. 1999 February; 28(4):211-67 Ghosh—The pathobiology of osteoarthritis and the rationale for the use of pentosan polysulfate for its treatment, the entire disclosure of which is incorporated herein by reference.

In one embodiment, the polysulfated polysaccharide is pentosan polysulfate sodium. An example of this is SP54, manufactured by Bene Pharmachem, Germany, which is a polysaccharide, esterified with sulphuric acid, more specifically a pentosan polysulfate sodium. The semisynthetic production of pentosan polysulfate sodium assures consistent and reproducible manufacturing with a defined range of molecular weight (4000 to 6000 daltons).

A further polysulfated polysaccharide is polysulfated chondroitin. An example of this is Arteparon®. (trade mark of Luitpold-Werk) which consists predominantly of polysulfated chondroitin. It has been used as an antiarthritic drug. More specifically, it is a heterogeneous semi-synthetic glycosaminoglycan polysulfate in which the predominant (about 93%) disaccharide repeating unit is hexuronic acid glycosidically linked to galactosamine. Approximately four of the free hydroxyl groups of the disaccharide repeating unit of Arteparon are esterified by sulfate groups to give a sulphur content of about 13.0% by weight. The commercial preparation has a molecular weight of about 10,000 Daltons.

Preparation of the polysulfate polysaccharide-metal complexes is described in detail in U.S. Pat. No. 5,668,116, the entire disclosure of which is incorporated herein by reference.

Further information relating to polysulfate polysaccharides and PPS can be found in WO02/41901, the entire disclosure of which is incorporated herein by reference. Further information can be found in Semin Arthritis Rheum. 1999 February; 28(4):211-67 Ghosh—The pathobiology of osteoarthritis and the rationale for the use of pentosan polysulfate for its treatment, the entire disclosure of which is incorporated herein by reference.

In particular, the methods of manufacture, isolation and purification together with suitable carriers compositions and formulations are incorporated into the present application.

Further information can also be found in Ghosh P, Edelman J, March L and Smith M. Effects of pentosan polysulfate in osteoarthritis of the knee: A randomised, double blind, placebo-controlled pilot study. Current Therapeutic Research, 2005, 66: 552-571, and which provides information on an OA clinical study using PPS given by intramuscular injection. The information on PPS, and the methods used in the trial including the dosage regimes and administration methods are hereby incorporated by reference into the present application.

Non-Collagenous NC4 Domain of Alpha IX Collagen

According to a further embodiment, the polypeptide chosen is a non-collagenous NC4 domain of alpha IX collagen or a biologically active molecular fragment thereof. Specific information about suitable NC4 domain polypeptides can be found in International application PCT/AU2004/000788, the contents of which are incorporated in their entirety.

In particular, PCT/AU2004/000788 discloses a number of polypeptide and their sequences that can be used in the present invention together with ways of expressing and purifying the polypeptides. Thus, PCT/AU2004/000788 includes examples of suitable NC4 domain polypeptides and ways of making them which are specifically incorporated into the present specification. In particular, the amino acid sequences as set out in page 7 lines 24 to page 8 line 6 together with the sequences as set out in FIGS. 1-7 are specifically incorporated into the present application. Furthermore, the methods of recovering polypeptides as set out in page 9 line 10 to page 10 line 36 are specifically incorporated into the present application. The autolysis techniques set out in the detailed description from page 15 together with the separating and recovery steps set out in the detailed description from page 18 and specifically the polypeptides as set out on pages 20-24 are incorporated into the present invention. Finally, the partial amino acid sequence of FIG. 7 is incorporated into the present application.

As said above, the NC4 domain is discussed in PCT/AU2004/000788. It includes the complete amino acid sequence predicted from the gene sequence and obtained by expression in *E. coli* (see Table 1).

However, it should be noted that the protein products obtained by expression using *K. lactis* consisted of the full length human NC4 plus a truncated form (MW=24 kDa), with both forms being glycosylated, these are also included in Table 1 and there preparation and ID are described in the methods section. Both the *E. coli* and *K. lactis* expressed proteins were evaluated in animal models and in vitro assays and may be identified by the codes AWR-01 and PBA-1200P respectively. The progenitor cells used in these experiments was the mouse ATDC5 which is commercially available as discussed in the methods section. The differentiated cells used included: chondrocytes from human joint cartilage, normal ovine and porcine cartilage and chondrocytes and synovial fibroblasts derived from synovial tissue from OA patients undergoing total joint replacement surgery.

In particular, the following sequences also define polypeptides for use in the present application.

TABLE 1

Amino acid sequences of interest
but shown without N or O glycosylation 1) hNC4: (Full length human NC4 without signal peptide)
SEQ ID NO: 1

```
         10         20         30         40         50
AVKRRPRFPV NSNSNGGNEL CPKIRIGQDD LPGFDLISQF QVDKAASRRA 60         70         80         90        100
IQRVVGSATL QVAYKLGNNV DFRIPTRNLY PSGLPEEYSF LTTFRMTGST
```

TABLE 1-continued

Amino acid sequences of interest but shown without N or O glycosylation

```
         110        120        130        140        150
     LKKNWNIWQI QDSSGKEQVG IKINGQTQSV VFSYKGLDGS LQTAAFSNLS 160        170        180        190        200
     SLFDSQWHKI MIGVERSSAT LFVDCNRIES LPIKPRGPID IDGFAVLGKL 210        220        230        240
     ADNPQVSVPF ELQWMLIHCD PLRPRRETCH ELPARITPSQ TTDER
```

2) Truncated hNC4 (residues 6-224) obtained during expression from *K. lactis* cultures by action of putative by proline endopeptidase:

SEQ ID NO: 2

```
          10         20         30         40         50
     RFPVNSNSNG GNELCPKIRI GQDDLPGFDL ISQFQVDKAA SRRAIQRVVG 60         70         80         90        100
     SATLQVAYKL GNNVDFRIPT RNLYPSGLPE EYSFLTTFRM TGSTLKKNWN 110        120        130        140        150
     IWQIQDSSGK EQVGIKINGQ TQSVVFSYKG LDGSLQTAAF SNLSSLFDSQ 160        170        180        190        200
     WHKIMIGVER SSATLFVDCN RIESLPIKPR GPIDIDGFAV LGKLADNPQV

210
     SVPFELQWML IHCDPLRP
```

3) Sequences underlined in bolded red which were identified by proteomics and described in Patent Application PCT/AU2004/000788 (full-length sequence disclosed as SEQ ID NO: 94 and bolded and underlined sequences disclosed as SEQ ID NOS 95-103, respectively, in order of appearance)

1 *Met Lys Thr Cys Trp Lys Ile Pro Val Phe Phe Val Cys Ser*

16 *Phe Leu Glu Pro Trp Ala Ser Ala*

23 Ala Val Lys Arg Arg Pro Arg

31 Phe Pro Val Asn Ser Asn Ser Asn Gly Gly Asn Glu Leu Cys Pro

46 Lys Ile Arg Ile Gly Gln Asp Asp Leu Pro Gly Phe Asp Leu Ile

61 Ser Gln Phe Gln Val Asp Lys Ala Ala Ser Arg Arg Ala Ile Gln

76 Arg Val Val Gly Ser Ala Thr Leu Gln Val Ala Tyr Lys Leu Gly

91 Asn Asn Val Asp Phe Arg Ile Pro Thr Arg Asn Leu Tyr Pro Ser

106 Gly Leu Pro Glu Glu Tyr Ser Phe Leu Thr Thr Phe Arg Met Thr

121 Gly Ser Thr Leu Lys Lys Asn Trp Asn Ile Trp Gln Ile Gln Asp

136 Ser Ser Gly Lys Glu Gln Val Gly Ile Lys Ile Asn Gly Gln Thr

151 Gln Ser Val Val Phe Ser Tyr Lys Gly Leu Asp Gly Ser Leu Gln

166 Thr Ala Ala Phe Ser Asn Leu Ser Ser Leu Phe Asp Ser Gln Trp

181 His Lys Ile Met Ile Gly Val Glu Arg Ser Ser Ala Thr Leu Phe

196 Val Asp Cys Asn Arg Ile Glu Ser Leu Pro Ile Lys Pro Arg Gly

211 Pro Ile Asp Ile Asp Gly Phe Ala Val Leu Gly Lys Leu Ala Asp

226 Asn Pro Gln Val Ser Val Pro Phe Glu Leu Gln Trp Met Leu Ile

241 His Cys Asp Pro Leu Arg Pro Arg Arg Glu Thr Cys His Glu Leu

256 Pro Ala Arg Ile Thr Pro Ser Gln Thr Thr Asp Glu Arg 268

A sequence composition between bovine human, murine and chick NC4 sequences is provided in FIG. 37. Conserved sequences are as follows:

```
K/QSVSN/A/EFSYKG          SEQ ID NO: 3

KI/LMIG/SVER/TS/T         SEQ ID NO: 4

KLGNNVDFRI                SEQ ID NO: 5

R/KI/VES/TLP/NIKPR/KG     SEQ ID NO: 6

KH/N/YWS/N/TIWQIQDS/AGK/R SEQ ID NO: 7

K/QSVS/VFSYKG             SEQ ID NO: 8

KIMIGVERTS                SEQ ID NO: 9

RIESLPIKPRG               SEQ ID NO: 10

KH/NWS/NIWQIQDSGK         SEQ ID NO: 11

RIGQDDLPGFDLISQFQI/VDKA   SEQ ID NO: 12

RH/NLYPN/SGLPEEYSFLTTFR   SEQ ID NO: 13

FSNLP/SSLFDSQWHKI         SEQ ID NO: 14

RSSATLFVDCNRI             SEQ ID NO: 15

KSVSFSYKG                 SEQ ID NO: 16

KIMIGVERS                 SEQ ID NO: 17

KLGNNVDFRI                SEQ ID NO: 18

RIESLPIKPRG               SEQ ID NO: 19

KHWSIWQIQDSSGK            SEQ ID NO: 20

RIGQDDLPGFDLISQFQIDKA     SEQ ID NO: 21

RHLYPNGLPEEYSFLTTFRM      SEQ ID NO: 22

FSNLPSLFDSQWHKI           SEQ ID NO: 23

RSSATLFVDCNRI             SEQ ID NO: 24
```

Cryopreservation

There are various techniques to cryopreserve progenitor cells known to the person skilled in the art. One example procedure is as follows:

Examination:

Prior to freezing, the cells should be maintained in an actively growing state to insure maximum health and a good recovery. Ideally, the culture medium should be changed the previous day. Using an inverted microscope, quickly check the general appearance of the culture. Look for signs of microbial contamination. It is also important to examine the culture with the unaided eye to look for small fungal colonies that may be floating at the medium-air interface and thus not visible through the microscope. It is best if the cultures are maintained antibiotic-free for at least one week prior to freezing to help uncover any cryptic (hidden) culture contaminants.

Cell Harvesting and Freezing:

Treat the cells gently during harvesting since it is very difficult for cells damaged during harvesting to survive the additional damage that occurs during the freezing and thawing processes. You should be able to obtain up to $1.5 \times 10^7$ cells from a near confluent T-75 flask (depending on cell type and degree of confluency). This should be enough cells to set up at least several vials at $2 \times 10^6$ cells/vial.

1. Using a sterile pipette, remove and discard the old culture medium.

2. For a T-75 flask, rinse the cell monolayer with 5 mL of calcium- and magnesium-free phosphate buffered saline (CMF-PBS) to remove all traces of foetal bovine serum.

3. Add 4 to 5 mL of the trypsin solution (in CMF-PBS) to the flask and allow cells to incubate for at least one minute. (Prewarming of the enzyme 4 solution will decrease the exposure period.) Withdraw about 3 mL of the trypsin solution and allow the cells to round up and loosen.

4. Check the progress of the enzyme treatment every few minutes on an inverted phase contrast microscope. Once all of the cells have rounded up, gently tap the flask to detach them from the plastic surface. Then add 5 mL of growth medium to the cell suspension and, using the same pipette, vigorously wash any remaining cells from the bottom of the culture vessel.

5. Collect the suspended cells in a 15 mL centrifuge tube and place on ice. Take a sample for counting and then spin at 100×g for 5 minutes to obtain a cell pellet. While the cells are spinning, do a viable cell count (with the trypan blue solution) and calculate the number of cells/mL and the total cell number.

6. Remove the supernatant from the centrifuged cells and resuspend the cell pellet in enough of the cryoprotective medium containing 10% DMSO (DMSO is most often used at a final concentration of 5 to 15% to give a final cell concentration of 1 to $2 \times 106$ cells/mL.

7. Label the appropriate number of cryogenic vials with the cell line, and the date. Then add 1.5 to 1.8 mL of the DMSO containing cell suspension to each of the vials and seal.

8. Place the vials in the controlled rate freezer overnight. After 24 hours, the cells should be transferred to a liquid nitrogen freezer for permanent storage.

9. Record the appropriate information about the cells in your cell repository records. Fully detail in these records the culture's storage conditions, including all of the following information: culture identity, passage or population doubling level, date frozen, freezing medium and method used, number of cells per vial, total number of vials initially frozen and the number remaining, their locations, their expected viability and results of all quality control tests performed (sterility, mycoplasma, species, karyotype, etc.). Additional culture information, especially its origin, history, growth parameters, special characteristics and applications, is also helpful and should be included whenever possible.

Cell Thawing and Recovery:

1. Using appropriate safety equipment, remove the vial from its storage location and carefully check both the label and storage record to ensure that it is the correct culture.

Place the vessel in warm water, agitating gently until completely thawed. Rapid thawing (60 to 90 seconds at 37° C.) provides the best recovery for most cell cultures; it reduces or prevents the formation of damaging ice crystals within cells during rehydration.

2. Since some cryoprotective agents may damage cells upon prolonged exposure, remove the agents as quickly and gently as possible. Several approaches are used depending on both the cryoprotective agents and characteristics of the cells:

a) Most cells recover normally if they have the cryoprotective agent removed by a medium change within 6 to 8 hours of thawing. Transfer the contents of the ampule or vial to a T-75 flask or other suitable vessel containing 15 to 20 mL of culture medium and incubate normally. As soon as a majority of the cells have attached (usually 3 to 4 hours), remove the medium containing the now diluted cryoprotective agent and replace with fresh medium.

b) For cells that are sensitive to cryoprotective agents, removing the old medium is easily accomplished by gentle centrifugation. Transfer the contents of the vial or ampule to a 15 mL centrifuge tube containing 10 mL of fresh medium and spin for 5 minutes at 100×g. Discard the supernatant containing the cryoprotective agent and resuspend the cell pellet in fresh medium. Then transfer the cell suspension to a suitable culture vessel and incubate normally.

Support Matrix

Recent advances in biology and material science have brought tissue engineering to the forefront of new cartilage repair techniques. The combination of autologous cells, specifically designed scaffolds, bioreactors, mechanical stimulations and growth factors offer promising avenues for carilage tissue regeneration.

Bioscaffolds Mimic Extracellular Matrix.

Current tissue-engineering strategies provide scaffolds derived from both synthetic (e.g., polyglycolic acid) and naturally-derived (e.g., collagen) materials to form the cell-scaffold construct. Currently available tissue scaffold products include small intestine submucosa (Restore™, porcine SIS, DePuy Orthopaedics), (CuffPatch™, porcine SIS, Organogenesis), (SIS; Cook Biotech, Inc.), reformulated collagen scaffolds (3D Collagen Composite, BD Biosciences), acellular human dermal collagen matrices (Graftjacket®, Wright Medical Technologies), fetal bovine dermis (TissueMend®, Stryker), and synthetic polymer scaffolds, primarily polyesters (e.g. PGA, PCL, and PLA).

Tissue engineered scaffolds that have recently been described including collagen scaffolds, chrondrocyte seeded scaffolds, articular chondrocyte seeded type II collagen-GAG scaffolds [Vickers et al, Tissue Eng. 2006 May; 12(5): 1345-55] and composite scaffolds comprising polyethylene oxide (PEO) and chitosan [Kuo Y C et al; J. Biomed Mater Res A. 2008 Nov. 3] An alternate form described by Nettles D L et al., [Tissue Eng part A 2008 July; 14(7): 1133-40] is an injectable cross-linkable elastin-like polypeptide (ELP) gel for application to cartilage matrix repair.

The choice of matrix material is based on biocompatibility, biodegradability, mechanical properties, cosmetic appearance and interface properties. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In one embodiment, the scaffold is derived from a synthetic material. In another embodiment the scaffold is derived from naturally derived-materials. Alternatively, the sscaffold is a combination of synthetic and naturally derived materials.

In one embodiment, and as described in the examples, the support matrix is a collagen sponge. The composition of the invention including the cells, pentosan polysulfate optionally in combination with a NC4 polypeptidecan be implanted or infused or perfused into the sponge. Since sponges can be delicate to implant, the sponge is optionally inserted into a resorbable cage.

Compositions

In all cases, the compositions and formulations as discussed herein are suitable for the polysaccharides and/or polypeptides of the present invention. In particular, the compositions and formulations are suitable for polysulfated polysaccharides, in one embodiment pentosan polysulfate, calcium pentosan polysulfate, magnesium pentosan polysulfate and/or sodium pentosan polysulfated alone. The compositions and formulations are also suitable for combinations of the compounds discussed herein, for example combinations of polysaccharides and/or polypeptides, and in particular combinations of NC4 domain polypeptides and pentosan polysulfate and its salts.

According to the present invention, compositions comprising a polysaccharide and/or polypeptide as disclosed herein, particularly polysulfated polysaccharides optionally with NC4 domain, in one embodiment pentosan polysulfate, calcium pentosan polysulfate and/or sodium pentosan polysulfate or a fragment or truncated form are suitable for human or animal usage in human and veterinary medicine and will typically comprise any one or more of a pharmaceutically acceptable diluent, carrier or excipient. Acceptable carriers or diluents for therapeutic use are well known in the pharmaceutical art, and are described for example in *Remington's Pharmaceutical Sciences* Mack Publishing Co. (A. R. Gennaro edit. 1985). The choice of pharmaceutical carrier excipient or diluent can be selected with regard to the intended route of administration and standard pharmaceutical practice. The compositions may comprise as, or in addition to, the carrier, excipient or diluent, any suitable binder, lubricant, suspending agent (liposomes), coating agent, or solubilising agent.

It is well known in the art that there may be different composition/formulation requirements dependent on the different delivery systems. For example, polysaccharides and/or proteins comprising a NC4 domain can be dissolved in saline. Alternatively these compounds can be made up in a solution provided with a two part liquid-powder that is mixed before use.

Implantable (subcutaneous) slow release capsules are often used for contraceptives like Implanon™ or Depo-Provera™ injections and would be useful for administration of a composition of the present invention.

In another example, the composition of the present invention may be formulated to be delivered using an implanted mini-pump wherein the composition is typically administered by continuous infusion into the desired location.

In an alternate embodiment, compositions of the invention can be injected or otherwise implanted parenterally for example, intravenously, subcutaneously, intra-muscularly, intra-articularly, intra-discally or intra-dermally. In a further embodiment the formulation is administered subcutaneously, intra-dermally or intra-articularly.

Subcutaneous and intra-dermal formulations can also contain one or more additional agents such as for example soft-tissue filler substances, lidocaine (local anaesthetic), matrix metalloproteinase inhibitors, antioxidants and anti-inflammatory agents (corticosteroids).

Various formulations for intra-dermal delivery of a drug may comprise one or more of the following ingredients: albumin, buffer, buffered saline, buffered salt solution, and anaesthetic (preferably local).

The present invention extends to combination therapies for use in the treatment of the diseases discussed herein. Particularly, in one example, the present invention extends to the use of a polysulfated polysaccharide and a polypeptide for use in the treatment of various degenerative conditions. It should be understood that these agents can be administered at the same time or a different time. Thus the combination therapy may comprise the active agents being administered at the same time either in a single formulation or in multiple formulations administered at the same or different times. Equally, the combination therapy may comprise the active agents being administered in different formulations at different times. The formulations could be administered sequentially and may be separated by a period of time including hours, days, weeks and months.

Example formulations suitable for injection into an animal, for example intra-dermally, sub-cutaneously or intra-muscularly include:

1) A polysulfated polysaccharides, in one embodiment pentosan polysulfate, calcium pentosan polysulfate and/or sodium pentosan polysulfate together with progenitor cells dissolved in sterile water.

2) A polysulfated polysaccharides, in one embodiment pentosan polysulfate, calcium pentosan polysulfate and/or sodium pentosan polysulfated, together with progenitor cells, dissolved in 0.9% sterile saline (150 mM NaCl); +/−human albumin (0.01%-0.5%); +/−local anaesthetic; examples e.g. bupivacaine hydrochloride (1.25-5 mg/ml); +/−adrenaline acid tartrate (0.0045-0.0091 mg/ml); +/−lidocaine (0.5-2%); +/−epinephrine (1:100,000-1:200,000).

3) A polysulfated polysaccharides, in one embodiment pentosan polysulfate, calcium pentosan polysulfate and/or sodium pentosan polysulfate, together with progenitor cells, dissolved in phosphate buffered saline; +/−human albumin (0.01-0.5%); +/−local anaesthetic; 137 mM NaCl; 2.7 mM KCl; 10 mM phosphate buffer; 150 mM NaCl; 150 mM $NaH_2PO_4/Na_2HPO_4$.

4) A polysulfated polysaccharides, in one embodiment pentosan polysulfate, calcium pentosan polysulfate and/or sodium pentosan polysulfated, together with progenitor cells, dissolved in phosphate-citrate buffer (50 mM)+/−sodium perborate (0.03%); +/−human albumin (0.01-0.5%); +/−local anaesthetics.

5) A polysulfated polysaccharides, in one embodiment pentosan polysulfate, calcium pentosan polysulfate and/or sodium pentosan polysulfate, together with progenitor cells, dissolved in a solution of sterile water containing carboxymethylcellulose (2.7%) and mannitol.

6) A polysulfated polysaccharides, in one embodiment pentosan polysulfate, calcium pentosan polysulfate and/or sodium pentosan polysulfate, together with progenitor cells, incorporated into biocompatible polyalkymide hydrogels (eg Bio-Alcamid® made by Polymekon S.r.l. (Milan, Italy).

7) A polysulfated polysaccharides, in one embodiment pentosan polysulfate, calcium pentosan polysulfate and/or sodium pentosan polysulfate, together with progenitor cells, incorporated into hylan B gel (e.g. Hylaform® Plus).

8) A polysulfated polysaccharides, in one embodiment pentosan polysulfate, calcium pentosan polysulfate and/or sodium pentosan polysulfate, together with progenitor cells, incorporated into stabilised hyaluronic acid gel (e.g. Restylane®).

9) A polysulfated polysaccharides, in one embodiment pentosan polysulfate, calcium pentosan polysulfate and/or sodium pentosan polysulfate, together with progenitor cells, incorporated into poly-L-lactic acid solution (e.g. Sculptra®).

10) A polysulfated polysaccharides, in one embodiment pentosan polysulfate, calcium pentosan polysulfate and/or sodium pentosan polysulfate, together with progenitor cells, incorporated dissolved in a solution of Krebs-Ringer's solution containing NaCl 118.1 mM; KCl 3.4 mM; $CaCl_2$ 2.5 mM; $MgSO_4$ 0.8 mM; $KH_2PO_4$ 1.2 m; $NaHCO_3$ 25.0 mM; Glucose 11.1 mM.

Formulations of the present invention also further comprise any one or more of the following:

a steroidal anti-inflammatory drug (corticosteroid), a calcineurin inhibitor (eg pimecrolimus, tacrolimus), a phosphodiesterase inhibitors, a anti-histamine, a anti-microbial agent, a antibiotic, a antibacterial agent, a ceremide, a growth factor (eg transforming growth factors β1-3, platelet derived growth factor, fibroblast growth factor, insulin-like growth factors I & II, epidermal growth factor, keratinocyte growth factor, nerve growth factor), a mitogenic agent, a matrix metalloproteinase inhibitor (eg TIMP's, Batimastat, Marimastat, and matlystatin B), a protease inhibitor, a ECM protein, tretinoin (Vitamin A), a antioxidant (vitamins E and C), a plant cytokinin (kinerase), a copper-peptide complexes as well as numerous plant, animal and mineral extracts (ie coal tar extract).

Specific formulations of the present invention comprise a combination with a steroidal anti-inflammatory drug. Another composition comprises a calcineurin inhibitor. Another composition comprises an anti-histamine. Another composition comprises an anti-microbial agent. Another composition comprises a growth factor. Another composition comprises a protease inhibitor.

Preparation of Compositions for Administration

Liposomes

Encapsulation of proteins within liposomes are detailed for example in U.S. Pat. Nos. 5,662,931; 5,853,755; 4,485,054; 5,780,054; 5,653,974; 6,019,999; 6,027,726; 5,739,273; 5,264,221; 5,413,804; 5,374,715.

Polymers

The polysaccharides and/or polypeptides of the present invention, can be encapsulated within biodegradable synthetic polymers (or derivatives) for controlled release. These polymers (and derivatives) include for example: Poly(esters); examples are poly(ε-caprolactone) PCL, poly(glycolic acid) PGA, poly(L-lactic acid) PLA, poly(ethylene glycol) PEG, poly(ethylene oxide) PEO. Poly(ester) derivatives include Poly(ester) copolymers, Poly(ortho esters). Poly(ester) copolymers; examples are poly(lactic acid-co-glycolic acid) PLGA, poly(D-lactic acid) PDLA, poly(L-lactic acid) PLLA, PLA-PEG, diblock PLA/PEG, triblock PLA/PEG/PLA. Poly(ortho esters); examples are 3,9-diethylidene-2,4,8,10-tetraoxaspiro[5.5]undecane(DETOSU)- based poly(orthoesters). Poly(anhydrides); examples are sebacic acid (SA), p-(carboxyphenoxy)propane (CPP), p-(carboxyphenoxy)hexane (CPH), SA/CPP copolymers, poly(fatty acid dimer-sebacic acid), poly(anhydride-imides), poly(anhydride-esters). Poly(amides); examples are poly (amino acids), poly(glutamic acid), poly(aspartic acid), poly (lactic acid-co-lysine)PLAL, poly [N-(3-hydroxypropyl)-L-glutamine], poly(iminocarbonates), tyrosine-derived poly (carbonates). Phosphorus-containing polymers; ie poly (phosphazenes), poly(dichlorophosphazenes), poly (organophosphazenes), poly [bis(carboxylatophenoxy)-phosphazene], poly(phosphoesters), poly(urethanes), a hyaluronan carrier.

Coupling

Polypeptide(s) and/or polysaccharide(s) can be coupled to a collagen matrix for administration. Collagen matrix can release a coupled drug at a constant effective concentration. Accordingly, collagen and other ECM protein matrices can effectively be used to administer polypeptide(s) and/or polysaccharide(s) in vivo, for example into a tissue or space in need thereof. In one embodiment the cross-linked collagen matrix is administered subcutaneously.

General

Generally, the present invention relates to and/or uses therapeutically effective amounts and/or prophylactically effective amounts of the compositions discussed herein.

A "therapeutically effective amount" refers to an amount effective, at dosages and for periods of time necessary, to achieve the desired effect.

A "prophylactically effective amount" refers to an amount effective, at dosages and for periods of time necessary, to achieve the desired prophylactic result, such as preventing or inhibiting cell apoptosis or tissue damage.

Polypeptides

Reference herein to "polypeptide" includes single polypeptides, mixtures of polypeptides and also biologically active fragments of polypeptides.

By "substantially purified polypeptide" we mean a polypeptide that has been at least partially separated from the lipids, nucleic acids, other polypeptides, and other contaminating molecules with which it is associated in its native state. In one embodiment, the substantially purified polypeptide is at least 60% free from other components with which they are naturally associated. In a further embodiment, the substantially purified polypeptide is at least 75% free from other components with which they are naturally associated. In a further embodiment, the substantially purified polypeptide is at least 90% free from other components with which they are naturally associated. Furthermore, the term "polypeptide" is used interchangeably herein with the term "protein".

The % identity of a polypeptide is determined by GAP (Needleman and Wunsch, 1970) analysis (GCG program) with a gap creation penalty=5, and a gap extension penalty=0.3. Unless stated otherwise, the query sequence is at least 15 amino acids in length, and the GAP analysis aligns the two sequences over a region of at least 15 amino acids. The query sequence may be at least 50 amino acids in length, and the GAP analysis aligns the two sequences over a region of at least 50 amino acids. The query sequence may at least 100 amino acids in length and the GAP analysis aligns the two sequences over a region of at least 100 amino acids.

With regard to the defined polypeptides/enzymes, it will be appreciated that % identity figures higher than those provided above will encompass embodiments. Thus, where applicable, in light of the minimum % identity figures, the polypeptide may comprises an amino acid sequence which is at least 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the relevant nominated SEQ ID NO.

As used herein, the term "biologically active fragment" refers to a portion of the defined polypeptide which still maintains anti-arthritic or anti-inflammatory activity (whichever is relevant). Such biologically active fragments can readily be determined by serial deletions of the full length protein, and testing the activity of the resulting fragment.

Amino acid sequence mutants/variants of the polypeptides/enzymes defined herein can be prepared by introducing appropriate nucleotide changes into a nucleic acid encoding the polypeptide, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 30 residues, about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active or binding site(s). Other sites of interest are those in which particular residues obtained from various strains or species are identical. These positions may be important for biological activity. These sites, especially those falling within a sequence of at least three other identically conserved sites, may be substituted in a relatively conservative manner. Such conservative substitutions are shown in Table A.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, D-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, D-alanine, fluoro-amino acids, designer amino acids such as D-methyl amino acids, C-methyl amino acids, N-methyl amino acids, and amino acid analogues in general.

TABLE A

| Exemplary substitutions. | |
|---|---|
| Original Residue | Exemplary Substitutions |
| Ala (A) | val; leu; ile; gly |
| Arg (R) | lys |
| Asn (N) | gln; his |
| Asp (D) | glu |
| Cys (C) | ser |

TABLE A-continued

Exemplary substitutions.

| Original Residue | Exemplary Substitutions |
| --- | --- |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides of the present invention can be produced in a variety of ways, including production and recovery of natural proteins, production and recovery of recombinant proteins, and chemical synthesis of the proteins. In one embodiment, an isolated polypeptide of the present invention is produced by culturing a cell capable of expressing the polypeptide under conditions effective to produce the polypeptide, and recovering the polypeptide. One cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Gene Therapy

The polynucleotides and polypeptides may be employed in accordance with the present invention by expression of such polypeptides in treatment modalities often referred to as "gene therapy". Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide useful for the methods of the present invention to transform said cells. Such methods are well-known in the art and their use in the present invention will be apparent from the teachings herein.

Further, cells may be engineered in vivo for expression of a polypeptide in vivo by procedures known in the art. For example, a polynucleotide useful for a method of the present invention may be engineered for expression in a replication defective retroviral vector or adenoviral vector or other vector (for example, poxvirus vectors). The expression construct may then be isolated. A packaging cell is transduced with a plasmid vector containing RNA encoding a polypeptide useful for a method of the present invention, such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors hereinabove-mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In one embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter. Cellular promoters such as eukaryotic cellular promoters including, but not limited to, the histone, RNA polymerase III, and β-actin promoters, can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide useful for a method of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, YCRE, YCRIP, GP+E-86, GP+en-vAm12, and DAN cell lines as described in Miller (1990) Human Gene Therapy, 1:5-14.

The vector may be transduced into the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eukaryotic cells will express the nucleic acid sequence(s) encoding the polypeptide.

Eukaryotic cells which may be transduced include, but are not limited to, mesenchemymal cells, chondrocytes, embryonic stem cells, embryonic carcinoma cells, as well as hematopoietic stem cells, hepatocytes, fibroblasts, myoblasts, keratinocytes, endothelial cells, and bronchial epithelial cells.

Genetic therapies in accordance with the present invention may involve a transient (temporary) presence of the gene therapy polynucleotide in the patient or the permanent introduction of a polynucleotide into the patient.

Genetic therapies, like the direct administration of agents discussed above, in accordance with the present invention may be used alone or in conjunction with other therapeutic modalities.

Preparation and Administration of Pharmaceutical Compositions

The amount of polysaccharide optionally with a polypeptide to be administered may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier.

It will be appreciated that the polysaccharide optionally with a polypeptide may be administered in the form of a composition comprising a pharmaceutically acceptable carrier or excipient.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the polysaccharide and/or polypeptide may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The polysaccharide optionally with a polypeptide may be administered in combination with an appropriate matrix, for instance, for providing a surface for bone, cartilage, muscle, nerve, epidermis and/or other connective tissue growth. The matrix may be in the form of traditional matrix biomaterials. The matrix may provide slow release of the cells, supernatant or soluble factors.

The choice of matrix material is based on biocompatibility, biodegradability, mechanical properties, cosmetic appearance and interface properties. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

Compositions of the invention may be prepared from one or more polysaccharide and/or polypeptide. Additional polysaccharide and/or polypeptide fragments or peptides can be identified by routine experimentation in light of the present specification, claims and figures. A method for identifying peptide fragments having stimulatory activity is described, for example, in U.S. Pat. No. 5,399,342.

The pharmaceutical compositions may be for human or animal usage in human and veterinary medicine and will typically comprise any one or more of a pharmaceutically acceptable diluent, carrier or excipient. Acceptable carriers or diluents for therapeutic use are well known in the pharmaceutical art, and are described for example in *Remington's Pharmaceutical Sciences* Mack Publishing Co. (A. R. Gennaro edit. 1985). The choice of pharmaceutical carrier excipient or diluent can be selected with regard to the intended route of administration and standard pharmaceutical practice. The pharmaceutical compositions may comprise as, or in addition to, the carrier, excipient or diluent, any suitable binder, lubricant, suspending agent, coating agent, or solubilising agent.

It is well known in the art that there may be different composition/formulation requirements dependant on the different delivery systems.

According to the present invention non-invasive formulations are also encompassed. For example, while the progenitor cells are likely to be administered parerentally, eg intra-articularly, the polysulfated polysaccharide can be administered by inhalation, orally or intranasally, in the form of suppository or pessary, topically in the form of a lotion, solution, cream, ointment, or dusting powder, by use of a skin patch, orally in the form of tablets containing excipients such as starch or lactose, or in capsules, chewables or ovules either alone or in admixture with excipients, or in the form of elixirs, solutions, syrups or suspensions containing flavouring or colouring agents.

For buccal or sublingual administrations, the compositions may be administered for example in the form of tablets or lozenges which can be formulated in a conventional manner.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, particularly 25% to 70%. Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Intranasal formulations are described and administration of larthrytic collagen type II and larthrytic collagen type IX are described for example in Lu et al (1999) Different therapeutic and bystander effects by intranasal administration of homologous type II and type IX collagens on the collagen-induced arthritis and pristane-induced arthritis in rats, *Clinical Immunology* Vol 90 pp 119-127 (1999).

In another example, the pharmaceutical composition of the present invention may be formulated to be delivered using a mini-pump or by a mucosal route, for example, as a nasal spray or aerosol for inhalation or ingestible solution.

Where the agent is to be delivered mucosally through the gastro-intestinal mucosa, it should be able to remain stable during transit through the gastro-intestinal tract; for example, it should be resistant to proteolytic degradation, stable antacid, pH and resistant to the detergent effects of bile.

In one embodiment, the polysulfated polysaccharides of the invention are administered by a non-invasive route. In a further embodiment, the non-invasive route comprises oral administration, or enteral administration, nasal administration or by inhalation.

In an alternate embodiment, compositions of the invention can be injected parenterally for example, intravenously, intramuscularly or subcutaneously.

For parenteral administration, the compositions may be best used in the form of a sterile aqueous solution which may contain other substances, for example enough salts or monosaccharides to make the solution isotonic with blood. The preparation may also be emulsified, or encapsulated in liposomes.

After formulation, the immuno-protective composition may be incorporated into a sterile container which is then sealed and stored at a low temperature, for example 4° C., or it may be freeze-dried. Lyophilisation permits long-term storage in a stabilised form.

In one embodiment of the present invention progenitor, particular the chondroprogenitor and even more particularly the Stro-$1^{bri}$ cells and/or progeny cells thereof are administered in the form of a composition. In one embodiment, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for this invention include those conventionally used, e.g., water, saline, aqueous dextrose, lactose, Ringer's solution, a buffered solution, hyaluronan and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. In a further example, such a media composition does not induce any adverse effects in a subject to whom it is administered.

Preferred carriers and excipients do not adversely affect the viability of a cell.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the invention may be produced as a liquid for direct application to the blood stream or into a tissue or a region surrounding or adjacent to a tissue, e.g., by injection.

Progenitor, particular the chondroprogenitor and even more particularly Stro-$1^{bri}$ cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the invention. Scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. *J. Ped. Surg.* 23:3-9 1988; Cima, et al. *Biotechnol. Bioeng.* 38:145 1991; Vacanti, et al. *Plast. Reconstr. Surg.* 88:753-9 1991; or synthetic polymers such as polyanhydrides, polyorthoesters, and polylactic acid.

In another example, the cells may be administered in a gel scaffold (such as Gelfoam from Upjohn Company).

The cellular compositions useful for the present invention may be administered alone or as admixtures with other cells.

Cells that may be administered in conjunction with the compositions of the present invention include, but are not limited to, other multipotent or pluripotent cells or stem cells, or bone marrow cells. The cells of different types may be admixed with a composition of the invention immediately or shortly prior to administration, or they may be co-cultured together for a period of time prior to administration.

In one embodiment, the composition comprises an effective amount or a therapeutically or prophylactically effective amount of cells. For example, the composition comprises about $1 \times 10^5$ Stro-$1^{bri}$ cells/kg to about $1 \times 10^7$ Stro-$1^{bri}$ cells/kg or about $1 \times 10^6$ Stro-$1^{bri}$ cells/kg to about $5 \times 10^6$ Stro-$1^{bri}$ cells/kg. The exact amount of cells to be administered is dependent upon a variety of factors, including the age, weight, and sex of the patient, and the extent and severity of the pancreatic dysfunction. The same values are also applicable to the progenitor cells and chondroprogenitor cells per se.

In some embodiments, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near a transplanted organ.

In some embodiments of the invention, it may not be necessary or desirable to immunosuppress a patient prior to initiation of therapy with cellular compositions. Accordingly, transplantation with allogeneic, or even xenogeneic, Stro-$1^{bri}$ cells or progeny thereof may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. The encapsulant may be hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Uses and Methods of Treatment

The methods, compositions, and uses of the present invention are useful for the treatment and/or prophylaxis of diseases of the musculoskeletal system such as rheumatoid arthritis (RA), osteoarthritis (OA) and intervertebral disc degeneration (DD). They can also be usefully employed in relation to cartilage regeneration and repair.

The methods, compositions, and uses of the present invention are also useful in that they can regulate chondrogenesis and cell proliferation and can be used to produce, upregulate or stimulate the production of hyaluronan (HA). These uses can be employed in the treatment of diseases of the musculoskeletal system including rheumatoid arthritis (RA), osteoarthritis (OA), and intervertebral disc degeneration (DD); or treating conditions that benefit from increased production of HA, such as for example osteoarthritis of synovial joints, ophthalmology, prevention of post-surgical abdominal adherences, skin treatment and repair and restoration of the function of the extracellular matrix; or inducing cartilage repair, restoration or matrix neogenesis.

Further uses of the present invention include producing an extracellular matrix suitable for transplantation into a connective tissue defect in a subject in need of such a treatment.

The methods of the present invention, can therefore be used to treat a patient, in some embodiments a human patient, from a number of diseases as stated above. The methods can also be used on a prophylactic basis to prevent or minimise the onset of these diseases.

The present invention also extends to compositions as discussed herein for use in the treatment and/or prophylaxis of diseases of the musculoskeletal system such as rheumatoid arthritis (RA), osteoarthritis (OA) and intervertebral disc degeneration (DD). They can also be usefully employed in relation to cartilage regeneration and repair, or treating conditions that benefit from increased production of HA, such as for example osteoarthritis of synovial joints, ophthalmology, prevention of post-surgical abdominal adherences, skin treatment and repair and restoration of the function of the extracellular matrix; or inducing cartilage repair, restoration or matrix neogenesis.

The compositions as discussed herein can also be used in producing an extracellular matrix suitable for transplantation into a connective tissue defect in a subject in need of such a treatment and also for regulating chondrogenesis and cell proliferation and/or producing, upregulating or stimulating the production of hyaluronan (HA).

The present invention also extends to the use of compositions as discussed herein in the manufacture of a medicament for the treatment and/or prophylaxis of diseases of the musculoskeletal system such as rheumatoid arthritis (RA), osteoarthritis (OA) and intervertebral disc degeneration (DD). The use also extends to cartilage regeneration and repair, or treating conditions that benefit from increased production of HA, such as for example osteoarthritis of synovial joints, ophthalmology, prevention of post-surgical abdominal adherences, skin treatment and repair and restoration of the function of the extracellular matrix; or inducing cartilage repair, restoration or matrix neogenesis.

The use of compositions as discussed herein also extends to the manufacture of a medicament for producing an extracellular matrix suitable for transplantation into a connective tissue defect in a subject in need of such a treatment and for regulating chondrogenesis and cell proliferation and/or producing, upregulating or stimulating the production of hyaluronan (HA).

The present invention allows for the administration of the compositions of the present invention to implant progenitor cells into a patient which are subsequently induced to increase HA production and/or undergo transformation into a chondrogenic phenotype.

Examples of such an application would be to inject the compositions of the present invention into joints of individuals with cartilage or disc lesions or systemically for other less accessible sites, allowing the preparation to perfuse the tissue and cells thereby exerting its unique biological effects. Applications could include any treating individuals who may not have clinical defined disease (often OA or related disorders) but have sustained a traumatic injury to joint tissues though sport or work-related activity.

In older subjects with OA or related disorders this form of treatment could be used instead of intra-articular HA therapy (viscosupplementation).

It could also serve as a prophylactic method following arthroscopic or open surgery where cartilage or meniscal excision/debridement was necessary. It is well established that with time such post surgical patients will generally progress to exhibit symptomatic OA requiring medical treatment. It is not unlikely that by diminishing cartilage degradation symptoms may also improved because of the reduction in production of cartilage derived auto-antigens which promote inflammation.

Compositions according to the invention that have been shown to have activity can be further tested for safety and efficacy in other animal models, and then proceed to clinical trials in humans, if desired. Naturally, for veterinary applications, no clinical trial in humans is required. Those compositions that are safe and efficacious in animals or humans can be administered to an appropriate subject to treat or alternatively to protect against the diseases discussed herein. "Treatment and protection" includes both prophylactic and therapeutic measures to prevent the onset and appearance of diseases as discussed herein.

The treatment methods herein refers to defending against or inhibiting a symptom, delaying the appearance of a symptom, reducing the severity of the development of a symptom, and/or reducing the number or type of symptoms suffered by an individual, as compared to not administering a pharmaceutical composition comprising a polypeptide of the invention. Accordingly, throughout this description, it will be understood that any clinically or statistically significant attenuation of even one symptom of a musculoskeletal degenerative condition pursuant to the treatment according to the present invention is within the scope of the invention.

The following examples further illustrate aspects of the present invention. However, they are in no way a limitation of the teachings or disclosure of the present invention as set forth herein.

Results and Discussion

The present invention has shown that the addition of polysulfated polysaccharides over a wide range of concentrations to cryogenic media such as Profreeze® and 7.5% DMSO containing progenitor cells in both high and low numbers followed by freezing in liquid nitrogen vapour phase and thawing at ambient temperatures or 37° C. had no detrimental effect on their viability. This can be seen by FIGS. 1-3. Indeed, enhanced viability was seen from these experiments, in particular FIG. 3 and also FIG. 4 which shows that progenitor cell viability was enhanced relative to progenitor cells frozen in cryo-preservation media not containing the polysulfated polysaccharide.

Figure 6:
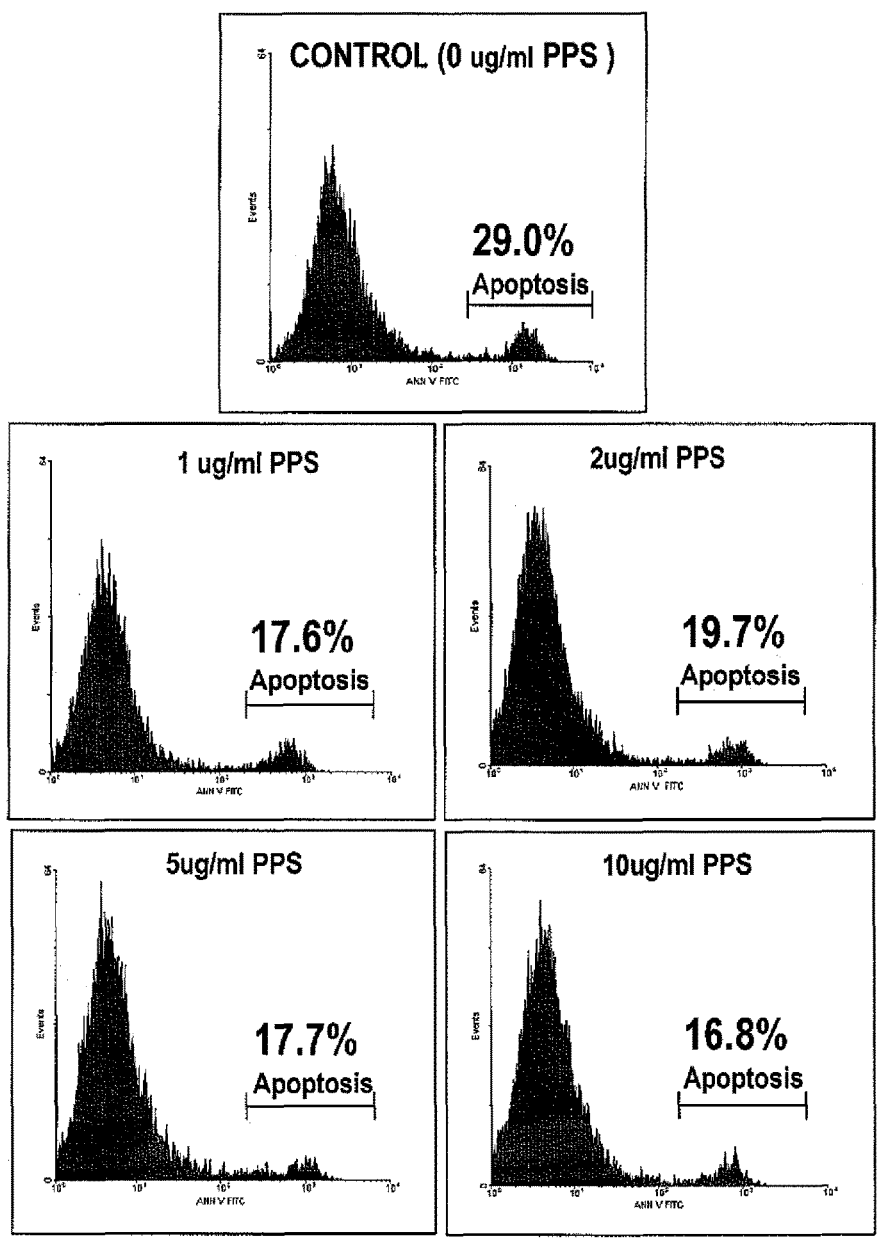
FIG. 6. The Effects of Pentosan Polysulfate (PPS) on Human progenitor cells treated with apoptotic agents. Human progenitor cells were plated in serum-free media supplemented with PPS at the indicated concentrations. Progenitor cell apoptosis was induced by the addition of a combination of 30 ng/ml IL-4 plus 30,000 U/ml IFN-gamma. Following 5 days culture, cells were harvested by trypsinisation and viabilities assessed by Annexin V staining. A two-fold reduction in IFN-gamma/IL-4-induced apoptosis (Annexin V positive cells) is observed when progenitor cells are cultured at concentrations of PPS in excess 1 ug/ml.

FIG. 6 clearly shows that polysulfated polysaccharide concentrations above 1 microgram/mL reduced apoptosis in human progenitor cells by about 50% when these cells were incubated with IL-4 and IFN-gamma which were known mediators of apoptosis.

Figure 4:
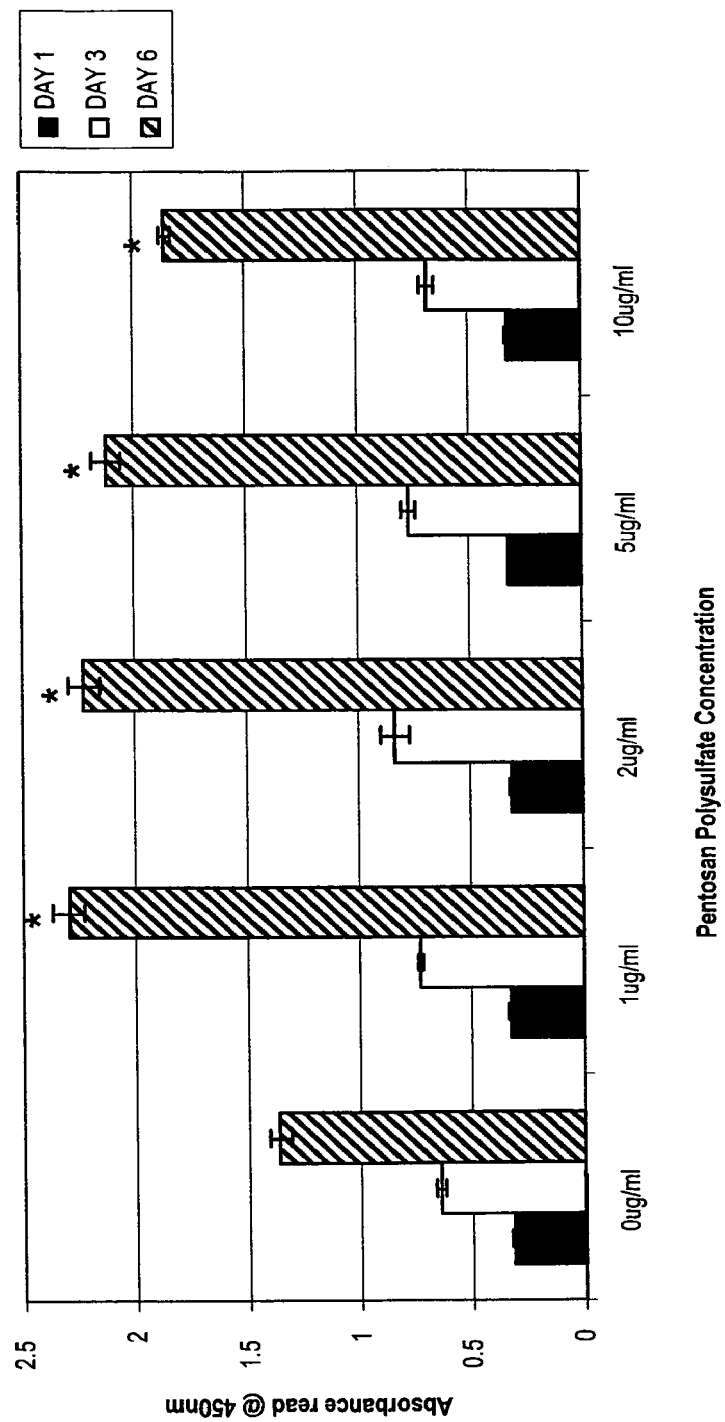

It has also been shown that polysulfated polysaccharides stimulate progenitor cell prolferation in a concentration dependent manner. Marked stimulation of cell division, as measured with the WST-1 mitchondral dehydrogenase cleavage assay is seen in FIG. 4 and from incorporation of $^3$H-Thymidine into DNA in FIG. 5 which was demonstrated over the range of 1-5 micrograms/mL in monolayer and micromass cultures of human progenitor cells as well as in a murine progenitor cell line in FIG. 10.

In contrast to several members of the BMP-TGF-beta super family (eg, BMP-2, BMP-7, BMP-8) and fibroblast growth factor family which promote differentiation of progenitor cells to osteoblasts when cultured in osteogenic media, it was found for the first time that polysulfated polysaccharides suppress differentiation of progenitor cells to this cell phenotype. This can be seen in FIG. 7 and shown downregulation of the progenitor cell with regard to osteogenesis.

On the other hand progenitor cells cultured in adipogenic media in the presence polysulfated polysaccharides showed differentiated to adipocytes. Thus, polysulfated polysaccharides act as a regulator of progenitor cell differentiation into adipocytes. This can be seen in FIG. 8.

Under normal non-selective culture conditions incubation of polysulfated polysaccharides with progenitor cells invariably favoured differentiation along the chondrogenic pathway as demonstrated by increased proteoglycan and type II collagen synthesis. Proteoglycans and type II collagen are recognised biosynthetic products of chondrocytes and are used as phenotypic markers of hyaline cartilage. The chondrogenic promoting effect of polysulfated polysaccharides was shown in the Murine MSC cell line C3H10T1/2 in FIG. 9 and human progenitor cells in FIG. 11 when cultured in monolayers.

Figure 12:
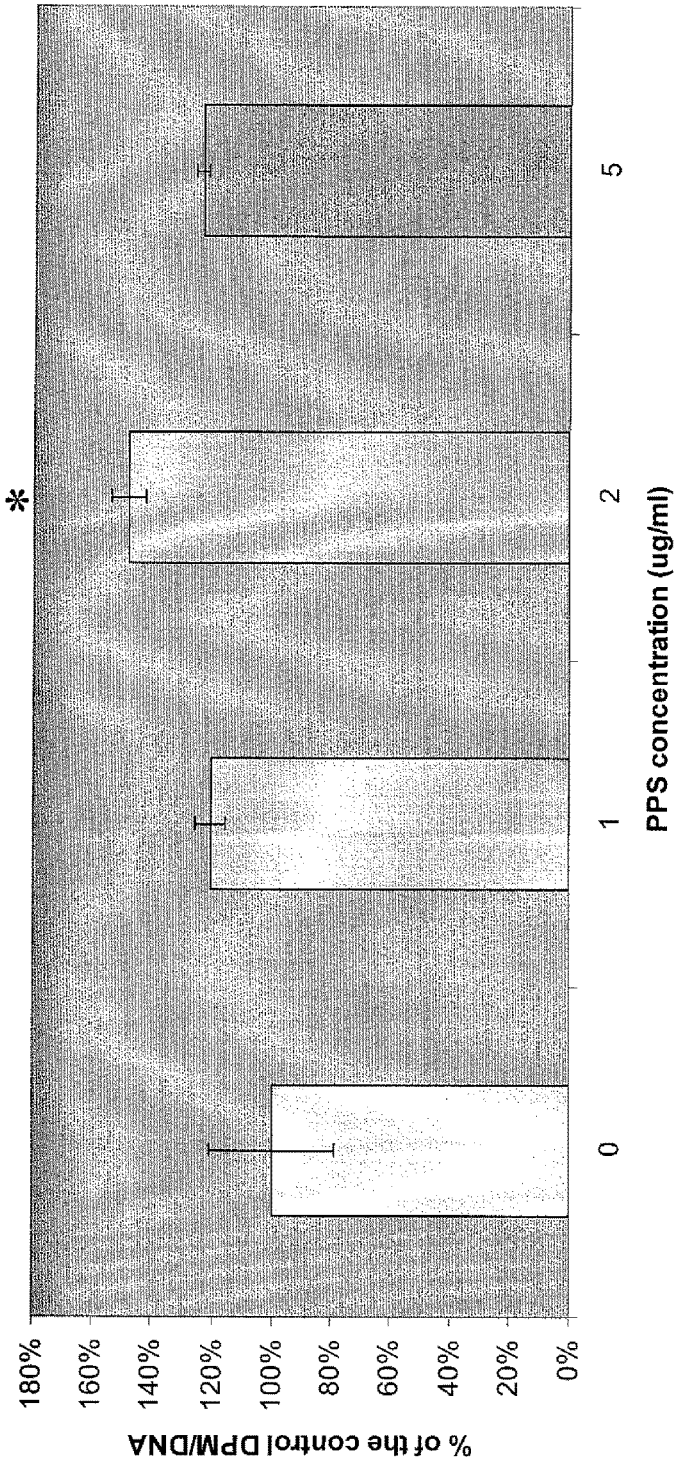
FIG. 12. A bar graph of the concentration dependent effects of Pentosan Polysulfate (PPS), on the biosynthesis of Proteoglycans (PGs) as determined by the incorporation of radioactively labelled sulfate into the sulfated glycosaminoglycans ($^{35}$S-GAG) of PGs in 6 day pellet cultures of murine progenitor cells (ADTC-5). *=p<0.05 relative to control.

Additional support was provided in pellet cultures using the Murine ATDC5 cell line where a 25% increase of proteoglycan (PG) synthesis relative to control culture (no polysulfated polysaccharides) was observed at 2 micrograms/mL in FIG. 12.

Figure 13:
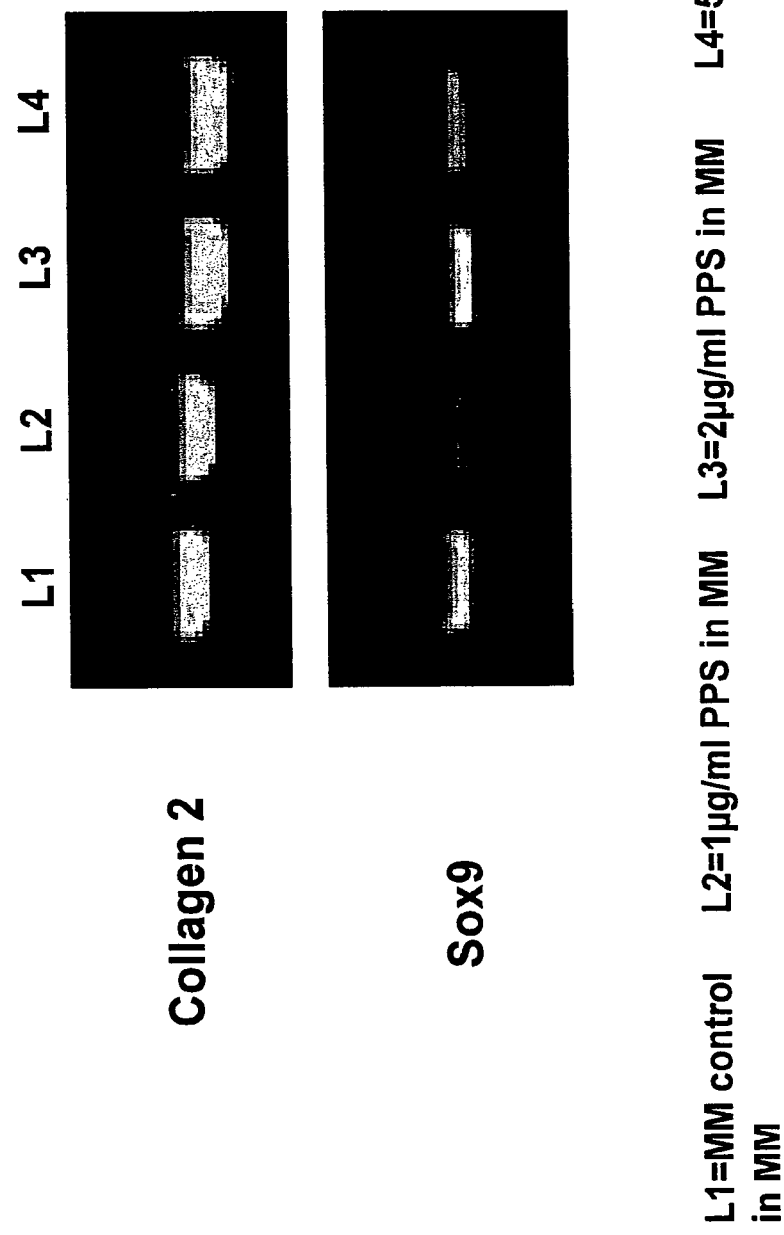
FIG. 13. Gene Expression by ATDC5 cells of Type II collagen and Sox-9 in 6-day pellet culture incubated with various concentrations of PPS in Maintenance Medium (MM).

Additional evidence that polysulfated polysaccharides promoted chondrogenesis and cartilage formation was provided by examination of gene expression by these cells after 6 days in pellet culture, where type II collagen expression, was up-regulated in a concentration dependent manner by polysulfated polysaccharides. This can be seen in FIG. 13.

Interestingly, Heparin, a naturally occurring polysulfated polysaccharide failed to significantly stimulate proteoglycan synthesis in pellet culture over all of the concentrations examined. This can be seen in FIG. 14. Heparin shows little activity at the concentration of 2.5 ugrams/mL but may cause inhibition at higher concentrations.

Figure 15:
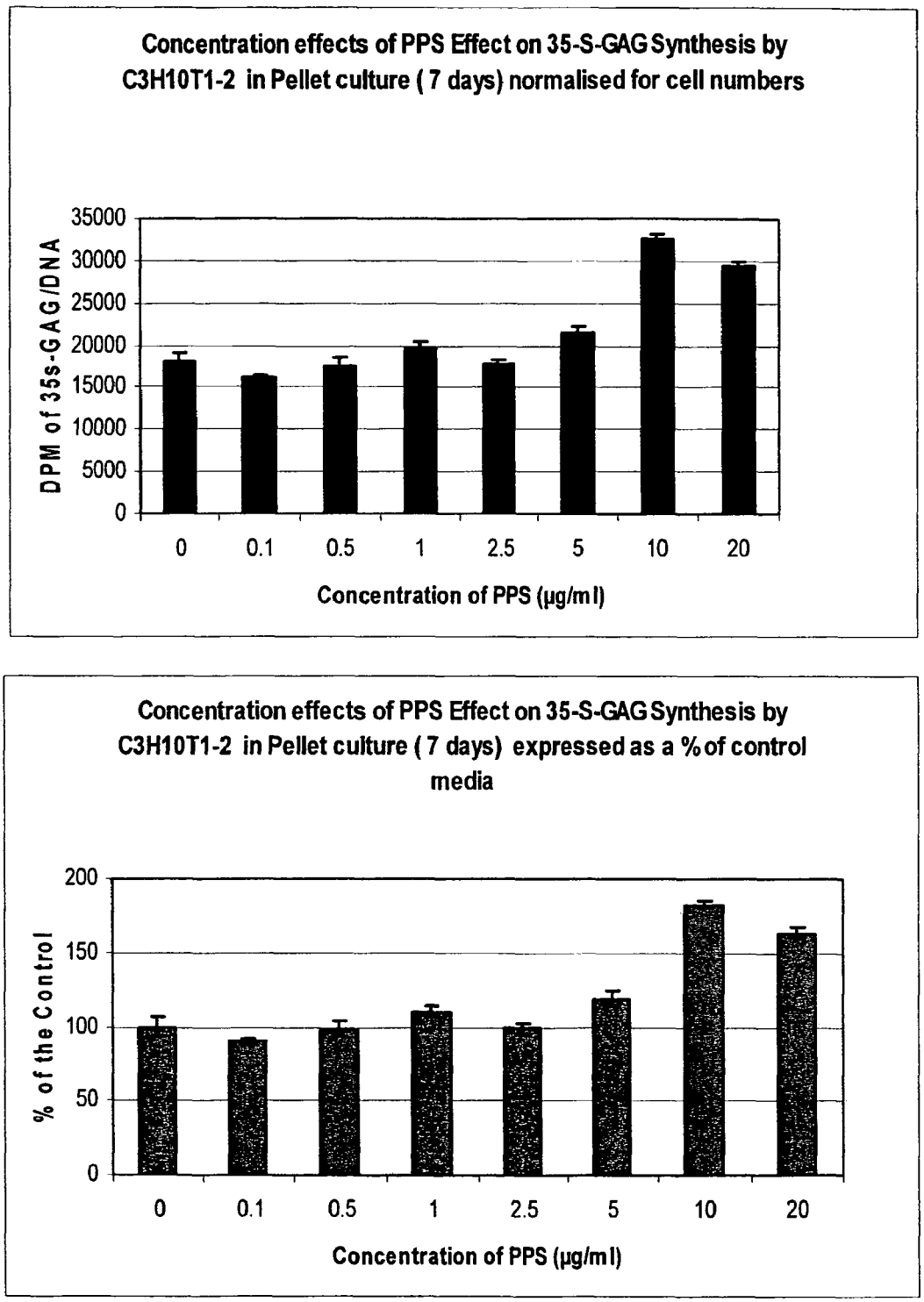
FIG. 15. Bar graphs showing the concentration dependent effects of Pentosan Polysulfate (PPS), on the biosynthesis of Proteoglycans (PGs) as determined by the incorporation of radioactively labelled sulfate into the sulfated glycosaminoglycans ($^{35}$S-GAG) of PGs in 7 day pellet cultures of a murine progenitor cells (C3H10T1-2).

Using the Murine MSC line C3H10T1/2 in 7 day pellet culture demonstrated that polysulfated polysaccharides at 10 micrograms/mL increased proteoglycan synthesis by more than 80% of the control values. This can be seen in FIG. 15. This finding was consistent with the results obtained using a Murine MSC line C3H10T1/2 in micromass cultures over 6 days which can be seen in FIG. 16. This method of culturing progenitor cells was originally described by Denker et al (Andrew E. Denker A E, Haas A R, Nicoll S B, Tuan R S. Chondrogenic differentiation of murine C3H10T1/2 multipotential progenitor cells: I. Stimulation by bone morphogenetic protein-2 in high-density micromass cultures. Differentiation (1999) 64:67-76 1999).

Figure 17:
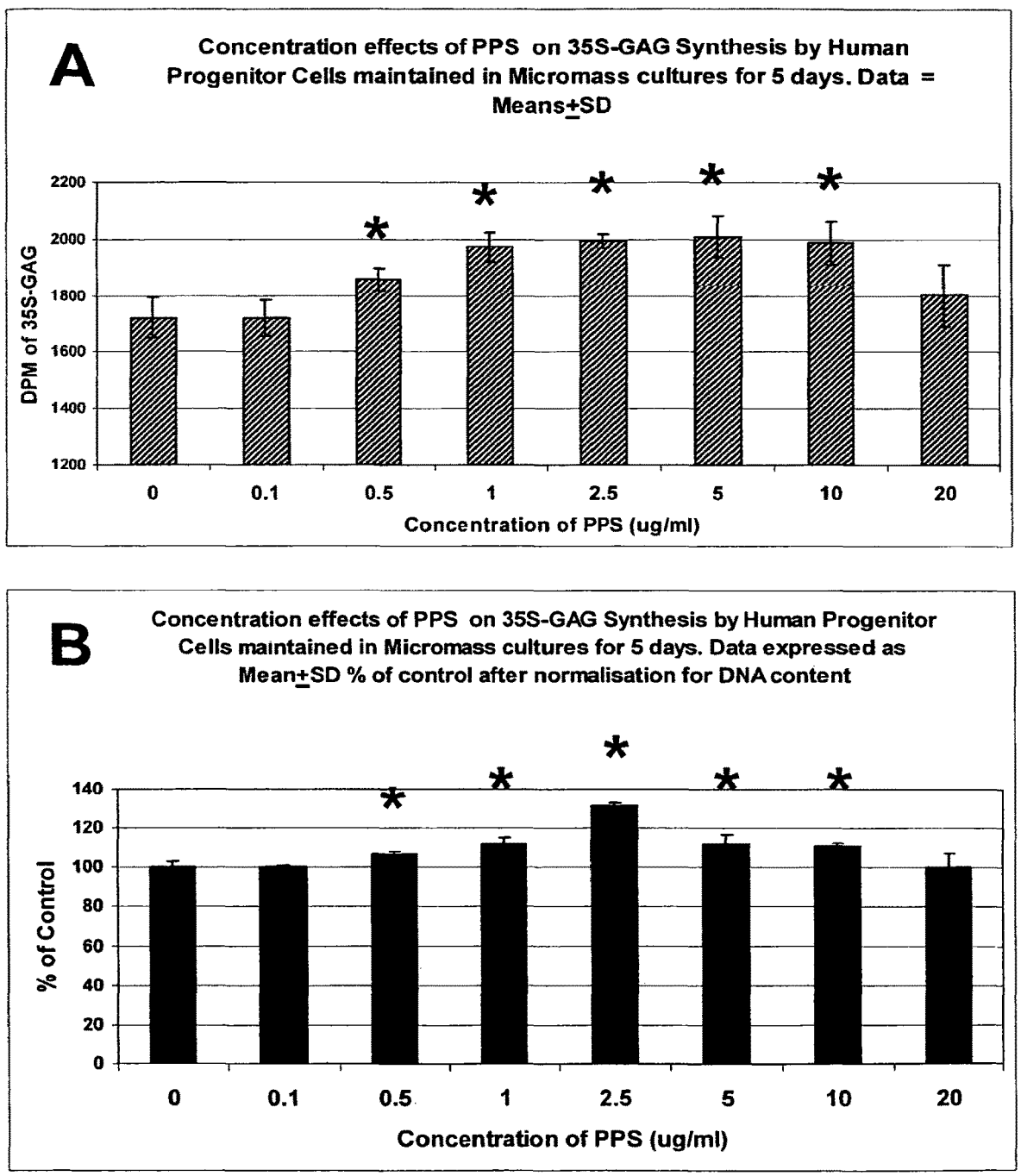
FIG. 17. Bar graphs showing the concentration dependent effects of PPS on proteoglycan synthesis by human progenitor cells in micromass cultures for 5 days. Data is presented as 35S-GAG radioactivity and as a percentage of control taken as 100%. * P<0.05 relative to control.

Moreover, after nine days in micromass cultures a 100% stimulation was obtained at 1 microgram/mL of polysulfated polysaccharides also shown in FIG. 16. Human progenitor also differentiated to chondrocytes in micromass cultures when incubated in the presence of polysulfated polysaccharides. However in the 5 day cultures a maximum stimulation of PG synthesis of 30% was obtained with polysulfated polysaccharides concentration of 2.5 micrograms/mL as shown in FIG. 17. The co-production of type II collagen with PGs was confirmed in these micromass cultures using the immuno-staining technique described by Denker et al (Andrew E. Denker A E, Haas A R, Nicoll S B, Tuan R S. Chondrogenic differentiation of murine C3H10T1/2 multipotential progenitor cells: I. Stimulation by bone morphogenetic protein-2 in high-density micromass cultures. Differentiation (1999) 64:67-76 1999).

As is evident from FIG. 18, micromass cultures of human progenitor cells maintained in the presence of polysulfated polysaccharides over the concentration range of 1-10 micrograms/mL for 10 days afforded intense type II collagen staining, the maximum levels being achieved with polysulfated polysaccharides at 5 micrograms/mL.

In similar micromass cultures undertaken with human progenitor cells and hyaluronan (HA) a low level of $^{35}SO4$ incorporation into PGs was observed in FIG. 19A. However, the highly negatively charged Dextran Sulfate (DS) inhibited PG synthesis over the range of 1-20 micrograms/mL (FIG. 19B). This was a surprising result since DS has a similar molecular weight and charge density to polysulfated polysaccharides and was therefore expected to demonstrate similar activity on the progenitor cells. It is believed that molecular conformation and other factors important for effective receptor binding and protein interactions may be playing a role.

Figure 20:
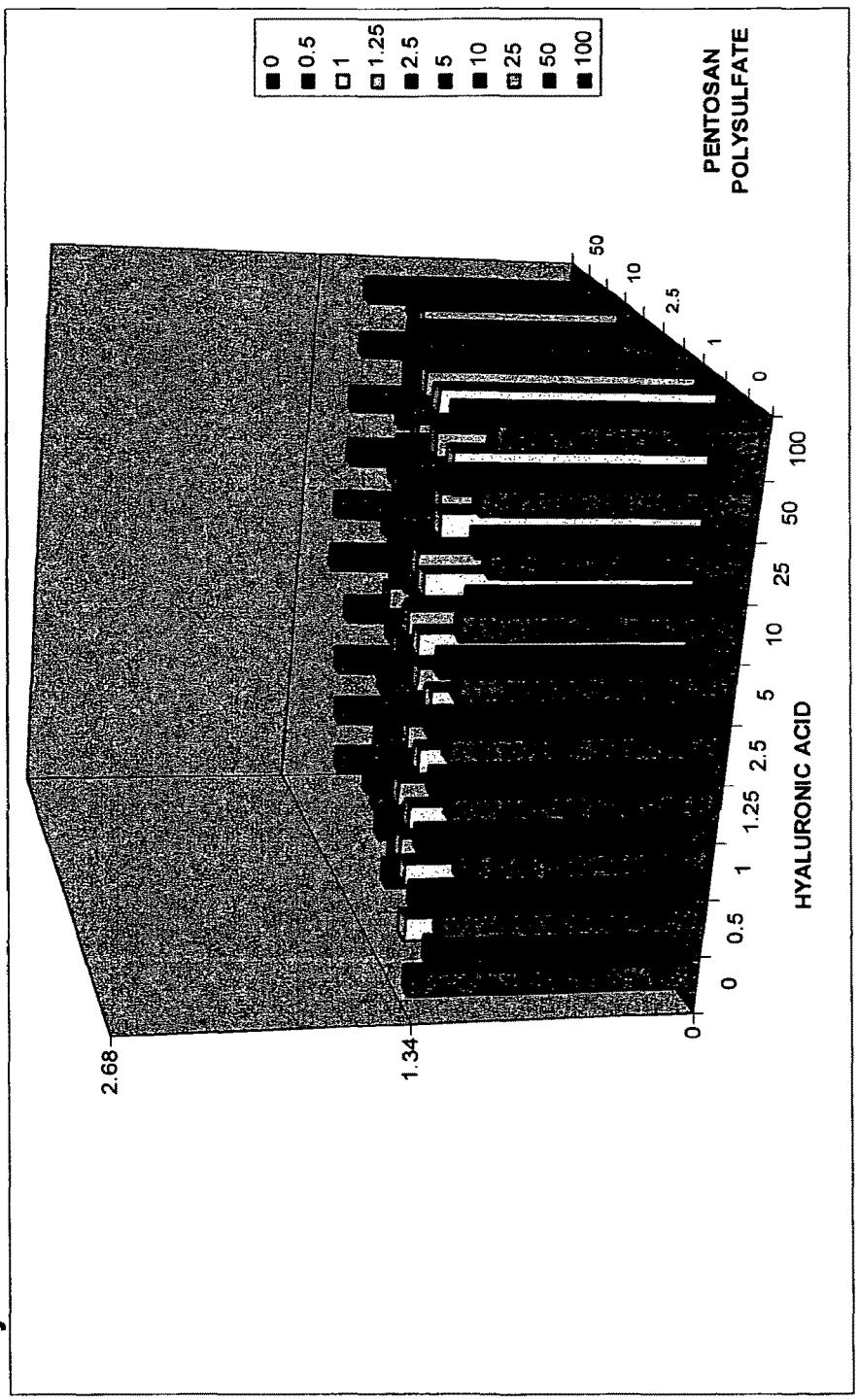
FIG. 20. Shows the results of culturing primary human progenitor cell growth media supplemented with PPS and/or Hyaluronic acid (Supartz™), at the indicated concentrations. At various time intervals (day 3 & 5), the growth media was removed and replaced with phenol red free media containing the tetrazolium salt WST-1 for 2 hours at 37° C./5% CO$_2$. Absorbance at 450 nm for each time point is shown for all concentrations of PPS and HA. This experiment shows that HA and PPS do not act synergistically to stimulate progenitor proliferation.
Figure 20:
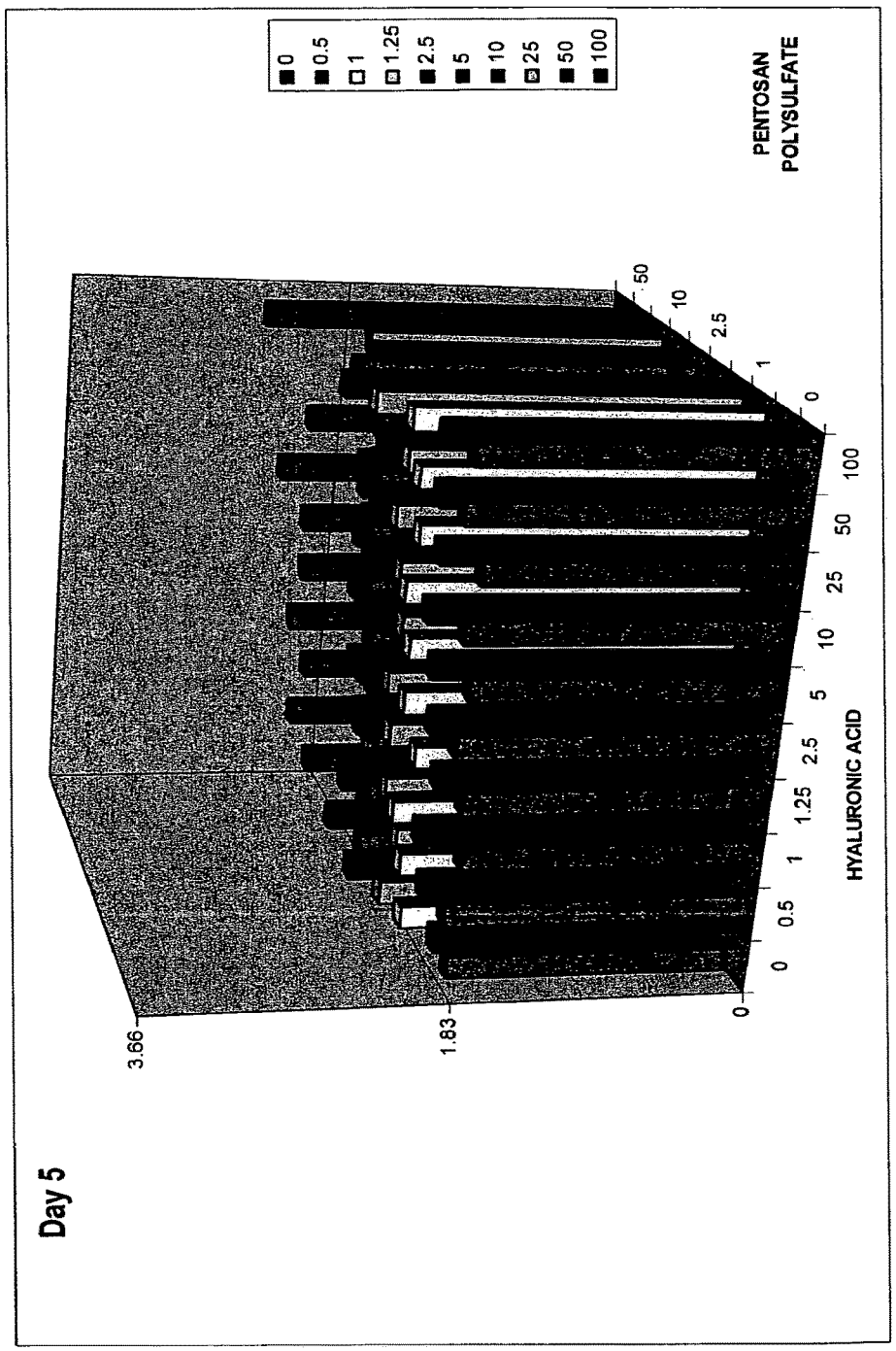

Hyaluronan is reported to exert chondrogenic effects on progenitor cells in alginate bead cultures (Kavalkovich K W, Boynton R E, Murphy J M, Barry F. Chondrogenic differentiation of human progenitor cells within an alginate layer culture system. In vitro Cell. Dev. Biol—Animal.38:457-466, 2002). In FIG. 20 the effects of Pentosan Polysulfate alone and in combination with Hyaluronan (Supartz™) on human progenitor cell proliferation using the WST-1 assay is shown for day 3 and day 5 cultures. The results of this experiment confirmed the absence of any significant stimulatory effect by HA alone on progenitor cell proliferation and also demonstrate the absence of any synergist effect for the combinations with polysulfated polysaccharides. Thus, it can be seen that polysulfated polysaccharides are better chondrogenic agents than HA. In addition, in contrast with NC4, HA does not combine synergistically with polysulfated polysaccharides.

A recombinant human preparation of the non collagenous domain of the alpha-1 chain of type IX collagen, rhNC4 was also found to induce chondrogenesis and PG production by progenitor cells. As is evident from FIG. 21, a concentration dependent stimulation of PG synthesis was observed both in the absence (maintenance media) and presence of Insulin (differentiation media) on ATDC5 cells, maximum effects occurring at 1 microgram/mL. This stimulatory effect of rhNC4 was also demonstrated in pellet cultures of ATDC5 cells but in maintenance media the optimum effect was produce at a concentration of 0.5 micrograms/mL.

Figure 23:
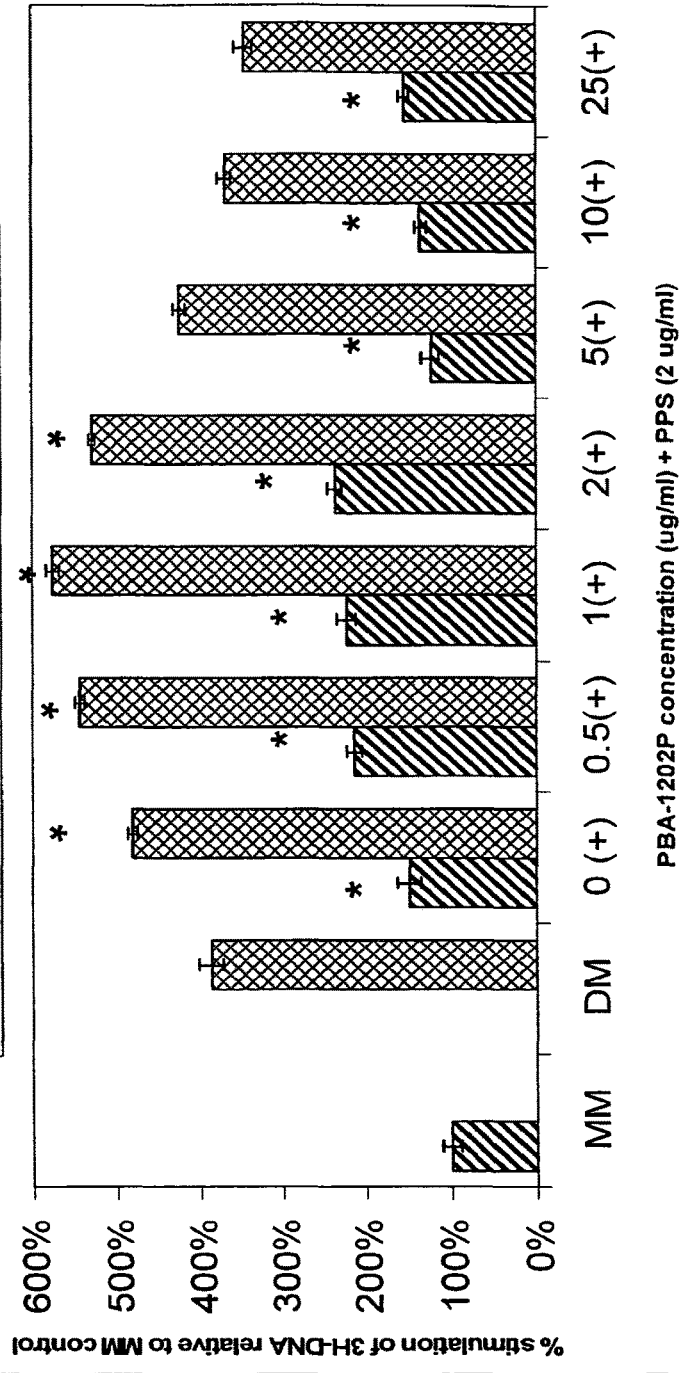
FIG. 23. A bar graph of the concentration dependent effects of rhNC4 (batch PBA-1202P) expressed by *K. lactis* plus Pentosan Polysulfate (PPS) (2 micrograms/mL), in the absence (maintenance media, MM) and presence of insulin (10 micrograms/mL) (differentiation media, DM), on the biosynthesis of macromolecular DNA as determined by the incorporation of radioactively labelled $^3$H-Thymidine after 1 day culture with Murine ATDC5 progenitor cells. The data was expressed as % change relative to control cultures that contained no rhNC4. P<0.05 was statistically significant relative to control cultures.
Figure 24:
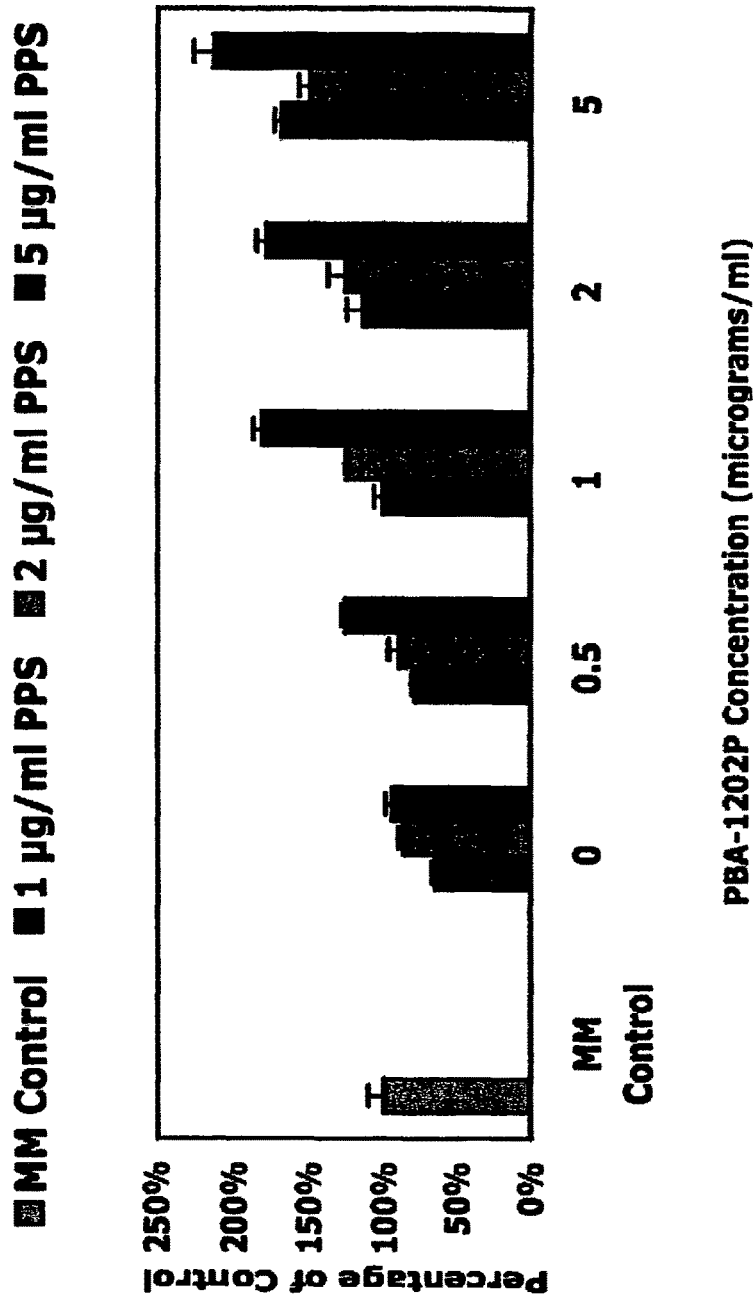
FIG. 24. A bar graph of the concentration dependent effects of combinations of rhNC4 (batch PBA-1202P) and Pentosan Polysulfate (PPS) on the biosynthesis of $^{35}$S-PGs by monolayer cultures of Murine ATDC5 progenitor cells. Data is expressed relative to control (maintenance media, MM) which was taken as 100%.

The chondrogenic and mitogenic effects of rhNC4 on Murine ADTCS cells were observed to be enhanced when the protein was co-cultured with polysulfated polysaccharides as can be seen in FIGS. 23 and 24. The combination of rhNC4 and polysulfated polysaccharides was, in contrast to HA and polysulfated polysaccharides, synergistic as shown by a 450% stimulation of $^3$H-DNA synthesis in differentiation culture media at concentrations of 1microgram/mL of rhNC4 and 2 micrograms/mL of polysulfated polysaccharides (FIG. 23). In terms of stimulation of PG synthesis, 1-5 micrograms/mL rhNC4 with 5 micrograms polysulfated polysaccharides appeared to be the most effective combination (FIG. 24).

Figure 21:
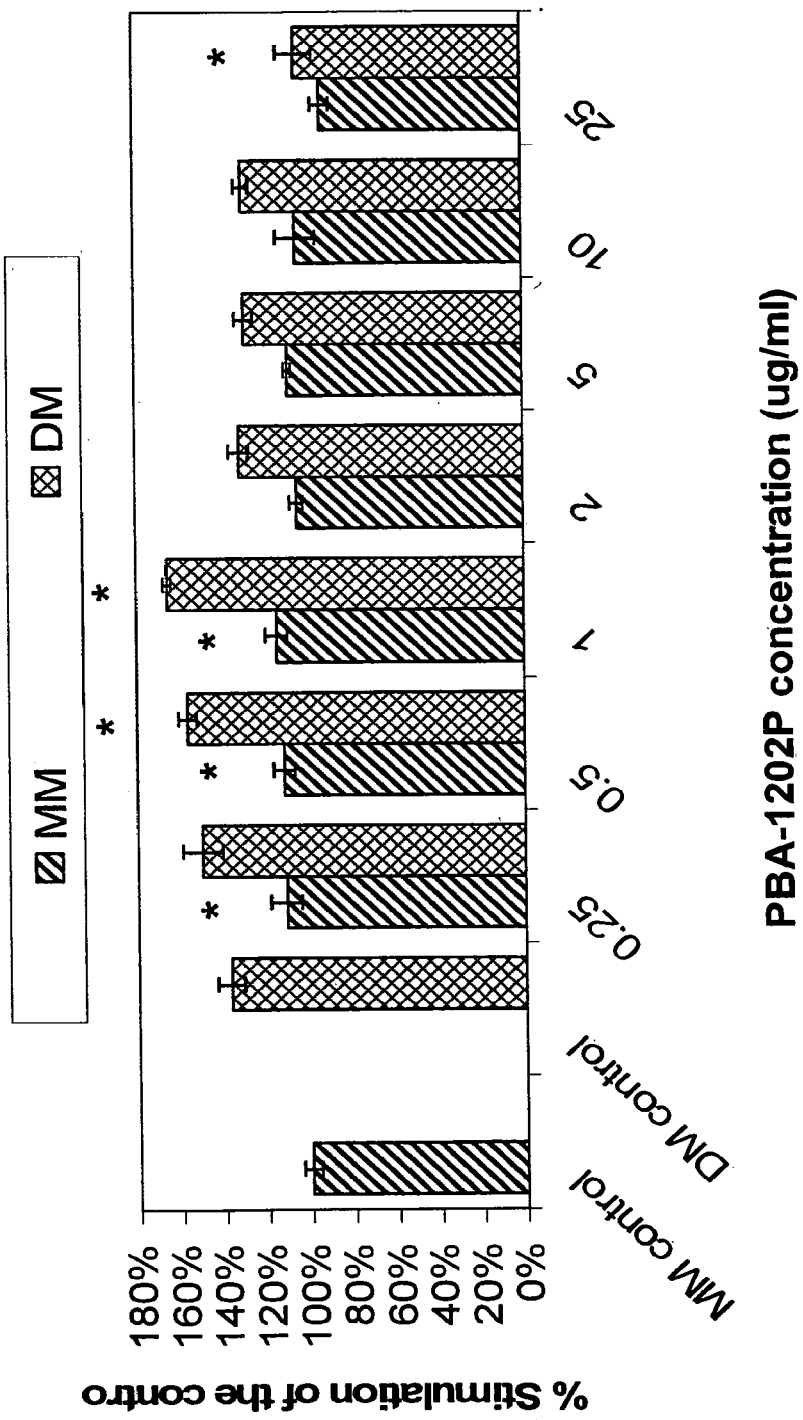
FIG. 21. A bar graph of the concentration dependent effects of rhNC4 (batch PBA-1202P) expressed by *K. lactis*, in the absence (maintenance media, MM) and presence of insulin (10 micrograms/mL) (differentiation media, DM), on the biosynthesis of Proteoglycans (PGs) as determined by the incorporation of radioactively labelled sulfate into the sulfated glycosaminoglycans ($^{35}$S-GAG) of PGs after 3 day culture with Murine ATDC5 progenitor cells. The data was expressed as % change relative to control cultures that contained no rhNC4. P<0.05 was statistically significant relative to control cultures.
Figure 33:
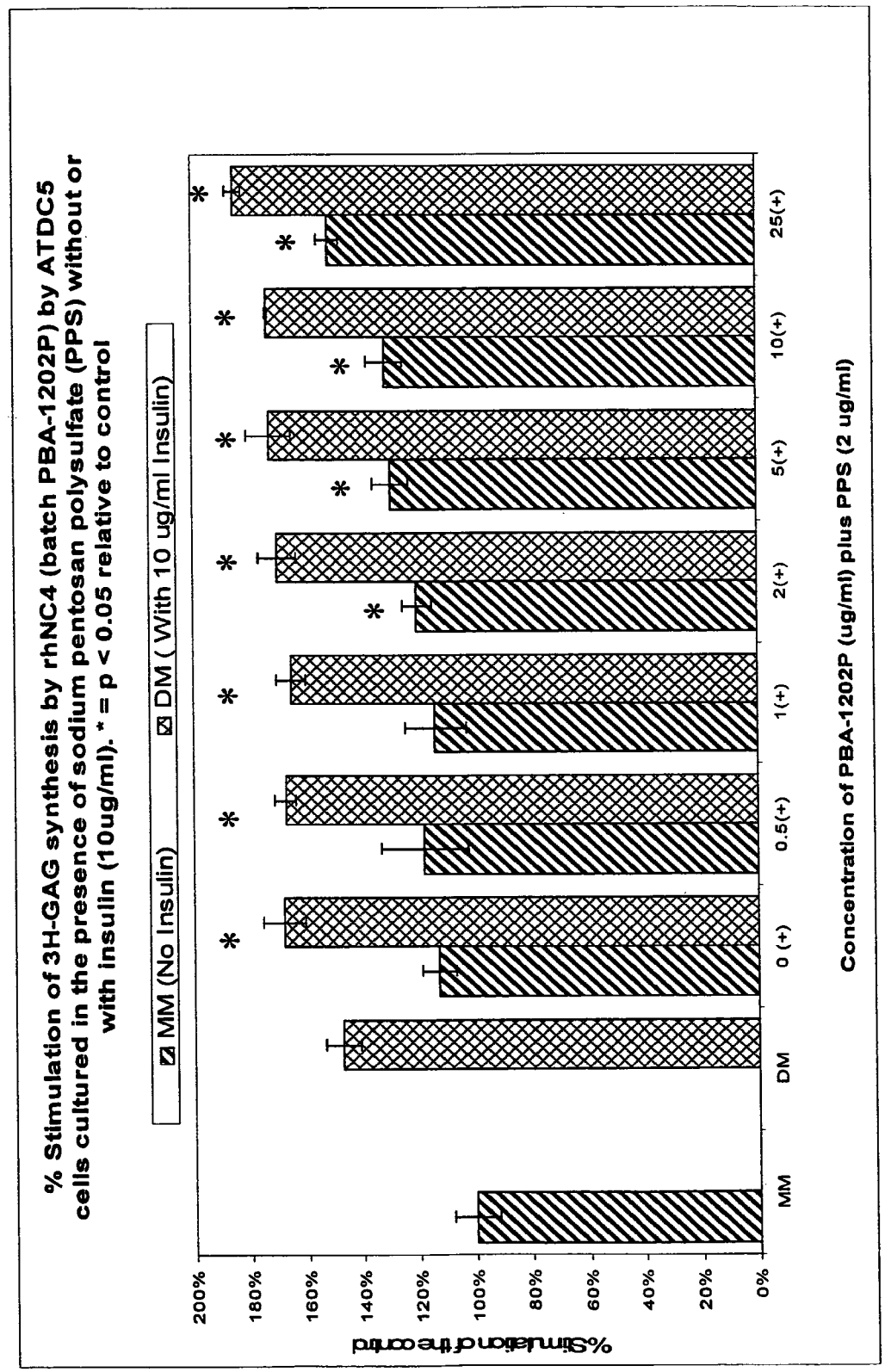
FIG. 33. A bar graph of the concentration dependent effects of rhNC4 (batch PBA-1202P) expressed by *K. lactis* plus sodium pentosan polysulfate (PPS) (2 micrograms/mL), in the absence (maintenance media, MM) and presence of insulin (10 micrograms/mL) (differentiation media, DM), on the biosynthesis of Proteoglycans (PGs) as determined by the incorporation of radioactively labelled glucosamine into the glycosaminoglycans ($^3$H-GAG) of PGs after 1 day culture with Murine ATDC5 progenitor cells. The data was expressed as % change relative to control cultures that contained no rhNC4. P<0.05 was statistically significant relative to control cultures.
Figure 34:
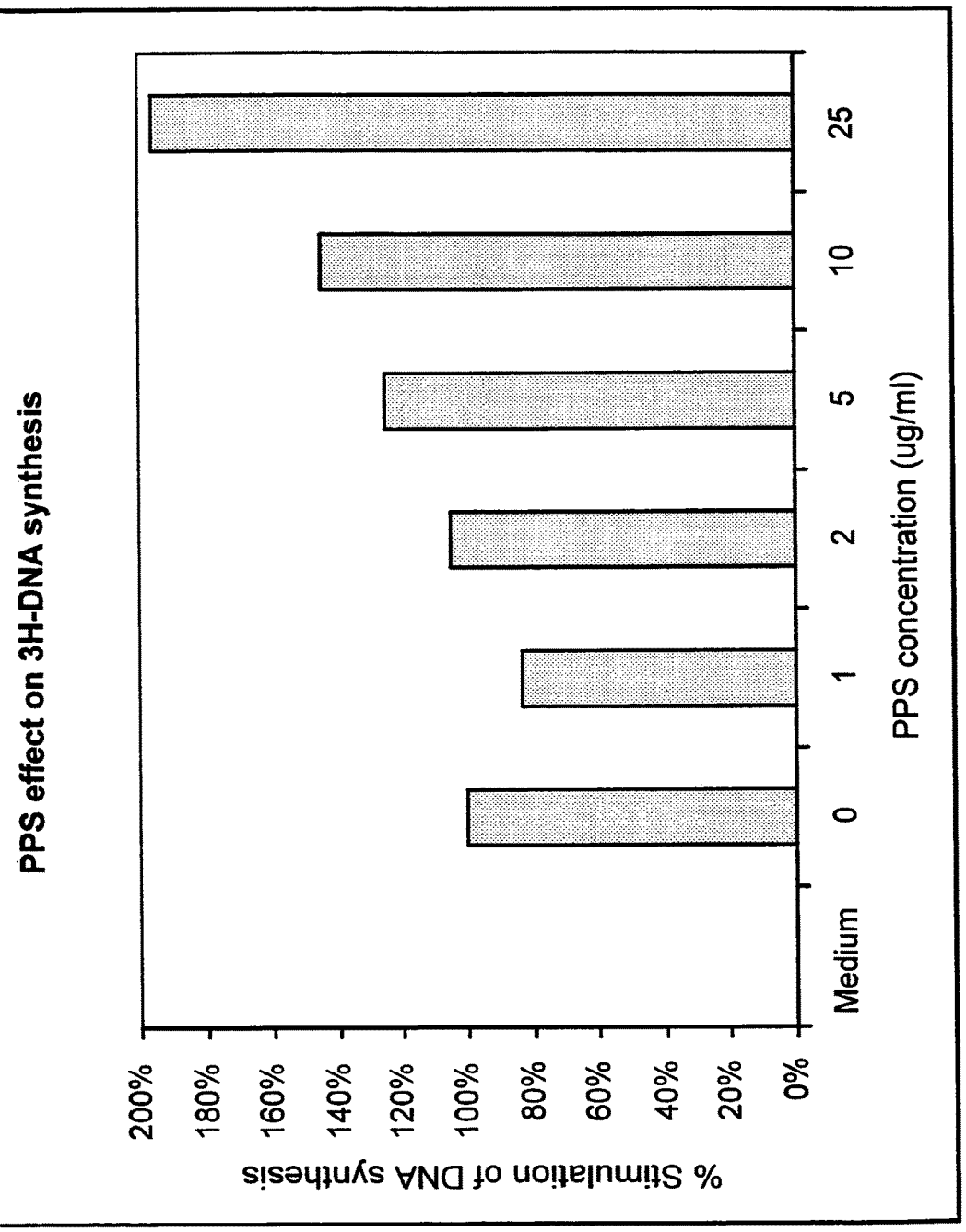
FIG. 34. A bar graph of the concentration dependent effects of Pentosan Polysulfate (PPS) in the presence of insulin (10 micrograms/mL) on DNA synthesis (cell replication), as determined by the incorporation of $^3$H-Thymidine into macromolecular DNA after 3 day culture with Murine ATDC5 progenitor cells. The data is expressed as % change relative to control cultures that contained no PPS.

FIGS. 21, 33 and 23 show the outcome of experiments using both a differentiation medium (DM) for the progenitor cells (ATDC5) containing a growth factor (in this case insulin) and the maintenance media (MM) which does not contain a growth factor. FIG. 21 shows the use of NC4 alone, while FIGS. 33 and 23 show the effects of the combination of the polypeptide and the polysulfated polysaccharide. It can be seen that the compounds of the present invention promoted chondrogenesis in the absence of the growth factor but also had a positive effect on the rate of chondrogenesis in the presence of the growth factors. Therefore, the compounds of the present invention can be used without other growth factors but can also be used with other growth factors to promote chondrogenesis further.

Figure 25:
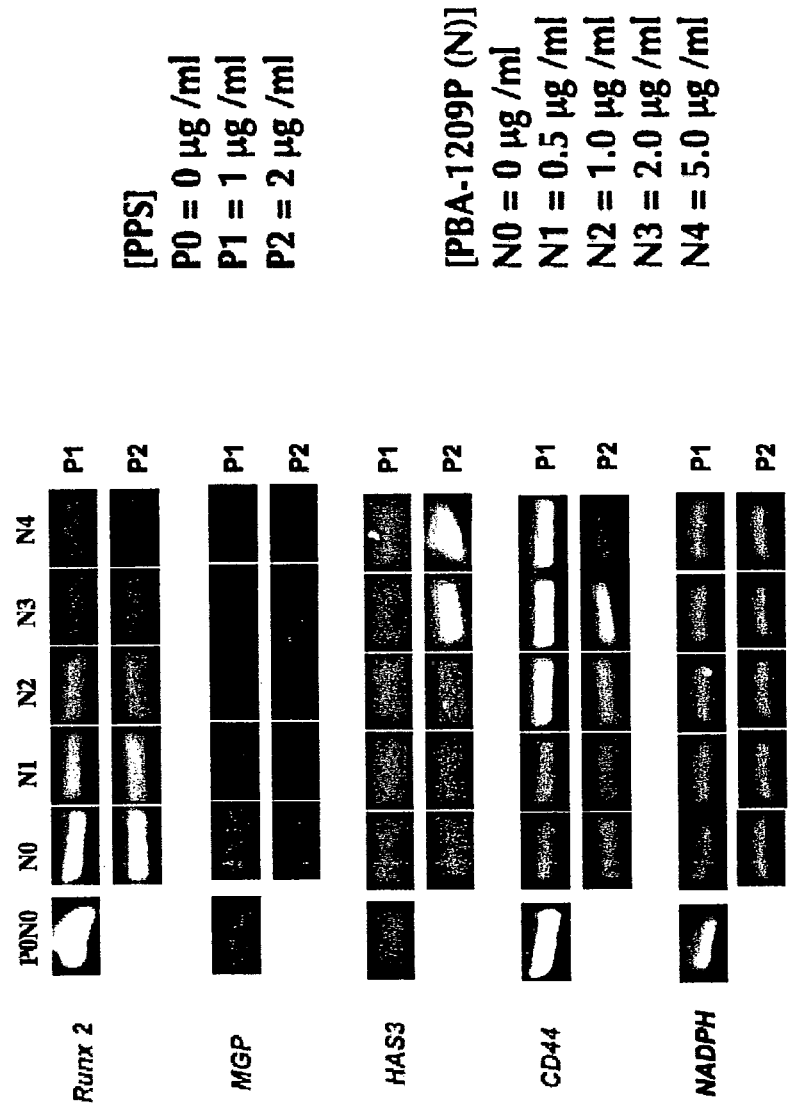
FIG. 25. RT-PCR detection of gene expression of the bone marker Runx2, MGP, HAS3, CD44 and the housekeeping gene NADPH expressed by Murine ATDC5 progenitor cells cultured in the presence and absence of rhNC4 (Batch PBA-1209P) and PPS for 2 days in monolayer cultures.
Figure 26:
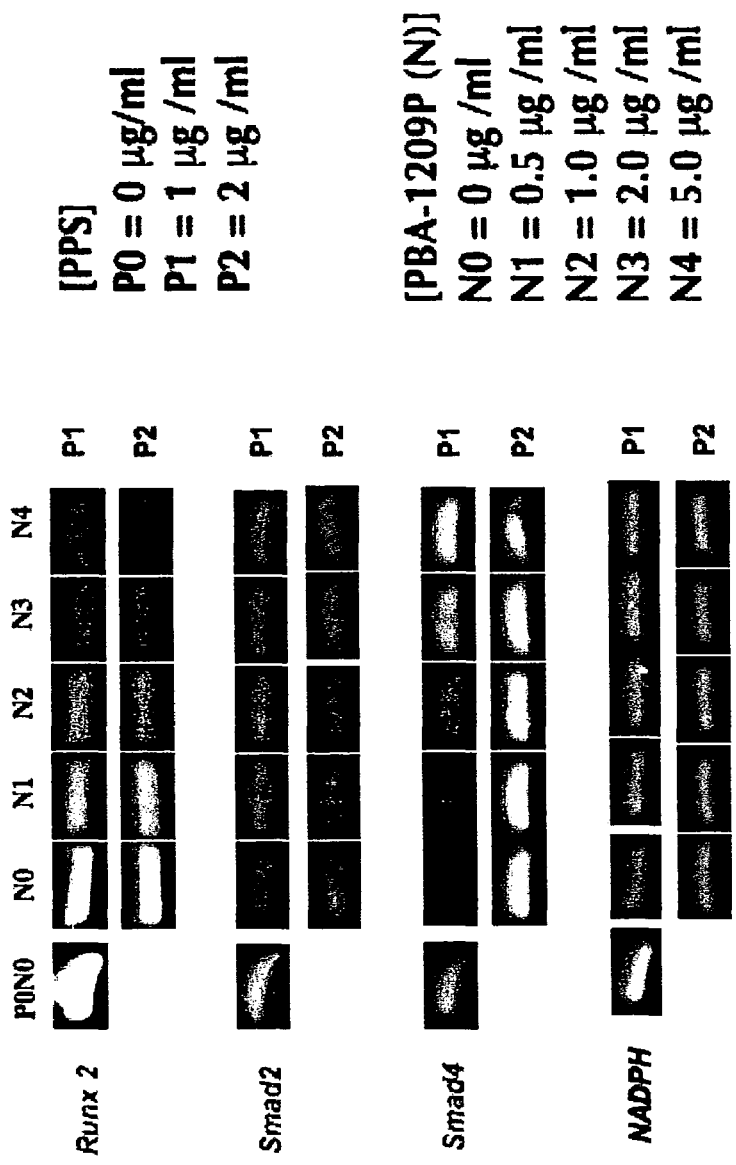
FIG. 26. RT-PCR detection of gene expression of Runx2 and the transduction proteins, Smad 2 and Smad 4 and the housekeeping gene NADPH expressed by Murine ATDC5 progenitor cells cultured in the presence and absence of rhNC4 (Batch PBA-1209P) and PPS for 2 days in monolayer cultures.

Studies of the expression of Runx 2 gene by ATDC5 cells cultured in the presence of rhNC4 and polysulfated polysaccharides showed a progressive down regulation of this bone marker with increasing concentrations (FIGS. 25 and 26). By contrast one of the genes for HA synthesis (HAS3) and the receptor for HA (CD44) were both up regulated by these compounds (FIGS. 25 and 26). Of particular interest was the finding of the up regulation of Smad 2 and Smad 4 by polysulfated polysaccharides alone and polysulfated polysaccharides+rhNC4 at concentrations which were shown to stimulate PG synthesis. Smad 4 has been reported to be a major intracellular protein for the transactivation of the type-II collagen promoter in progenitor cells when these cells are activated by BMPs (Hatakeyama Y et al. Smad signaling in progenitor and chondroprogenitor cells. J Bone Joint Surg AM. 85A Suppl 3, 13-8, 2003, Chen D, Zhao M, Munday G R, Bone morphogenetic proteins. Growth Factors, 22: 233-41, 2004). Whilst not wishing to be bound by theory, it is possible therefore that the chondrogenic/proliferatatory effects of polysulfated polysaccharides and NC4 on progenitor cells could be mediated via the actions of BMPs, the levels of which are elevated in the presence of these two compounds when used alone or in combination.

Experimental Methods and Protocols

Determination of Protein Content of Samples Using the Bicinchoninic Acid (BCA) Assay The protein content of all samples was determined using BCA assay (Smith P K, Krohn R I, Hermanson G T, Mallia A K, Gartner F H, Provenzano M D, Fujimoto E K, Goeke N M, Olson B J and Klenk D C. Anal. Biochem. 150, 76-85, 1985). Freeze dried protein samples were directly dissolved in H2O to provide a 2.0 mg/ml solution. 20 μl of each sample solution was added to a well of 96-well plates. Just prior to assay, 50 parts of reagent 1 (0.4% NaOH; 1.7% $Na_2CO_3$; 0.95% $NaHCO_3$; 1.0% bicinchoninic acid; 0.16% $Na_2$-tartrate) was mixed with reagent 2 (4% $CuSO_4.5H_2O$). 200 μl of this working reagent was added to the sample solution. After incubation at 37° C. for 60 min the absorbance A562 was read using a Thermomax microplate reader. Bovine serum albumin (BSA) or highly purified gelatine (Gibco) at 0-10 μg/well were used to construct a standard curve. The protein content of samples were determined from this standard curve.

Analysis of Proteins by SDS-PAGE Electrophroresis

The method used is based on that described by Laemmli (Laemmli U K. Clevage of structural protein during the assembly of the head bacteriophage T4. Nature. 1970; 227:680-685). Briefly samples were mixed 1:1 with 2× sample loading buffer (0.07 M TrisHCl, 1.5% SDS, 20% glycerol, 0.2M DTT and 0.1% BPB) to achieve the final concentrations of between 4.0-20 mg/ml. The mixture was boiled in a water bath for 5 min. 20 μl of solution were loaded into the wells of 8-16% pre-cast Tris-glycine gel (Norvex). SeeBlue pre-stained low molecular weight range protein markers (Norvex) were loaded into wells on the left-hand side of the gel and electrophoresis was performed at 125 V for 2 h. The gel was stained in Coomassie blue R250 solution (40% ethanol, 10% acetic acid and 0.2% Coomassie R250) for 30 min and destained in a solution containing 10% ethanol and 7.5% acetic acid for 16 h. The gel was dried in a Bio-Rad Gelair drier.

Sulfated Glycosaminoglycan (S-GAG) Assay Using the DMMB Dye

The sulfated glycosaminoglycan (S-GAG) concentrations in samples were determined using a colorimetric dye binding assay modified from that described by Farndale et al. (Farndale R W, Buttle D J, Barrett A J. Improved quantitation and discrimination of sulphated glycosaminoglycans by use of dimethyl methylene blue. Biochem. et. Biophys. Acta. 1986; 883:173-177).

The assay is based on a metachromatic shift in absorption maxima from 690 nm to 535 nm when a complex is formed between a mixture of 1,9-dimethylmethylene blue (DMMB) and the sulfated-GAG in the sample or in a standard solution. The dye solution was made by adding 16 mg of 1,9-dimethylmethylene blue to 5 ml ethanol to 2 g of sodium formate and 2 ml of formic acid in a total volume of 1 liter at pH 3.5. Chondroitin-6-sulfate (CS—C) standards (0-15 and 0-40 µg/ml: 50 µl) or samples (50 µl) were transferred to a microtitre plate. The dye solution (200 µl) was added immediately to each well and absorbance was measured at 540 nm, immediately as a precipitate will form on standing. A standard curve was plotted using the absorption of samples of known CS-C concentration and the plate reader software. The concentration of the S-GAG in the unknown samples were determined from the CS-C standard curve.

Hyaluronan (HA) ELISA

Ninety six well microtiter plates (Maxisorp®, Nunc) were coated at 4° C. overnight with umbilical cord HA (Sigma Chemical Co) (100 µl/well) dissolved in the coating buffer. Uncoated areas were then blocked with 150 µl/well of 1% (w/v) BSA in phosphate buffer saline (PBS) for 60 min at 25° C. After washed with PBS-Tween, 100 µl of the samples to be assayed or standard competitor (HA Healon®: range 19.53-10,000 ng/ml) together with Biotin conjugated-HA-binding protein (1:200) were added. After incubation for 60 min at 25° C., plates were washed and then a peroxidase-mouse monoclonal anti-biotin (Invitrogen) (100 µl/well; 1:4,000) was added and the mixture incubated for 60 min at 25° C. The plates were washed again and then a peroxidase substrate (Invitrogen) (100 µl/well) was added and incubated at 37° C. for 10-20 minutes to allow the color to develop. The reaction was stopped by addition of 50 µl of 4 M H2SO4. The absorbance ratio at 492/690 nm was measured using the Titertek Multiskan M340 multiplate reader.

Semi-Quantitative RT-PCR mRNA

Total RNA was isolated from Progenitor cells according to the manufacturer's instructions for the Aurum total RNA mini kit (Bio-Rad, USA). The RNA was reverse transcribed with RevertAid™ H Minus First Stand cDNA Synthesis Kit (Fermentas, USA). Table 21 and 2 show the primer sequences and condition used for PCR. PCR products were transferred to an agarose gel, and visualized by ethidium bromide staining, and integrated densities calculated using Scion image analysis software, normalized to the housekeeping gene Glyceraldehydes-3-phosphate dehydrogenase (GAPDH) to permit semi-quantitative comparisons in mRNA levels. (L. Marchuk, P. Sciore, C. Reno, C. B. Frank, D. A. Hart. Postmortem stability of total RNA isolated from rabbit ligament, tendon and cartilage, Biochim Biophys Acta. 1379 (1998) 171-177. R. Boykiw, P. Sciore, C. Reno, L. Marchuk, C. B. Frank, D. A. Hart. Altered levels of extracellular matrix molecule mRNA in healing rabbit ligaments, Matrix Biol. 17 (1998) 371-378.)

TABLE 1

Primers for Murine Reverse-Transcript PCR

| Gene (Murine) | Primer Sequence | SEQ ID NO: | Tm | Cycles | Product Size | Protocol |
|---|---|---|---|---|---|---|
| GADPH | F: 5'CAC CAT GGA GAA GGC CGG GG 3' | 25 | 55 | 28 | 418 | RT130308 |
|  | R: 5'GAC GGA CAC ATT GGG GGT AT 3' | 26 |  |  |  |  |
| SOX-9 | F: 5'CTG AAG GGC TAC GAC TGG AC 3' | 27 | 58 | 28 | 406 | RT040308 |
|  | R: 5'GAG GAG GAA TGT GGG GAG TC 3' | 28 |  |  |  |  |
| Aggrecan | F: 5'AGG AGG TGG TAC TGC TGG TG 3' | 29 | 55 | 28 | 448 | RT130308 |
|  | R: 5'TCT CAC TCC AGG GAA CTC GT 3' | 30 |  |  |  |  |
| Type II Collagen | F: 5'AGT CAA GGG AGA TCG TGG TG 3' | 31 | 58 | 28 | 598 | RT040308 |
|  | R: 5'CGT CGT GCT GTC TCA AGG TA 3' | 32 |  |  |  |  |
| ALPH | F: 5'GCC CTC TCC AAG ACA TAT A 3' | 33 | 55 | 28 | 372 | RT130308 |
|  | R: 5'CCA TGA TCA CGT CGA TAT CC 3' | 34 |  |  |  |  |

TABLE 2

Primers used for semi-quantitative RT-PCR

| Gene (HUMAN) | Annealing temp (° C) | Product size (base pairs) | Sequences (5' to 3') | SEQ ID NO: |
|---|---|---|---|---|
| Aggrecan | 65 | 110 | Forward: ACTTCCGCTGGTCAGATGGA | 35 |
|  |  |  | Reverse: TCTCGTGCCAGATCATCACC | 36 |
| Collagen II | 65 | 106 | Forward: CAACACTGCCAACGTCCAGAT | 37 |
|  |  |  | Reverse: CTGCTTCGTCCAGATAGGCAAT | 38 |

TABLE 2-continued

Primers used for semi-quantitative RT-PCR

| Gene (HUMAN) | Annealing temp (° C) | Product size (base pairs) | Sequences (5' to 3') | SEQ ID NO: |
|---|---|---|---|---|
| SOX9 | 68 | 101 | Forward: ACACACAGCTCACTCGACCTTG<br>Reverse: GGAATTCTGGTTGGTCCTCTCTT | 39<br>40 |
| hsp 70 | 60 | 590 | Forward: TTTGACAACAGGCTGGTGAACC<br>Reverse: GTGAAGGATCTGCGTCTGCTTGG | 41<br>42 |
| HAS1 | 65 | 348 | Forward: CGGCCTGTTCCCCTTCTTCGTG<br>Reverse: TCGTGTGCTACGCTGCGGACCA | 43<br>44 |
| HAS2 | 51 | 358 | Forward: CACAGCTGCTTATATTGTTG<br>Reverse: AGTGGCTGATTTGTCTCTGC | 45<br>46 |
| HAS3 | 55 | 317 | Forward: CAGCCTCCTCCAGCAGTTCC<br>Reverse: TAACCGTGGCAATGAGGAAG | 47<br>48 |
| HYAL1 | 51 | 208 | Forward: AGCTGGGAAAATACAAGAACC<br>Reward: TGAGCTGGATGGAGAAACTGG | 49<br>50 |
| HYAL2 | 55 | 448 | Forward: GAGTTCGCAGCACAGCAGTTC<br>Reward: CACCCCAGAGGATGACACCAG | 51<br>52 |
| HYAL3 | 65 | 500 | Forward: CCGCCTCCAGTGCCCTCTTCC<br>Reward: AGCCCAGCCCCAGTAACAGTG | 53<br>54 |
| MMP-1 | 68 | 84 | Forward: CTGTTCAGGGACAGAATGTGCT<br>Reverse: TCGATATGCTTCACAGTTCTAGGG | 55<br>56 |
| MMP-2 | 56 | ~100 | Forward: TCAAGTTCCCCGGCGAT<br>Reverse: TGTTCAGGTATTGCACTGCCA | 57<br>58 |
| MMP-3 | 65 | 138 | Forward: TTTTGGCCATCTCTTCCTTCA<br>Reverse: TGTGGATGCCTCTTGGGTATC | 59<br>60 |
| MMP-9 | 56 | ~100 | Forward: TGAGAACCAATCTCACCGACAG<br>Reverse: TGCCACCCGAGTGTAACCAT | 61<br>62 |
| MMP-13 | 65 | 96 | Forward: TCCTCTTCTTGAGCTGGACTCATT<br>Reverse: CGCTCTGCAAACTGGAGGTC | 63<br>64 |
| Human-iNOS | 60 | 340 | Forward: CAGTACGTTTGGCAATGGAGACTGC<br>Reverse: GGTCACATTGGAGGTGTAGAGCTTG | 65<br>66 |
| □5-Integrin | 55 | 324 | Forward: CATTTCCGAGTCTGGGCCAA<br>Reverse: TGGAGGCTTGAGCTGAGCTT | 67<br>68 |
| □1-Integrin | 55 | 452 | Forward: TGTTCAGTGCAGAGCCTTCA<br>Reverse: CTTCATACTTCGGATTGACC | 69<br>70 |
| Fibronectin Extra domain A | 56 | 143 | Forward: CAT TCA CTG ATG TGG ATG TC<br>Reverse: CAG TGT CTT CTT CAC CAT CA | 71<br>72 |
| Fibronectin Extra domain B | 56 | 129 | Forward: CCG CCA TTA ATG AGA GTG AT<br>Reverse: AGT TAG TTG CGG CAG GAG AAG | 73<br>74 |
| Total-fibronectin | 60 | 184 | Forward: GAT AAA TCA ACA GTG GGA GC<br>Reverse: CCC AGA TCA TGG AGT CTT TA | 75<br>76 |
| CD44 | 56 | 602 | Forward: GATCCACCCCAATTCCATCTGTGC<br>Reverse: AACCGCGAGAATCAAAGCCAAGGCC | 77<br>78 |
| ADAMTS1 | 60.4 | ~100 | Forward: GAACAGGTGCAAGCTCATCTG<br>Reverse: TCTACAACCTTGGGCTGCAAA | 79<br>80 |
| ADAMTS4 | 56 | ~100 | Forward: CAAGGTCCCATGTGCAACGT<br>Reverse: CATATGCCACCACCAGTGTCT | 81<br>82 |
| ADAMTS5 | 60.4 | ~100 | Forward: TGTCCTGCCAGCGGATGT<br>Reward: ACGGAATTACTGTACGGCCTACA | 83<br>84 |
| GAPDH | 53 | 370 | Forward: TGGTATCGTGGAAGGACTCAT<br>Reward: GTGGGTGTCGCTGTTGAAGTC | 85<br>86 |

Separation of Peptacan Proteins/Polypeptides Using Dowex MAC3 Cation Exchange Resin The Dowex MAC3 resin (100 grams) (Sigma Chemical Co) was regenerated as the hydrogen form over 24 hours using 4% HCl. By means of a sinter-glass filter the resin was thoroughly washed (3×2 L H2O) then equilibrated with 0.1M calcium acetate adjusted to pH 4.5. The Peptacan (10 grams) was dissolved in 0.1M calcium acetate, pH 4.5 at a concentration of 5 mg/ml then mixed with the resin and gently agitated for 1 hr. The solution containing the non-bound S-GAGs and proteins was separated from the resin by filtration and the resin washed with loading buffer (10× resin volume) until no S-GAGs could be detected using the Farndale et al assay. The resin was further washed several time, with Milli-Q water and then equilibrated with 0.2M Na2HPO4. The proteins bound to the resin were released by a solution of 0.2M Na2HPO4 adjusted to pH 10.5 with NaOH. The resin was again separated by filtration through a sinter-glass Buchner funnel, the filtrate was collected and diafiltrated using a 1 KDa TFF membrane (Millipore Australia Pty Ltd, Sydney, Australia) then freeze dried.

Separation of Peptacan Proteins/Polypeptides Using the Cetylpyridinium Chloride (CPC) Precipitation Method Cetyl pyridinium chloride (CPC) is a water soluble surfactant which forms strong water insoluble complexes between its positively charged pyridinium ion and the negatively charged sulfate groups present on the sulfated glycosaminoglycan (S-GAG) components of Peptacans.

These water insoluble CPC-S-GAG complexes have been extensively used over the last 40 years by many investigators to isolate and purify S-GAGs from extracts of biological tissues or fluids. However, we reasoned that this principle could also be used to isolate the proteins/polypeptides present in the Peptacans, since after precipitation and removal of the CPC-S-GAG complexes the Peptacan proteins would be left in the filtration liquors. The procedure used for the CPC-S-GAG precipitation step was based on the method described by Oegema and Thompson (Oegema T R and Thompson R C. Characterisation of a hyaluronic acid-dermatan sulfate proteoglycan complex from dedifferentiated human chondrocyte cultures. J Biol Chem. 256:1015-1022; 1981) but modified by using 2M calcium chloride to dissociate the GAG-CPC complex and precipitating the S-GAGs from aqueous solution with 4× the aqueous volume of ethanol. The aqueous solution containing the Peptacan proteins/polypeptides, after removal of the CPC-S-GAG complex was extensively diafiltration using a 1000 Da cut-off ultrafiltration membrane (YC10) or a tangental flow ultrafiltration (TFF) cartridge of similar MW cut-off (Millipore Australia Pty Ltd, Sydney, Australia). However, in the final stages of diafiltration the dialysing solution was replaced by 0.001 M acetic acid to avoid precipitation of the proteins. The diafiltrated solutions were freeze-dried to afford the protein/polypeptides as a white powder.

Preparation of rhNC4 Using a Bacterial System.

The gene of NC4 of human collagen IX without the 23 signal peptide was constructed on the pGAT-2 bacterial expression vector in-frame with the sequences for the GST fusion tag based on a previously described method (Pihlajama T, et al. Characterization of Recombinant Amino-terminal NC4 Domain of Human Collagen IX: Interaction with glycosaminoglycans and cartilage oligomeric matrix protein. J. Biol. Chem. 2004; 279: 24265-24273). The recombinant human NC4 (rhNC4) construct was transferred into a *Escherichia coli* BL21 (DE3) cell line. The fusion protein was expressed in shaker flasks by inoculating (1:100) the cell line into the desired final volume of LB medium supplemented with 100 microg/ml ampicillin. The cells were grown at 37° C. until absorbance at 600 nm reached the value 0.6. The expression was induced by addition of isopropyl-beta-D-thiogalactopyranoside (IPTG) to afford a final concentration of 0.5 mM. The incubation was continued at 37° C. for 4-6 hrs or 16 hrs. Following centrifugation, the cell pellets were washed by 1×PBS for three times and resuspended with homogenisation buffer [0.3 M NaCl, 0.2% IGEPAL CA-630 (Sigma, Sydney, Australia), 0.05 M sodium phosphate buffer (pH 7), 0.25 mg/ml lysozyme], then stored frozen and later homogenized on ice by sonication. Insoluble material was removed by centrifugation at 17,000 g for 40 min at 4° C. The fusion protein was precipitated from the supernatant by adding ammonium sulphate to 30% saturation. The precipitate was collected by centrifugation at 23,000 g for 30 min at 4° C. and dissolved in 1×PBS (with 1% IGEPAL-CA 630). The solution was clarified by centrifugation at 23,000 g for 30 min at 4° C., and applied to a column of glutathione-Sepharose 4 FF (Amersham Biosciences, Sydney, Australia) at 4° C. with the flow-rate of 250 µl/min. In order to remove the endotoxin, 50 column volumes (CV) of 1×PBS (containing 0.1% Triton X-114) was applied to remove the unbound material and followed by washing with 20 CV of 1×PBS (sterile) (Reichelt P, Schwarz C and Donzeau M. Single step protocol to purify recombinant proteins with low endotoxin contents.

Protein Expression and Purification 46: 483-488, 2006). After equilibrated with 10 CV of the factor Xa cleavage buffer (sterile), the recombinant NC4 (rNC4) was cleaved off from the fused GST by overnight digestion with Factor Xa protease (Amersham Biosciences or Promega) at room temperature. The rhNC4 solution migrated through the column of glutathione-Sepharose with the elution of Benzamidine Sepharose 4 FF binding buffer (50 mM Tris-HCl, 100 mM NaCl, pH 7.4), and was subjected to further purification using a Benzamidine Sepharose 4 FF column (Amersham Biosciences). The flow-through rhNC4 was concentrated and desalted by washing with dH$_2$O in a 5K cut-off concentrator (Agilent Technologies). Final purification was achieved by size exclusion chromatography using a Superdex S-200 column. The size and purity of the product was determined by SDS-PAGE analysis and western blotting. The concentration of purified rhNC4 was determined using the Bradford (Sigma, Sydney, Australia) or the BCA protein assays.

Expression of human NC4 in Yeast *K. lactis*

(i) Isolation of the Collagen α1 (IX) NC4 Domain Gene

The gene of NC4 of human collagen IX (GenBank accession number NM_001851) without the 23 signal peptide was obtained by reverse-transcription PCR with RNA extracted from human chondrocyts from articular cartilage. Human chondrocyts were seeded in alpha-MEM medium supplemented with 10% FCS. When the cells were confluent, they were trypsinized and collected as a cell pellet by centrifugation. Total RNA was extracted from the cell pellet with RNeasy® Mini Kit (QiaGen Pty Ltd, Melbourne, Australia). Reverse transcription PCR was performed with SuperScript™ One-Step RT-PCR with Platinum Taq (Invitrogen, Melbourne, Australia) according to manufacturer's instructions. The upstream and downstream primers were KL-NC451 and KL-NC431 (Table 1), respectively. cDNA synthesis was undertaken using 1 cycle of 55° C. for 30 min followed by 2 min, 94° C. pre-denaturation, and 40 cycles of PCR amplification (Denature: 94° C. for 30 sec; Anneal: 55° C. for 30 sec; Extend: 72° C. for 1 min). The RT-PCR products were separated by 0.8% agarose gel and purified with SNAP™ Gel Purification (Invitrogen, Melbourne, Australia).

(ii) Construction of the Vector for Expressing the Collagen α1 (IX) NC4 Domain in Yeast The *K. lactis* expression system (New England Biolab, USA) was applied to generate a DNA construct for expression of the NC4 domain of the human α1 (IX) collagen (hNC4) in yeast *Kluyveromyces lactis*. A group of oligonucleotide primers (Table 1) were designed to amplify a fragment of amino acids 24-268 of the full-length hNC4 (NCBI accession number NP_001842), which omited the 23-amino acid signal peptide.

TABLE 1

Primers used for construction of pKLAC1-NC4 expression vectors

| Name | Primers | SEQ ID NO: |
|---|---|---|
| KL-NC451 | 5'-ACTCTCGAGAAAAGAGCTGTCAA GCGTCGC-3' | 87 |
| KL-NC431 | 5'-GTCAGATCTTTATCTCTCGTCGG TGGTCTG-3' | 88 |
| KL-NC454 | 5'-ACTCTCGAGAAAAGAGCTGTTAA GCGTAGACCAAGATTCC-3' | 89 |
| KL-NC433 | 5'-GTCAGATCTTCATTATCTCTCGT CGGTAGTCTGGCTTGGAGTAATTCTG GCTGGCAGCTCATGGCAAGTTTCTCT CCTAGGTCTCAGTGG-3' | 90 |
| KL-NC438 | 5'-CTGAGATCTACCAGGTGGACCTC TTCCATCGGTAGTTTGAC-3' | 91 |
| GAT2-GST53 | 5'-CTGAGATCTGGTGCTGGTGCTAT GACTAAGTTACCTATACTAGGTTATT GG-3' | 92 |
| GAT2-GST33 | 5'-ACTGTCGACTTAGTCATTAATGA TCAGATTTTGGAGGATGATCTCCAC C-3' | 93 |

The 5'-primer KL-NC451 contained an engineered Xho I cleavage site, and the 3'-primer KL-NC431 contained an engineered Bgl II cleavage site. With these two primers, the hNC4 fragment without the signal peptide was amplified by reverse transcription PCR.

The 5'-primer KL-NC454 and the 3'-primer KL-NC433 contained engineered Xho I and Bgl II cleavage sites, respectively. Different from primer KL-NC451 and primer KL-NC431, KL-NC454 and KL-NC433 provided a number of gene mutations that changed the hNC4 gene according to yeast *K. lactis* preferred codons but preserved the hNC4 protein sequence unchanged.

The PCR products of hNC4 were digested by restriction enzymes and ligated to the pKLAC1 expression vector (FIG. 1) at the multiple cloning sites Xho I and Bgl II. The positive inserted recombinants were sequenced to confirm that the NC4 gene insert was correct. The correct recombinants were digested by restriction enzyme Sac II and transformed to competent *K. Lactis* GG799 cells. Yeast carbon base (YCB) medium containing 5 mM acetamide as a source of nitrogen was used as a selective medium. Only after the Sac II fragments of the recombinants with the target NC4 genes and amdS gene (amdS gene present in pKLAC1) have been integrated to the yeast chromosome DNA did the cells survive in this selective YCB medium.

The 5'-primer GAT2-GST53 and the 3'-primer GAT2-GST33 were designed to obtain a glutathione-S-transferase (GST) gene from the bacterial vector pGAT-2 with some mutations for expression in yeast *K. lactis*. This GST gene, which had three STOP translation codons at the 3'-terminal, was constructed in the vector pKLAC1 multiple cloning sites Bgl II and Sal I to form pKLAC1-GST.

The 5'-primer KL-NC454 and the 3'-primer KL-NC438 were designed for a recombinant hNC4 that had a mutation converting the $Glu^{267}$ to Gly. This mutation provided a thrombin cleavage site at the C-terminal of hNC4. The recombinant hNC4 was ligated to the vector pKLAC1-GST at cloning sites Xho I and Bgl II, so that an N-terminal GST fusion protein was obtained. After DNA sequence confirmation, the recombinant with NC4-GST fusion protein gene was digested with Sac II and inserted to the chromosome DNA of yeast *K. lactis* GG799 cell, then screened by YCB selective medium for the survival colonies with integrated NC4 and amdS genes.

(iii) Expression of the Collagen α1 (IX) NC4 Domain in Yeast *K. lactis* GG799 Cells Cells from each colony that contains an integrated expression hNC4 were harvest from an area approximately 2 mm² by scraping with a sterile toothpick or pipette tip and resuspend them in 2 ml of YPGal medium (10 g Yeast Extract, 20 g Bacto™ Peptone, 2% Galactose) in a sterile culture tube. The cultures were incubated with shaking (~250 r.p.m.) at 30° C. for a minimum of 2 days growth. Analysis of culture supernatant was performed each day to determine the optimum growth time to achieve maximum secretion of NC4. Larger cultures (e.g., ≥1 L) for protein purification were inoculated 1:100 with a starter culture grown overnight at 30° C. Samples (1 ml of each culture) were centrifuged for 1 minute at 10,000 g to pellet the cells. The culture supernatant were transferred to a fresh microcentrifuge tube and stored on ice. Thirty μl of the unconcentrated culture supernatant was applied to SDS-PAGE (NuPAGE 4-12% Tris-Bis Gel, MES buffer, Invitrogen) followed by Coomassie staining (Colloidal Blue Stain Kit, Invitrogen) and/or Western blotting.

(iv) Partial Purification of rhNC4 Protein Expressed From Yeast *K. Lactis* GG799

Three-day cultures with volumes >1 L which were to used for protein purification were filtered with Celite-512 to remove the cells and debris. The clear aqueous filtrates were diafiltrated and concentrated by application to a 10 KDa cut-off Tangential Flow Filtration (TFF) membrane (Millipore Ltd, Sydney, Australia). Following 2×5 volumes of 50 mM sodium phosphate buffer (pH7.4) diafiltration, the culture medium solution was concentrated to 1-2 L and stored at 4° C. overnight or immediately proceeded by $(NH_4)_2SO_4$ precipitation. Solid $(NH_4)_2SO_4$ was added to the culture medium solution to 80% saturation (0° C.). The precipitate was collected by centrifuge at 14,000 g, 30 min, 4° C., and dissolved in 50 mM sodium phosphate buffer (pH7.4). The protein concentration of purified hNC4 was determined using the Bradford or BCA (Sigma, Sydney, Australia) assays. Additional purification of this material was undertaken using the same methods as described herein for the rhNC4 prepared from *E. coli*.

Cryopreservation of Progenitor Cells in the Presence of Various Concentrations of Pentosan Polysulfate (PPS)

Cells were harvested and resuspended in cold serum free culture medium at 5.0 to 20.0×10⁶ cells/ml. An equal volume of chilled complete Profreeze®-CDM medium was added to the chilled cell suspension containing 0, 10, 20, 50 and 100 micrograms/mL of PPS. The resulting final DMSO concentration was 7.5%, PPS concentration was 0, 5, 10, 25 and 50 micrograms/mL and the final cell concentration was approximately 2.5 to $10 \times 10^6$ cells/ml. The cell mixture was aliquoted into cryopreservation ampoules (Nunc, Intermed, Denmark) and cryopreserved in a C156 Freezing Container (Thermo Scientific, Melbourne, 21 Australia) at −80° C. for a −1° C./minute controlled cooling rate. The ampoules were then transferred to liquid nitrogen storage (−196° C.).

Thawing of Cyropreserved Samples

Cyropreserved cells were rapidly thawed for a minute in a 37° C. water bath and transferred to a 10 mL polypropylene tube. Approximately 3 mL of appropriate media was added dropwise to the cells with constant mixing, and made up to a final volume of 10 mL. Cells were pelleted by centrifugation at 400×g, 4° C. for 5 minutes and the supernatant aspirated. To ensure removal of residual DMSO, cells were washed in medium and centrifuged as above. Cells were resuspended in final volume of 10 mL and seeded in a 75 cm² flask prior to incubation in a humidified incubator at 37° C. in the presence of 5% CO2.

Enumeration of Cells After Cryopreservation in the Presence of Various Concentrations of Pentosan Polysulfate (PPS).

Aliquots of single-cell suspensions obtained after thawing progenitor cells from the PPS containing cryopreserved vials were diluted in an equal volume of 0.4% (w/v) trypan blue in phosphate buffered saline (PBS). The cell counts were determined using a haemocytometer (Neubauer Improved, Assistant, Germany) and a light microscope (Olympus CKX41, Japan).

The results of this experiment is shown in FIG. 1. In general, it can be seen that the addition of PPS did not have an adverse effect on the cryopreservation of the progenitor cells.

With the exception of 30 minutes, the use of 50 μg/ml PPS enhanced the viability of the progenitor cells at all time points. The use of 25 μg/ml PPS either enhanced the viability or did not adversely affect the viability of the progenitor cells at all time points instead of 30 minutes. The use of 10 μg/ml PPS had a beneficial effect at time point 0 and then at 60 and 90 minutes. The use of 5 μg/ml PPS had a beneficial effect on viability at 60 minutes.

Overall, it can be seen that in general, the addition of PPS did not have an adverse effect and may enhance the cryopreservation of progenitor cells. The slight differences in values may be attributable to the method used to count the cells. Because the progenitor cells tend to clump, this may lead to errors which would account for the apparent lower values with 5 micrograms PPS where clumping was common.

Concentration Determined Effects of Pentosan Polysulfate (PPS) on the Viability of ProgenitorCells Following Cryopreservation and Thawing Using the MTT Assay Murine Progenitor cells (cell lines C3H10T1/2 or ATDC5) purchased from RIKEN Cell Bank (Tsukuba, Japan) or human immunoselected Stro-1+ progenitor cells (Mesoblast Ltd, Melbourne, Australia) were seeded at a various cell densities over the range of $1.68 \times 10^5$-$1.0 \times 10^6$ cells into 2 mL screw-capped centrifuge tubes containing in DMEM+10% FBS. In separate tubes a stock solution containing 2× the required concentrations of PPS dissolved in DMEM+20% FBS and 15% DMSO were prepared. These stock solutions were added to the cell cultures such that the final concentration of PPS was half that of the stock concentration and of FBS was 10% and DMSO was 7.7%. Over several independent experiments the final concentrations of PPS in the final solutions ranged from 0.0-100 ug/ml (see figures for details). All concentrations of PPS used were examined in triplicated. Cells and the cryopreservation solutions containing the PPS were mixed gently for 5 mins and stored in liquid nitrogen. After 3 days, the tubes were removed from liquid nitrogen and thawed in 37° C. water bath and allowed to stand at ambient temperature for about 15 min. The cells were centrifuged down at 200 g for 5 min and the supernatant discarded. The cells were washed with 900 ul of DMEM without phenol red, and then centrifuged down at 200 g for 5 min. The cells were resuspended in 500 ul of 1 mg/ml MTT solution in DMEM and incubated in 37° C. for 3 hours then centrifuged at 6000 g for 5 min. 300 ul of DMSO was added to each tube to dissolved the dye crystals. 90 ul×3 from each tube were transferred to a 96-well plate and the absorbance at 540 nm determined.

Figure 2:
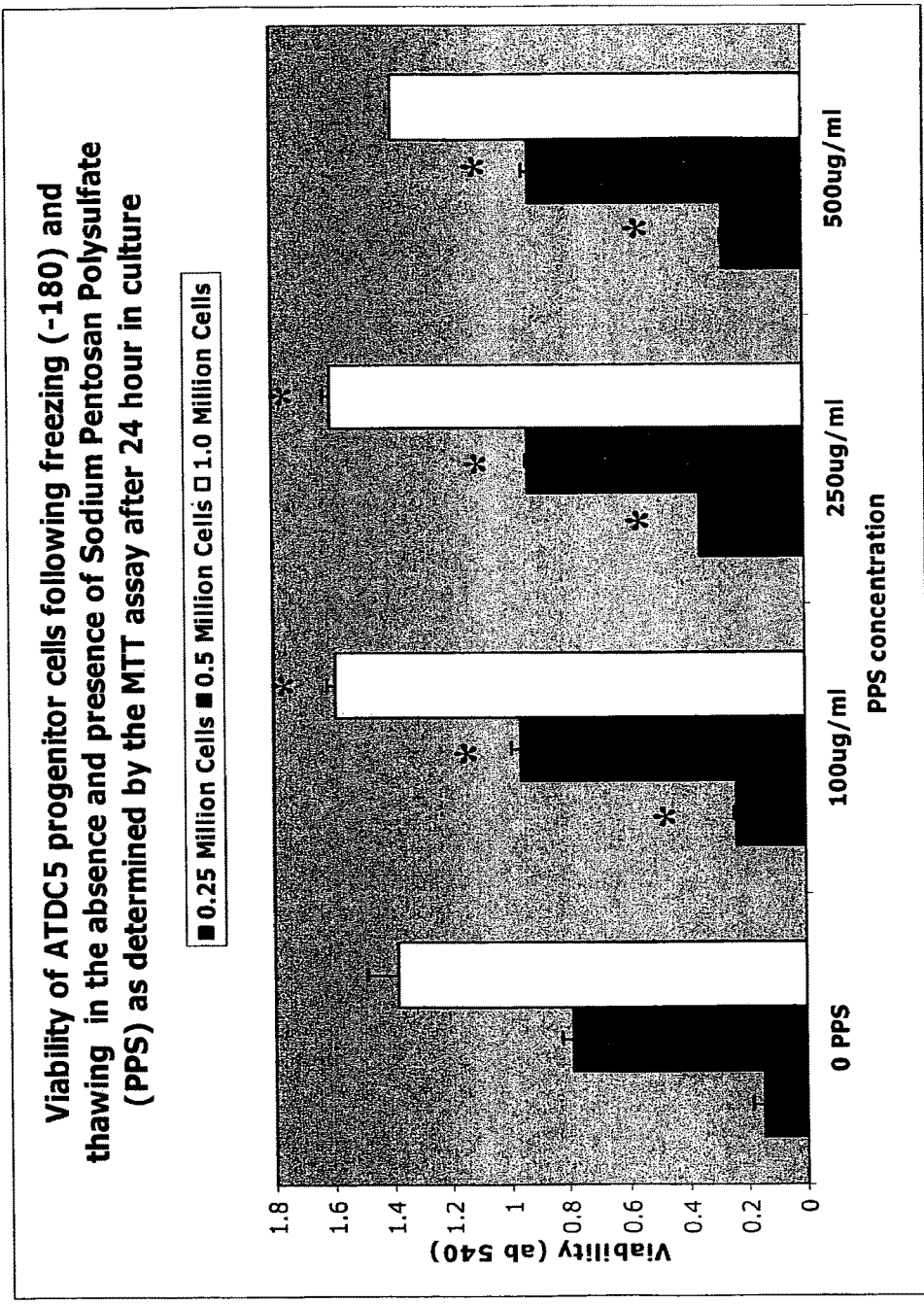
FIG. 2. Bar graph showing the viability of different numbers of murine ATDC5 progenitor cells suspended in cryogenic media containing 7.5% DMSO and various concentrations of Pentosan Polysulfate (PPS) after being subjected to freeze-thawing cycle. Cell viability was determined using the mitochondrial dehydrogenase MTT assay.

FIG. 2 shows a bar graph showing the viability of different numbers of murine ATDC5 progenitor cells suspended in cryogenic media containing 7.5% DMSO and various concentrations of Pentosan Polysulfate (PPS) after being subjected to freeze-thawing cycle. Cell viability was determined using the MTT assay.

FIG. 2 shows that the viability of the progenitor cells were enhanced by the presence of PPS at all concentrations. At 100 μg/ml PPS the viability was enhanced at cell counts of 0.25 million, 0.5 million and at 1.0 million cells. The same is seen with 250 μg/ml PPS. For 500 μg/ml PPS, enhancement is seen for 0.25 million and 0.5 million cells. For 1 million cells, a concentration of 500 μg/ml PPS did not appear to enhance viability but was not detrimental to viability.

By extrapolation of these data it is may be assumed that a dosage of 100 million of chondroprogenitor cells together with 25-50 mg PPS when subjected to a freeze-thawing cycle in an appropriate cryoprotective medium would maintain the viability of the cells to a level for acceptable administration to a patient in need of such therapy.

FIG. 3 shows the effects of different concentrations of Sodium Pentosan Polysulfate (PPS) on human progenitor cell viability following cryopreservation at −180° C. and thawing as determined using the MTT assay. Data shown=Means±SD *=p<0.05 relative to control values.

When cryopreserving 168,000 cells, the presence of PPS improved the viability of the cells, particularly at 1 and 2.5 μg/ml PPS. With 350,000 cells, it can be seen that in general, viability of the progenitor cells is not adversely affected by the presence of PPS. In some cases, viability of the cells is enhanced after thawing.

By extrapolation of these data it is may be assumed that a dosage of 100 million human progenitor cells together with 30 mg PPS when subjected to a freeze-thawing cycle in an appropriate cryoprotective medium would maintain the viability of the cells to a level for acceptable administration to a patient in need of such therapy.

Effects of Pentosan Polysulfate (PPS) on Human Progenitor Cells Apoptosis Induced by the Addition of a Combination of IL-4 IFN-Gamma as Determined by Flow Cytometry.

Human progenitor cells were plated in serum-free media supplemented with PPS at concentrations of 0, 1, 2, 5 and 10 micrograms/mL. Progenitor cell apoptosis was induced by the addition of a combination of 30 ng/ml IL-4 30,000 U/ml IFN gamma. Following 5 days culture, cells were harvested by trypsinisation and viabilities assessed by Annexin V staining as previously described (Kortesidis A, A Zannettino, S Isenmann, S Shi, T Lapidot and S Gronthos. (2005). Stromal-derived factor-1 promotes the growth, survival, and development of human bone marrow stromal stem cells. Blood 105:3793-3801).

The results for this experiment is shown in FIG. 6. It can be seen that cell apoptosis is reduced for all concentrations of PPS with the best results seen for 10 µg/ml. These results indicate that the addition of PPS into the cryopreservation medium will reduce apoptosis on thawing.

The experiment was undertaken in a 96 well plate containing 50,000 progenitor cells/well. Without wishing to be bound by theory it is believed that apoptosis and activation of the stress protein cascade is a recognised sequence of cell freeze-thawing and therefore the ability of PPS to significantly reduce this process must be of benefit to the use of these cells following cryopreservation and thawing as required in most cell based medical procedures.

Effects of Sodium Pentosan Polysulfate (PPS) Alone or in Combination With rhNC4 on the Biosynthesis of Proteoglycans (Measured as $^{35}$S-GAGs) by Progenitor Cells Grown in Monolayer Cultures Murine Progenitor cells (cell lines C3H10T1/2 or ATDC5) purchased from RIKEN Cell Bank (Tsukuba, Japan) or human immunoselected Stro-1+ Progenitor cells (Mesoblast Ltd, Melbourne, Australia) were seeded into 50 mL plastic culture flasks containing 1:1 high glucose DMEM/Ham's F-12 medium (Invitrogen) supplemented with 10% FBS (Sigma) and incubated at 37° C., in 5% $CO_2$. After confluence was reached, progenitor cells were released by trypsinization and harvested by centrifugation. Cells were inoculated to 96-well or 24-well plates at a density of $3 \times 10^4$ cells or $2 \times 10^5$ cells per well. After 48-hour incubation at 37° C., 5% $CO_2$ confluent monolayers were normally established. The medium was then changed to defined medium, which contained different concentrations of PPS with and without rhNC4 and 5 µCi/ml of $^{35}$S—$H_2SO_4$ (PerkinElmer, USA). The experiments were generally terminated after 48 hours incubation when proteoglycan biosynthesis was determined by measuring the incorporation of $^{35}SO_4$ into the glycosaminoglycans ($^{35}$S-GAGs) as described below.

(A) 96-well plates: Cultures were subjected to proteolytic digestion with papain to release glycosaminoglycans. The papain stock solution used contained 2.5 mg/ml papain (Sigma), 7.9 mg/ml cysteine-HCl (Sigma) in papain digest buffer (0.1M NaAc, 5 mM EDTA, pH6.0). 50 µl of papain stock solution was added to each well. The plate was sealed using plastic sheeting and incubated at 65° C. for 2 hours. On termination, aliquots of 50 µl digested solution per well were collected for DNA fluorometric assay using Hoechst 33258 Dye and the method described by Kim et al (Kim Y J, Sah R L Y, Doong J-Y H, Grodzinsky A J, Fluorometric assay of DNA in cartilage explants using Hoechst 3358. Anal Chem. 1988; 174: 168-176).

The $^{35}SO_4$-GAGs in the remained solution (200 ul) were precipitated with Cetyl Pyridinium Chloride (CPC) (Sigma). Briefly, to each well was added 20 µl of 5% CPC, followed by 10 µl of 1 mg/ml Chondroitin sulfate A (CSA, Sigma) as a co-precipitant. The $^{35}$S-GAG-CPC complexes were collected by vacuum filtration using a cell harvester (Skatron 7021). The filters were then air-dried and discs punched into scintillation vials. Following addition of 3 ml scintillation liquid and vortexing the radioactivity of the $^{35}$S-GAG-CPC complexes were in the samples were measured by scintillation counting (PerkinElmer, USA) and recorded as DPM/sample. The data then was then normalised for DNA and expressed as $^{35}$-S-GAGs/µg DNA.

(B) 24-well plates: After 48 hours incubation in the defined media, the media per well (containing soluble $^{35}$S-labelled proteoglycans) was separated from the cells and transferred to a 2.0 ml microfuge tube. The monolayer cells remaining in the wells were detached by trypsinization, and then separated from the supernatant (containing matrix proteoglycans) by centrifugation at 350 g for 5 min. The supernatant was collected and combined with the medium. 200 µl of the medium and supernatant mixture was transferred to a 96-well plate and subjected to papain digest to release glycosaminoglycans. After papain digestion, 20 µl of 5% CPC was added to each well to precipitate the 35S-GAG followed by 10 µl of 1 mg/ml CSA as a carrier. The 35S-GAG-CPC complexes collected through the fibre filter and the radioactivity of 35S-GAG was measured using the liquid scintillation analyser as describe above. The cells were extracted with the RNA reagent and aliquots used to determine gene expression and/or the DNA content was measured by the fluorometric assay and the results expressed as $^{35}$-S-GAGs/µg DNA.

FIG. 4 shows the Effects of Pentosan Polysulfate on Human Progenitor cell Proliferation. Primary human progenitor cells were cultured in 24 well plates in growth media supplemented with PPS at the indicated concentrations. At various time intervals (day 1, 3, 6), the growth media was removed and replaced with phenol red free media containing the tetrazolium salt WST-1 for 2 hours at 37° C./5% $CO_2$. WST-1 is cleaved by mitochondrial dehydrogenase in viable cells to produce a formazan dye that can be detected using an ELISA plate reader at a wavelength of 450 nm. Absorbance at 450 nm for each time point is shown for all concentrations of PPS. A statistically significant increase in proliferation was observed on day 6 at concentrations of PPS in excess of 1 µg/ml (* $p<0.01$, ANOVA). FIG. 4 shows that progenitor cell viability was enhanced relative to progenitor cells frozen in cryo-preservation media not containing the polysulfated polysaccharide.

FIG. 9 shows the concentration dependent effects of Sodium Pentosan Polysulfate (PPS) on Murine Progenitor cell (C3H10T1/2) biosynthesis of Proteoglycans (PGs) and DNA content when grown in monolayer cultures. The data shown is Means±SD.

It can be seen that at all concentrations of PPS the biosynthesis of proteoglycans is increased. This shows that the use of polysulfated polysaccharides can induce differentiation, especially chondrogenesis at all concentration ranges. The best result is seen for 5-10 µl/ml, with 10 µl/ml being best with regards to PG synthesis and 5 µl/ml and 10 µl/ml being best with regard to DNA content.

Figure 10:
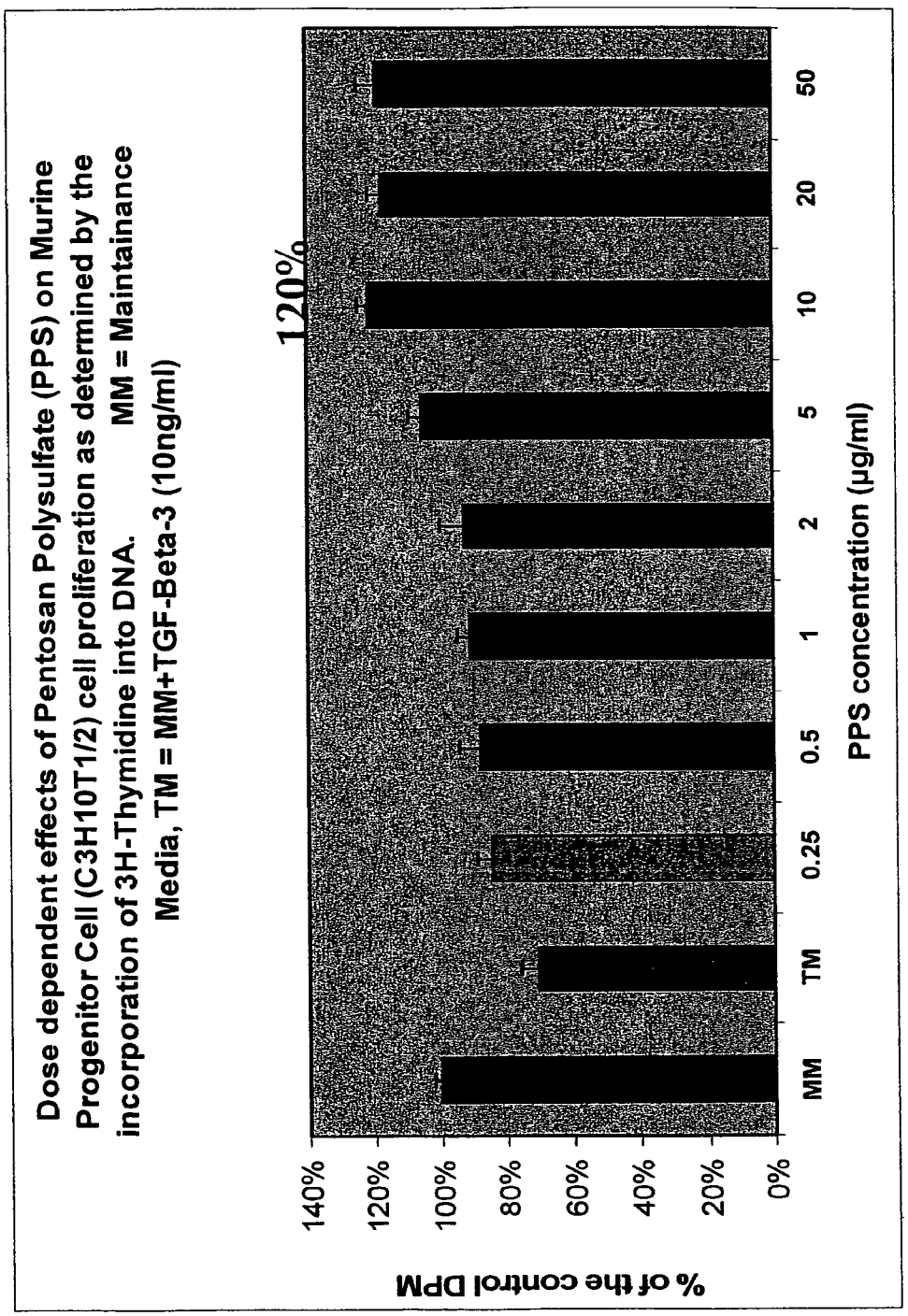
FIG. 10. A bar graph of the concentration dependent effects of Pentosan Polysulfate (PPS) on DNA synthesis by murine Progenitor Cells (C3H10T1/2 cells) grown in monolayer cultures for 2 days as determined by the incorporation of $^3$H-Thymidine into macromolecular DNA.

FIG. 10 shows a bar graph of the concentration dependent effects of Pentosan Polysulfate (PPS) on DNA synthesis by murine Progenitor cells (C3H10T1/2 cells) grown in monolayer cultures for 2 days as determined by the incorporation of $^3$H-Thymidine into macromolecular DNA.

Figure 11:
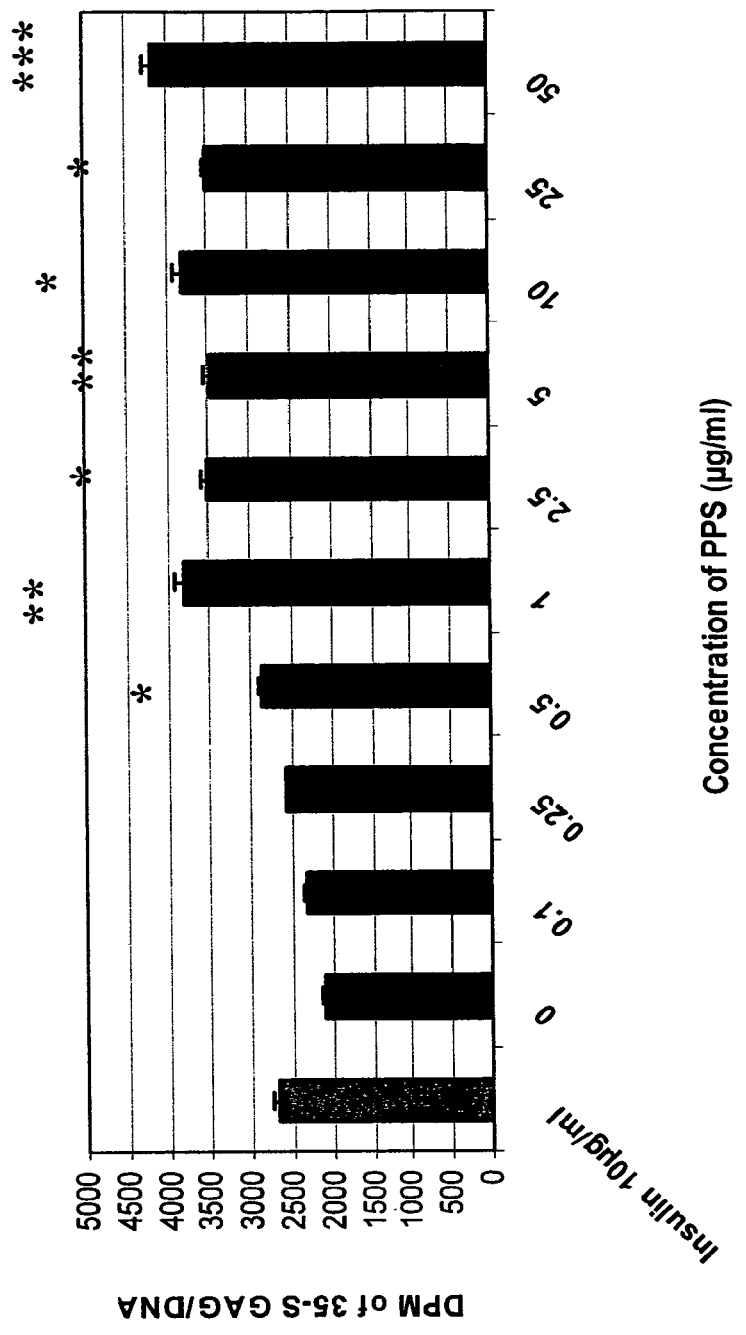
FIG. 11. A bar graph of the concentration dependent effects of Pentosan Polysulfate (PPS), on the biosynthesis of Proteoglycans (PGs) as determined by the incorporation of radioactively labelled sulfate into the sulfated glycosaminoglycans ($^{35}$S-GAG) of PGs after 2 day monolayer cultures of human progenitor cells. The data was expressed as $^{35}$S-GAG radioactivity as decays per minute (DPM) normalised to DNA content. *=p<0.05; =p<0.005; *=p<0.0005.

FIG. 11 shows a bar graph of the concentration dependent effects of Pentosan Polysulfate (PPS), on the biosynthesis of Proteoglycans PGs) as determined by the incorporation of radioactively labelled sulfate into the sulfated glycosaminoglycans ($^{35}$S-GAG) of PGs after 2 day monolayer cultures of human progenitor cells. The data was expressed as $^{35}$S-GAG radioactivity as decays per minute (DPM) normalised to DNA content. *=$p<0.05$; =$p<0.005$; *=$p<0.0005$.

FIG. 21 shows a bar graph of the concentration dependent effects of rhNC4 (batch PBA-1202P) expressed by *K. lactis*, in the absence (maintenance media, MM) and presence of insulin (10 micrograms/mL) (differentiation media, DM), on the biosynthesis of Proteoglycans (PGs) as determined by the incorporation of radioactively labelled sulfate into the sulfated glycosaminoglycans ($^{35}$S-GAG) of PGs after 3 day culture with Murine ATDC5 progenitor cells. The data was expressed as % change relative to control cultures that contained no rhNC4. P<0.05 was statistically significant relative to control cultures.

FIG. 24 shows the results for the combination of PPS and NC4. It can be seen that the effect of PPS increases with concentration. It can also be seen that this effect is enhanced in the presence of increasing concentrations of NC4.

The combination of 0.5 μl/ml of NC4 and 5 μl PPS showed a statistically significant increase in proteoglycan synthesis. In addition, the combination of 1 μl/ml NC4 and 2 μl/ml and 5 μl/ml PPS showed a statistically significant increase in proteoglycan synthesis. Furthermore, the combination of 2 μl/ml NC4 together with 1 μl/ml, 2 μl/ml or 5 μl/ml PPS or the combination of 5 μl/ml NC4 together with 1 μl/ml, 2 μl/ml or 5 μl/ml PPS all showed a statistically significant increase in proteoglycan synthesis.

The use of 5 μl/ml NC4 or 5 μl/ml PPS showed the best results with the combination of 5 μl/ml NC4 and 5 μl/ml PPS being best.

Figure 22:
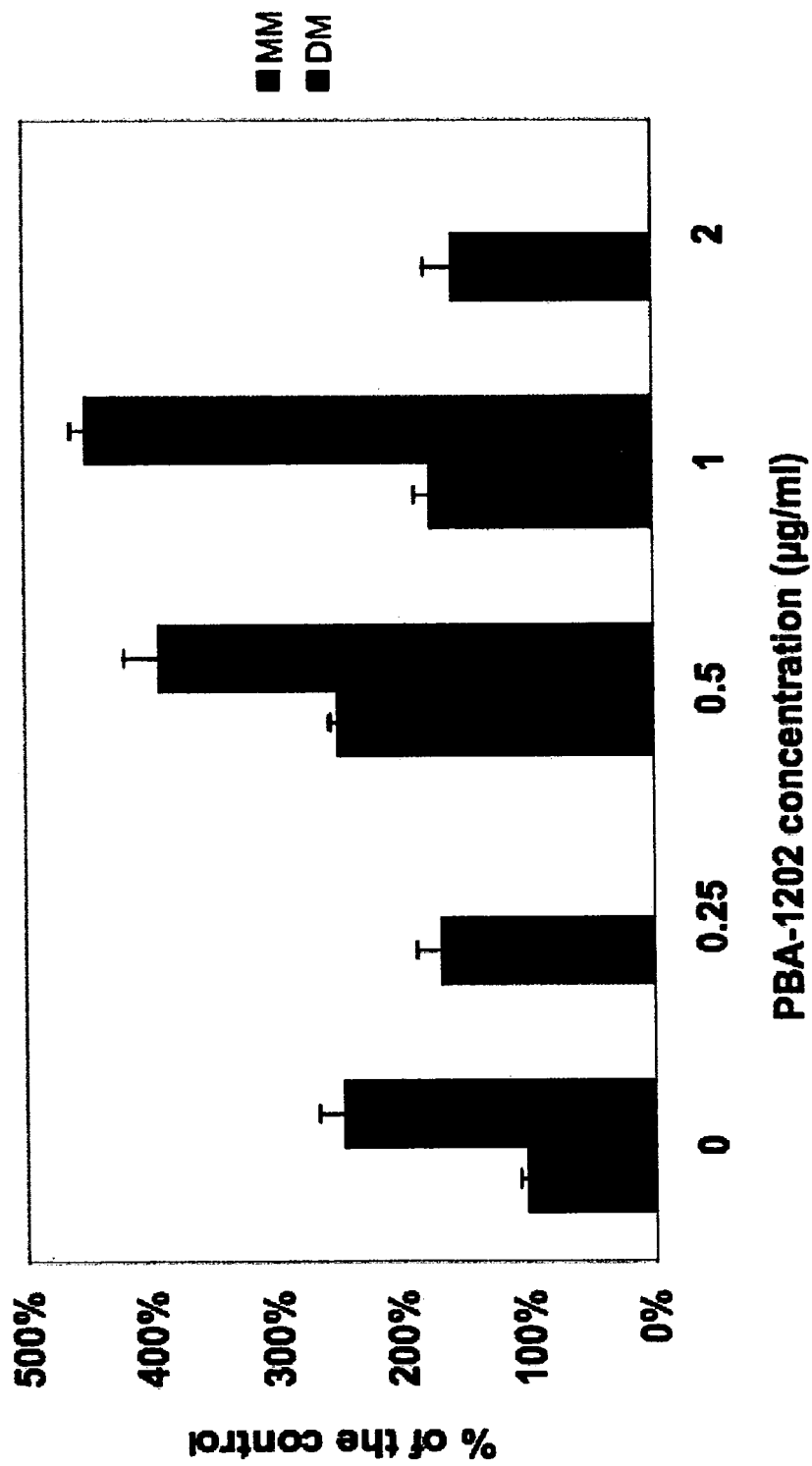
FIG. 22. A bar graph of the concentration dependent effects of rhNC4 (batch PBA-1202P) expressed by *K. lactis*, in the absence (maintenance media, MM) and presence of insulin (10 micrograms/mL) (differentiation media, DM), on the biosynthesis of Proteoglycans PGs) in pellet cultures of ATDC5 cells. Data is shown as the % change relative to controls taken to be 100%.

Effects of Sodium Pentosan Polysulfate (PPS) Alone or in Combination With rhNC4 on the Biosynthesis of Proteoglycans (Measured as $^{35}$S-GAGs) by Progenitor Cells Grown in Pellet Culture Murine Progenitor cells (cell lines C3H10T1/2 or ATDC5) purchased from RIKEN Cell Bank (Tsukuba, Japan) or human immunoselected Stro-1+ Progenitor cells (Mesoblast Ltd, Melbourne, Australia) were seeded in 2 ml screw-capped sterile centrifuge tubes and the total volume made-up to 1 ml with DMEM-High glucose medium containing 10% FBS. Progenitor cells were then centrifuged at 500 g for 10 min in a swing-out rotor at room temperature. The screw caps were loosened and the tubes placed in an incubator at 37° C., in a 5% $CO_2$/95% air moist atmosphere. The pellets generally formed within 24 hours. Medium was changed daily in the first two days, then once every 2-3 days thereafter. On day 5 the medium was removed and to each tube was added 1 ml with DMEM-High glucose medium containing 10% FBS, 5.0 μCi/ml $^{35}$S—$H_2SO_4$ and various concentrations of PPS (0, 0.1, 0.5, 1.0, 2.5, 5.0, 10.0, 20.0, μg/ml) (FIGS. 12-15) or rhNC4 (0, 0.1, 0.5, 1.0, 2.0 μg/ml) (FIG. 22). Triplicate cultures were used for all concentration of drugs. The screw caps were loosened and the tubes placed in an incubator at 37° C., in a 5% $CO_2$/95% air moist atmosphere for 3 days. On day 6, 200 μl of stock papain solution [2.5 mg/ml papain, 7.9 mg/ml L-Cystein in papain buffer (0.1 M NaAC, 5 mM EDTA, pH6.0)] was added to each tube. The tubes were tightly capped and incubated at 65° C. for 2 hours. After papain digestion, 4 replicates of 200 μl of papain digested solution were separately transferred to a 96-well micro-titre plate (200 μl/well). The remaining solution was used for the DNA fluorometric assays which were undertaken in triplicate as described above. Biosynthesis of $^{35}$S-GAGs was determined as described for the monolayer cultures and the results expressed as $^{35}$-S-GAGs/μg DNA.

FIG. 22 shows a bar graph of the concentration dependent effects of rhNC4 (batch PBA-1202P) expressed by *K. lactis*, in the absence (maintenance media, MM) and presence of insulin (10 micrograms/mL) (differentiation media, DM), on the biosynthesis of Proteoglycans PGs) in pellet cultures of ATDC5 cells. Data is shown as the % of controls taken to be 100%.

Figure 14:
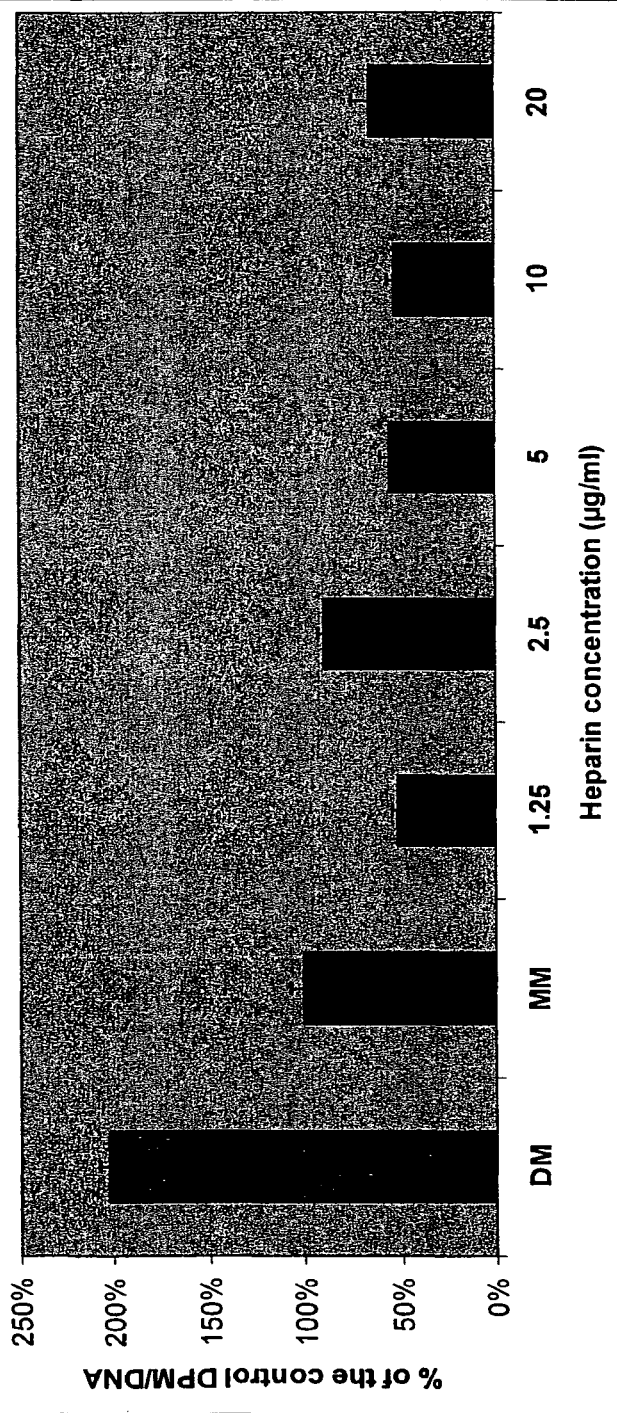
FIG. 14. A bar graph of the concentration dependent effects of Heparin on the biosynthesis of Proteoglycans (PGs as determined by the incorporation of radioactively labelled sulfate into the sulfated glycosaminoglycans ($^{35}$S-GAG) of PGs in 6 day pellet cultures of murine progenitor cells (ADTC-5). Heparin does not exhibit a chondrogenic effect over the concentration range 1.25-20 ug/mL in this cell line.

Similar experiments were undertaken using Heparin (Sigma, Sydney, Australia) in place of PPS. These results are seen in FIG. 14. The heparin regulates differentiation by suppressing chondrogenesis of the progenitor cells.

Effects of Sodium Pentosan Polysulfate (PPS) Alone or in Combination With rhNC4 on the Biosynthesis DNA (Measured as $^3$H-Thymidine Incorporation) by Progenitor Cells Grown in 6 Day Pellet Cultures Murine Progenitor cells (cell lines C3H10T1/2 or ATDC5) purchased from RIKEN Cell Bank (Tsukuba, Japan) or human immunoselected Stro-1+ Progenitor cells (Mesoblast Ltd, Melbourne, Australia) were seeded at a density of $3 \times 10^5$ cells 2 ml screw-capped centrifuge tube and topped up to 1 ml with DMEM-High (+10% FBS). Cells were centrifuged down at 500 g for 10 min in a swing-out centrifuge in room temperature then were incubated at 37° C. in a moist atmosphere of 5% CO2/95% air for 24 hours. The pellets were observed to be established over this time. Medium was changed every day in the first two days, then once every 2-3 days thereafter. On day 3, the medium was removed, to each tube was added in 640 microL of DMEM (+10% FBS), 80 microL of 50 mCi/ml 3H-Thymidine and 80 microL of rhNC4 (0, 1, 2.5, 5, 10, 25 microgramsg/ml). (FIG. 23)

All assays were undertaken in triplicated. After 3 days (66 hrs), the supernatant medium was removed and saved for the HA ELISA. 100 microL of 1 mg/ml collagenase (dissolved in DMEM medium) was added to each pellet tube. Tubes were incubated at 37° C. in a shaker at 180-200 rpm for 3.5 hrs. The collagenase digest was transferred to a 96-well plate such that the contents of each tube was divided into 4 wells. To each well was added in 200 microL dH2O and the plate stored in −20° C. for later analysis. The collagenase digests were thawed and DNA was collected with a cell harvestor and the filter discs placed in a scintillation tube. Scintillation cocktail liquid (3 mL) was added and vortexed about 1 min. The radioactivity of $^3$H-DNA in these samples was determined using a ß-scintillation counter.

Effects of Sodium Pentosan Polysulfate (PPS) Alone or in Combination With rhNC4 on the Biosynthesis of Proteoglycans (Measured as $^{35}$S-GAGs) by Progenitor Cells Grown in Micromass Cultures The technique used was based on that described by (Denker A E, Haas A R, Nicoll S B and Tuan R S. Chondrogenic differentiation of murine C3H10T1/2 multipotential progenitor cells:I. Stimulation by bone morphogenetic protein-2 in high density micromass cultures. Differentiation (1999); 64: 67-76). Briefly murine Progenitor cells (cell lines C3H10T1/2 or ATDC5) purchased from RIKEN Cell Bank (Tsukuba, Japan) or human immunoselected Stro-1+ Progenitor cells (Mesoblast Ltd, Melbourne, Australia) Ten microlitres (10 μl) of a suspension of the progenitor cells ($1 \times 10^7$cells/ml in Ham's F12 medium +10% FBS) were applied to individual wells of a 24-well plates. After incubatation at 37° C. in a humidified atmosphere of 5% CO2/95% air for 2-3 hours, 900 μl of Ham's F12 medium (10% FBS) and 100 μl of PPS solution in the same medium were added slowly into the wells to afford final concentrations of PPS in each of 0, 0.1, 0.5, 1.0, 2.5, 5.0, 10.0, 20.0 μg/ml alone or in combination with rhNC4 (0, 0.1, 0.5, 1.0, 2.5, 5.0, 10.0, 25.0 μg/ml). Each drug concentration was repeated in triplicate. The cells were maintained in culture for up to 10 days. The medium with/without drugs was changed every 3 days but 24 hours before termination of the experiment 80 μl of 50 μCi/ml $^{35}$S—$H_2SO_4$ was added to achieve a final $^{35}SO_4$ concentration of 5 μCi/ml. The following day, the cells in one of the plates were trypsinized with 150 μl/well of 2.5% trypsin and separated from the medium by centrifugation at 800 g for 10 minutes, washed with 500 μl of 1×PBS and stored in liquid nitrogen for RNA and/or DNA extraction and analysis. Media and supernatants were combined in one tube for each concentration of PPS used. To the tubes was added, 200 µl of 5× Papain solution [2.5 mg/ml Papain, 7.9 mg/ml L-Cysteine in Papain buffer (0.1 M NaAC, 5 mM EDTA, pH6.0)] and the solution incubated at 65° C. for 2 hours. After papain digestion, Four aliquots of 200 µl of digested solution were transferred to a 96-well plate (200 µl/well). The $^{35}$S-GAG released by the digestion step were separated from the free $^{35}$SO4 by adding 20 µl 5% CPC and 10 µl 1 mg/ml CSA with gentle shaking at 300 rpm RT for 20-30 min to precipitate the $^{35}$S-GAG-CPC complexes. The precipitates were collected by filtered through glass fibre filters using a cell harvester. The filters were then air-dried and discs punched to scintillation vials. 3 ml/vial scintillation cocktail liquid was added and vortexed for 30-45 sec. The radioactivity of $^{35}$S—SO$_4$ incorporated the $^{35}$S-GAG-CPC complexes was measured by scintillation counting.

Immunochemical Stain of Micromass Cultures of Progenitor Cells for Type II Collagen Micromass cultures of progenitor cells were established in 24-well culture plates at a starting density of 8×10$^4$ cells/micromass in 1 ml of DMEM (+10% FBS) with/without various concentrations of Pentosan Polysulfate as described above. On Day-5 and Day-10 of culture, media was removed and cultures were fixed with Histochoice MB (Amresco, Solon, Ohio, USA) for 20-30 min at RT. The fixed cultures were washed twice in PBS (5 min each time); p washed in PBS twice (5 min each time); b1 for 20 min at RT then washed in PBS for 5 min. The plates were then incubator. After rinsing, first with a gentle stream of PBS, followed by washing 3 times (5 min each time) with PBS, the wells were blocked with P5 minutes. To deIgG rinsing with a gentle stream of PBS then 3× washing (5 min each time) with PBS, to each micromass culture was added 200 µl of 1× (BCIP/Buffer+NBT) and the plates incubated in the reaction was stopped when the purple color first became established in the section by washing in running water. Plates and wells were then photographed with a digital camera and the images analysed by using Image J® software (http://rsb.info.nih.gov/ij/) on a personal computer.

FIG. 16 shows a bar graph showing the concentration dependent effects of PPS on proteoglycan synthesis by murine progenitor cells (C3H10T1-2) in micromass cultures for 6 days and 9 days. PPS was included in the media (Ham's F12+10% FCS) and was changed every 48 hours. $^{35}$S—SO$_4$ was added 24 hours before culture termination. Synthesis normalized to DNA content. * P<0.05, P<0.005, *P<0.0005.

Highly significant stimulation of uptake of 35S into newly synthesied PG was observed over the concentration range of 1-20 micrograms/mL in the this cell line. (FIG. 16). Moreover, after nine days in micromass cultures a 100% stimulation was obtained at 1 microgram/mL of PPS (FIG. 16).

FIG. 17 shows bar graphs showing the concentration dependent effects of PPS on proteoglycan synthesis by human Progenitor cells in micromass cultures for 5 days. Data is presented as 35S-GAG radioactivity and as a percentage of control taken as 100%. * P<0.05 relative to control. Increased proteoglycan synthesis was seen at concentration ranges between 0.5-10 µg/ml.

Human Progenitor cells also differentiated to chondrocytes in micromass cultures when incubated in the presence of PPS. However in the 5 day cultures a maximum stimulation of PG synthesis of 30% was obtained with PPS concentration of 2.5 micrograms/mL (FIG. 17).

FIG. 18 shows a bar graph showing the Pentosan Polysulfate (PPS) concentration dependent stimulation of type II collagen production by human Progenitor cells in micromass cultures for 10 days as determined by scanning and analysis of the immuno stained micromass culures shown in B. Increased Type II Collagen production was seen at concentration ranges between 0.5-10 µg/ml with the best results seen for 5 µg/ml.

These results indicate that PPS induces the progenitor cells to differentiate into chondrocytes, as evidenced by increased synthesis of both proteoglycans and Type II Collagen.

Figure 19:
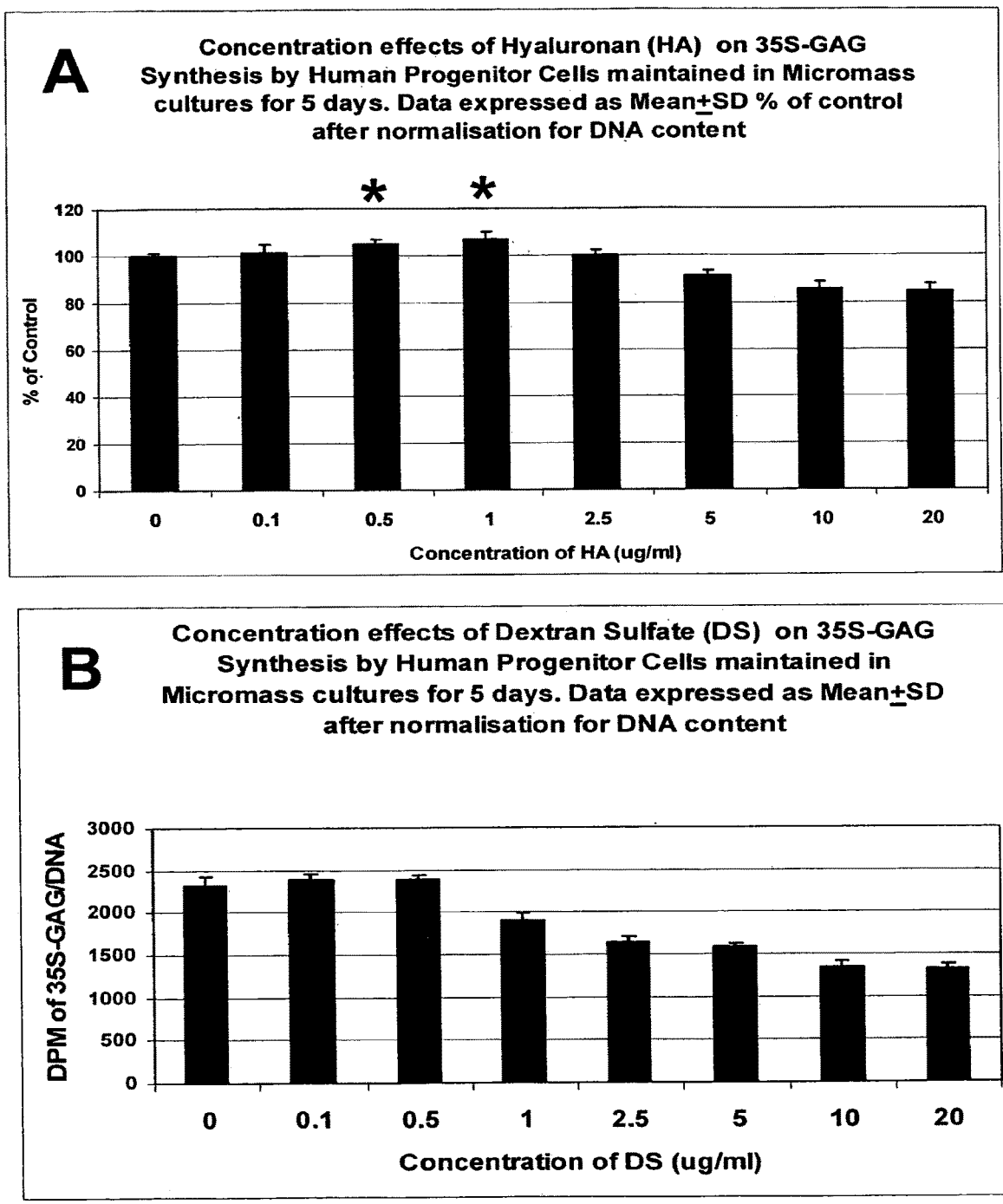
FIG. 19. Bar graphs showing the concentration dependent effects of (A) Hyaluronan (Supartz™) and (B) Dextran Polysulfate on proteoglycan synthesis by human progenitor cells in micromass cultures for 5 days. Data is presented as $^{35}$S-GAG radioactivity and as a percentage of control, taken as 100% or as DPM/ug DNA. * P<0.05 relative to control.

Similar experiments were undertaken using Hyaluronic acid (SuperArtz (SKK, Tokyo, Japan)) and Dextran polysulfate (MW=5000) (Sigma, Sydney, Australia) in place of PPS. These results are shown in FIG. 19 which shows bar graphs showing the concentration dependent effects of (A) Hyaluronan (HA) (Supartz™) and (B) Dextran Polysulfate on proteoglycan synthesis by human Progenitor cells in micromass cultures for 5 days. Data is presented as 35S-GAG radioactivity and as a percentage of control taken as 100% or as DPM/ug DNA. * P<0.05 relative to control. It can be seen that HA appeared to increase synthesis of proteoglycans but not strongly. In contrast, dextran sulfate downregulated the differentiation of progenitor cells as is evidenced by a concentration dependent reduction in the production of proteoglycans.

Concentration Effects of Sodium Pentosan Polysulfate (PPS) on the Biosynthesis DNA (Measured as $^3$H-Thymidine Incorporation) by Progenitor Cells Grown in 8 Day Micromass Cultures Ten µl of progenitor cells (7×10$^6$ cells/ml) were seeded into each well of a 24-well culture plate. After incubation at 37° C. in moist 5% CO2/95% air for 2-3 hours, 900 µl of DMEM-High medium (+10% FBS) and indicated concentrations PPS dissolved in DMEM-High medium were added slowly to the wells. The final PPS concentration were 0, 0.1, 0.5, 1.0, 2.5, 5.0, 10.0, 20.0 µg/ml, respectively. Every PPS concentration was established in triplicate. The cultures were allowed to proceed for 3 days. On day 4, to each well of the 24-well plate was added 640 µl of DMEM-High (+10% FBS), 80 µl of 10×PPS solution and 80 µl of 10 µCi/ml $^3$H-Thymidine solution to produce a final $^3$H-Thymidine concentration of 1 µCi/ml and final PPS concentrations as indicated. The cultures were then incubated in 37° C., 5% CO2 for a further 22 hours, the medium was removed and 200 µl of 1 mg/ml Collagenase solution [Collagenase buffer: 66.7 mM NaCl, 6.7 mM KCl, 4.8 mM CaCl2.2H2O, 10 mM HEPES (pH7.4)] was added to each well. The plate was incubated at 37° C. for 2.5 hours to release the cells. Every half an hour, the plate was shaken gently by hand. After collagenase digestion, the cells and digestion solution were centrifuged at 500 g for 5 min. The supernatant was removed. The cells were gently mixed with 200 µl of TE buffer and lysed by freezing-thawing twice. After lysis, 200 µl more TE buffer was added to the cells with mixing. Aliquots of the cell lysate was applied to a 96-well plate as four repeats (100 µl each well). The $^3$H-DNA in the cell lysate was collected using glass fiber filters and a cell harvester. The filters were then air-dried and punched to scintillation vials. 3 ml/vial scintillation cocktail liquid was added in and vortexed for 30-40 sec. The radioactivity of $^3$H incorporated into the DNA of proliferating cells was measured by scintillation counting.

Figure 5:
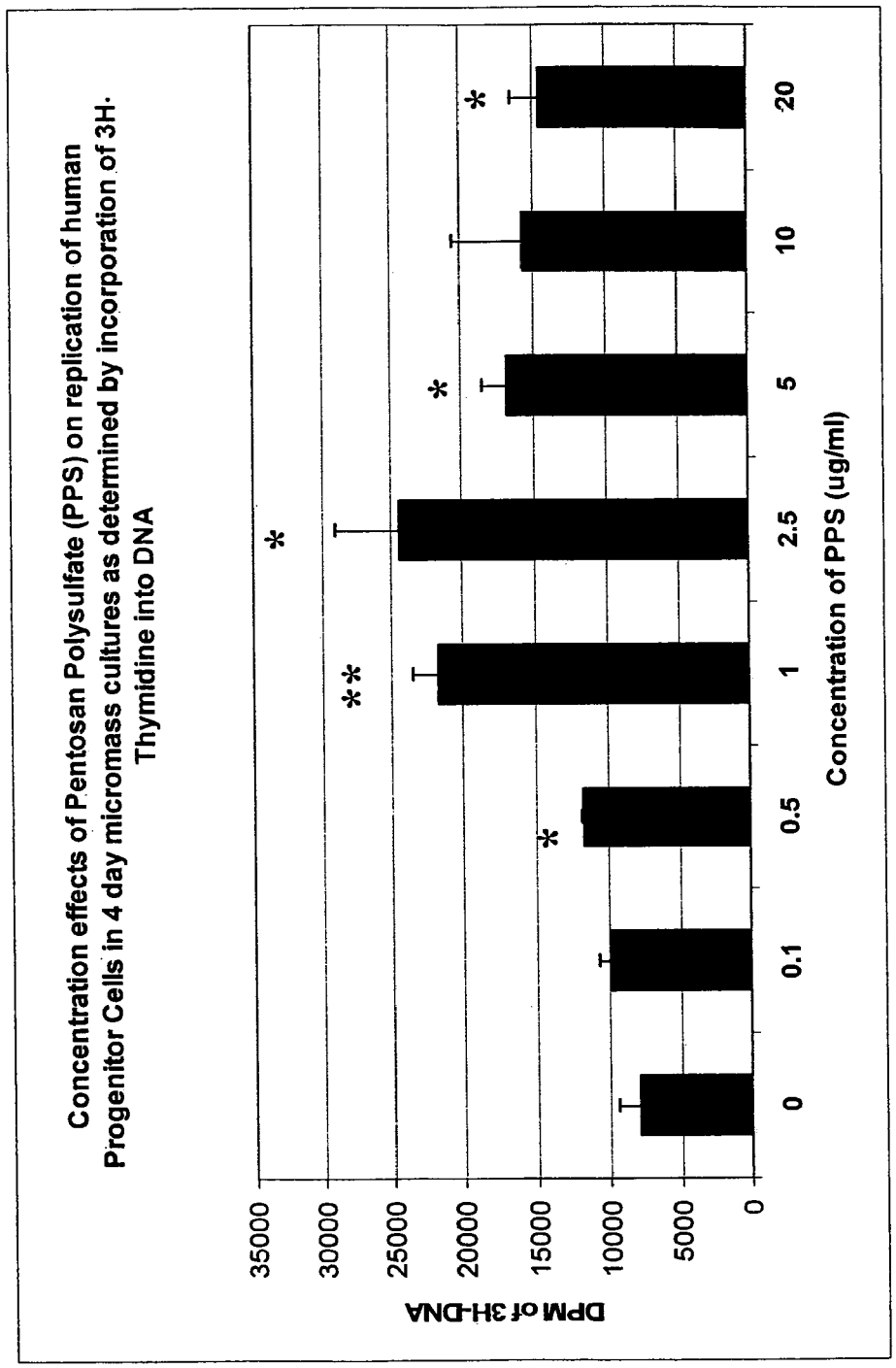
FIG. 5. A bar graph of the concentration dependent effects of Pentosan Polysulfate (PPS) on DNA synthesis by human progenitor cells, as determined by the incorporation of $^3$H-Thymidine into macromolecular DNA, after 4 day micromass cultures. *=p<0.05; **=p<0.005 relative to controls.

The results are shown in FIG. 5 which shows increased proliferation of progenitor cells in combination of PPS. It can be seen that all concentrations of PPS increased proliferation with the best results being seen at concentrations of 1 and 2.5 µg/ml.

Concentration Effects of Sodium Pentosan Polysulfate (PPS on the Biosynthesis of Hyaluronan (HA) by Progenitor Cells by Measuring the Incorporation of $^3$H-Glucosamine Into HA Human immunoselected Stro-1+ Progenitor cells (Mesoblast Ltd, Melbourne, Australia) were established in micromass cultures in 24 well plates using the method described above but seeding the progenitor cells at a density of $7 \times 10^5$ cells/well. After 24 hours in culture the media was changed and replaced with DMEM culture medium containing 10% FCS and 25 µg/ml gentamicin containing PPS (Bene-Arzneimittel, Munich, Germany) at concentrations of (0.0, 0.5, 1.0, 2.5 micrograms/mL) which had been sterilised through a 0.22 µm filter. The cultures were incubated in 5% $CO_2$/95% moist air at 37° C. for 8 days with media changes containing the indicated concentrations of PPS every 3 days. On the $8^{th}$ day $^3$H-glucosamine was added to culture medium containing the indicated concentrations of PPS to provide a solution containing 1.0 µCi/ml which was added to each well. The plates were incubated for a further 24 h. At termination of the cultures on day 9, media was collected into 5 ml capped tubes and stored at 4° C. prior to size exclusion chromatography as described below.

Isolation and Quantitation of $^3$H-Hyaluronan ($^3$H-HA) in Culture Media Using Gel Filtration Chromatography Two aliquots of 0.5 ml from each media sample were labelled A and B. 20 µl of 1 M acetic acid, pH 6.0 was added to all aliquots. 50 µl of reaction buffer (20 mM Na-acetate and 0.15 M NaCl, pH 6.0) was added to aliquot A and 50 µl of 5 TRU Streptomyces hyaluronidase (HYALASE) in reaction buffer was added to aliquot B. All samples were incubated at 60° C. for 3 h followed by boiling for 5 min to inactivate the added hyaluronidase. The samples were stored at −20° C. prior to gel filtration.

A Gel filtration column prepacked with Superdex-S200 was used to isolate and identify $^3$H-HA and $^3$H-PGs in culture media. Media samples were routinely centrifuged at high speed on a bench Microfuge for 10 min immediately before loading to the column. Samples (200 µl of each) were injected into the column through sample loop and the column was eluted with PBS buffer (0.15 M NaCl, 0.05 M $Na_2PO_4$, pH 7.2) at the flow rate of 0.2 ml/1 min. The column eluent was collected at 1.0 ml/fraction for total of 186 fractions and radioactivity was determined using a ß-scintillation counter.

Figure 27:
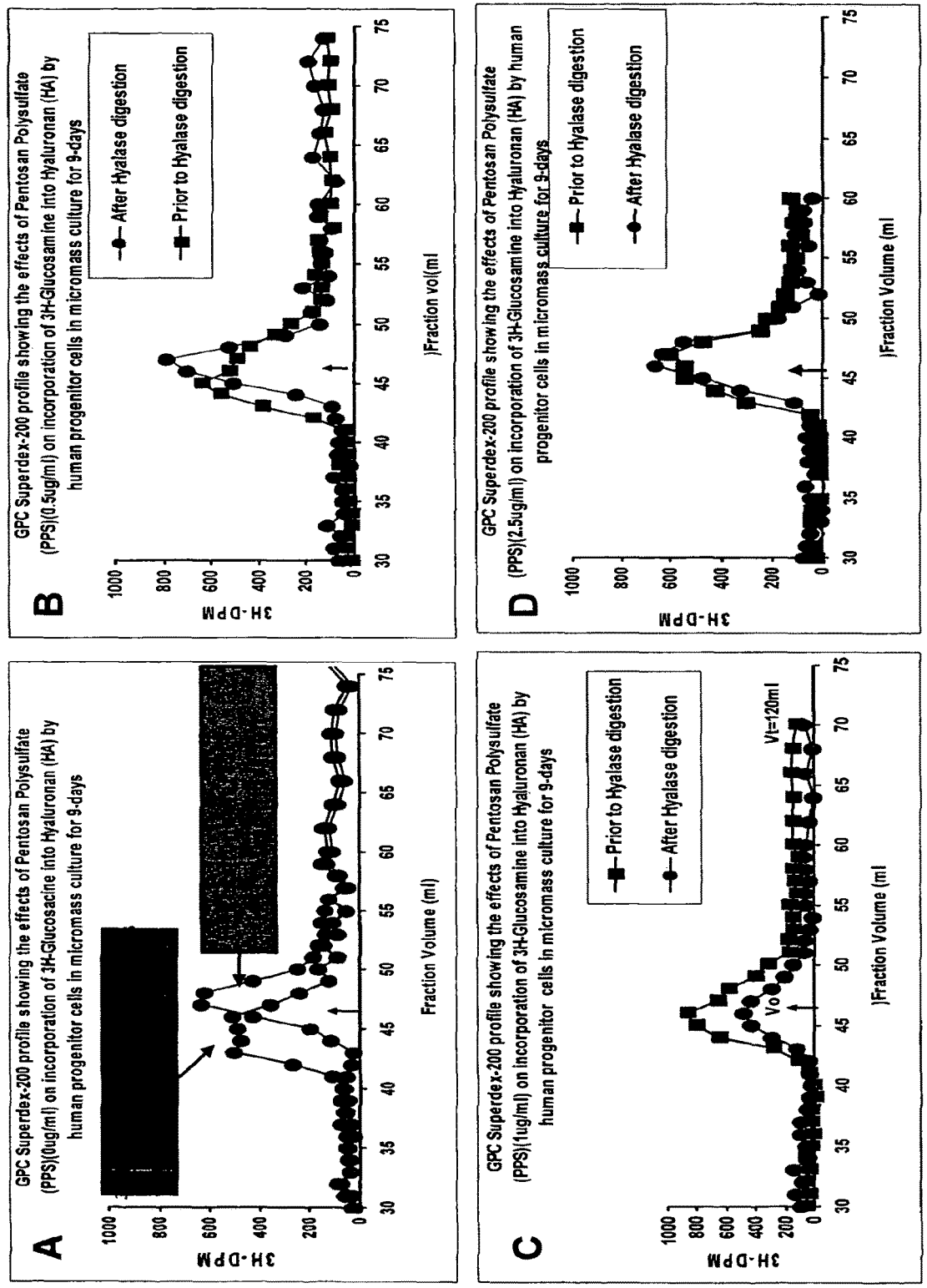
FIG. 27. Chromatographic elution profiles showing the effects of polysulfated polysaccharides on the biosynthesis of Hyaluronan (HA) and by progenitor cells by measuring the incorporation of $^3$H-glucosamine into HA. Superdex-S200 chromatographic profiles of media from human progenitor cells cultured in micromass in the presence of various concentrations of Pentosan Polysulfate (PPS) for 9 days are displayed in panels A-D. Before Hyalase digestion the profiles of radioactivity show the incorporation of $^3$H-Glucosamine into both HA and PGs by the cells but after digestion only the $^3$H-PGs remain in the void volume of the column. The % difference in areas under the profiles of the digested and pre-digested samples in the void volume fractions represents the amounts of $^3$H-HA released into the media by the PPS concentration specified.
Figure 28:
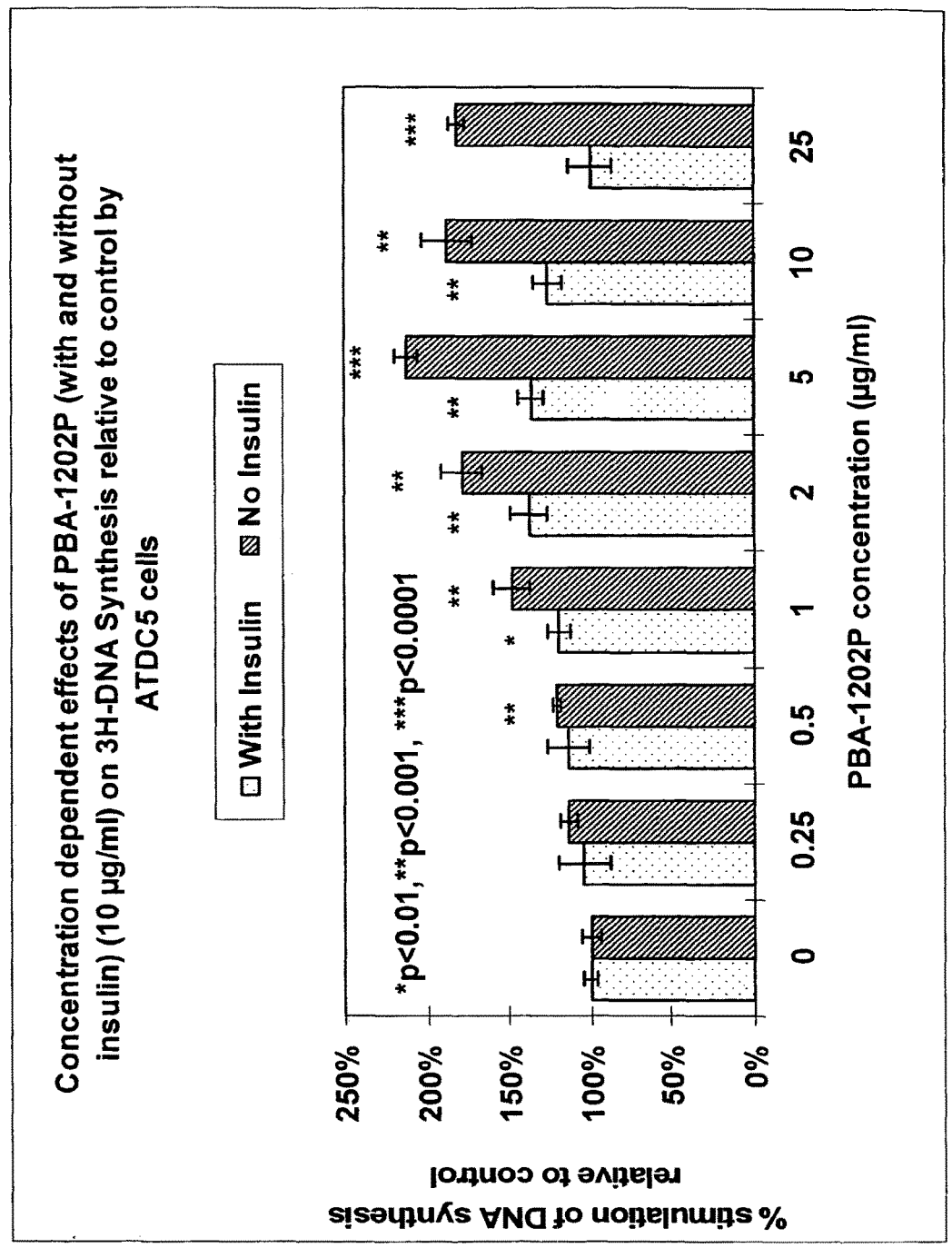
FIG. 28. A bar graph of the concentration dependent effects of rhNC4 (Batch PBA-1202P) expressed by *K. lactis* yeast cells in the absence and presence of insulin (10 micrograms/mL) on DNA synthesis as determined by the incorporation of $^3$H-Thymidine into macromolecular DNA, after 3 day culture with Murine ATDC5 progenitor cells. The data is expressed as % change relative to control cultures that contained no rhNC4. P<0.01 was statistically significant relative to control cultures.
Figure 29:
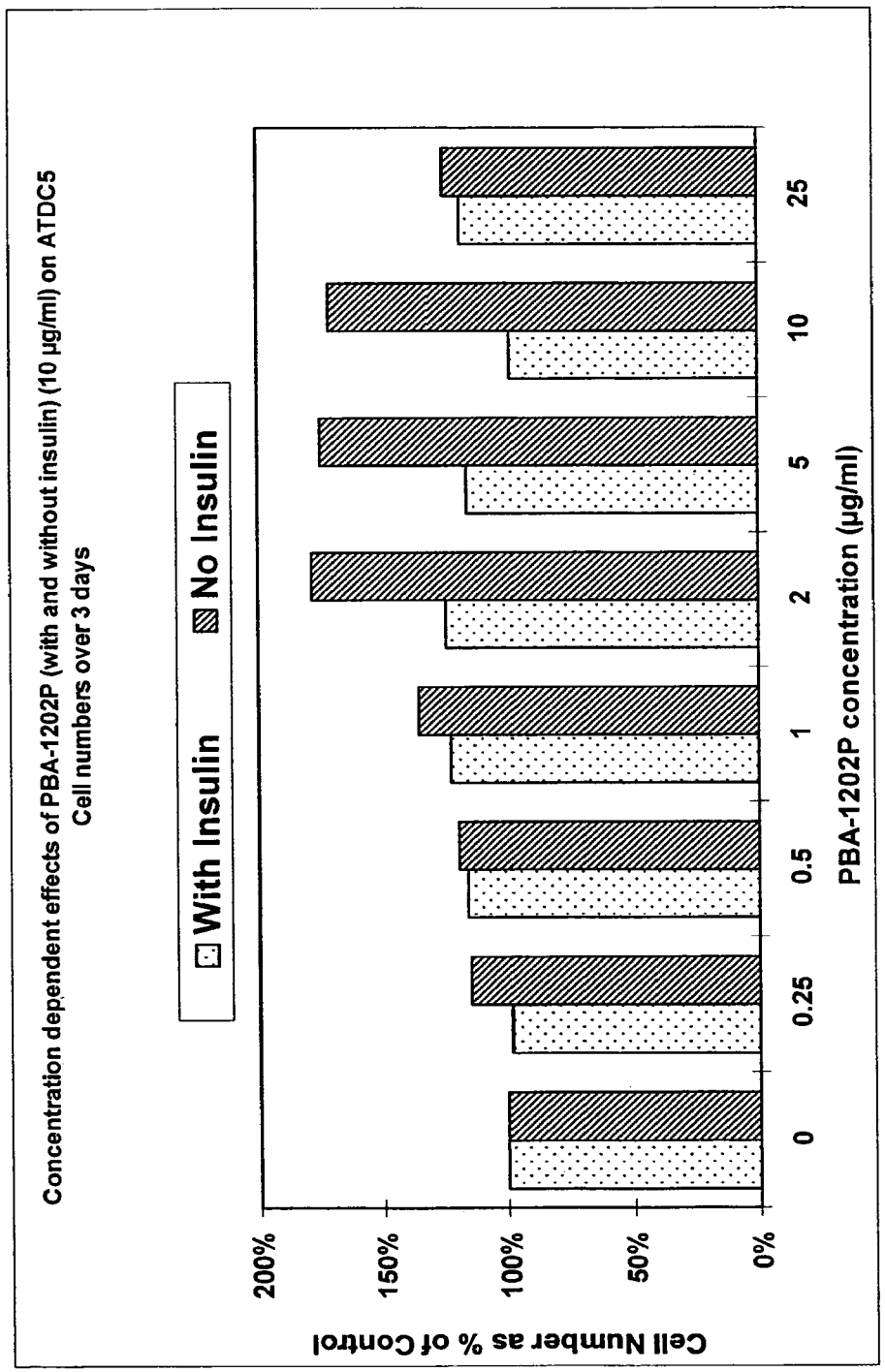
FIG. 29 A bar graph of the concentration dependent effects of rhNC4 (Batch PBA-1202P) expressed by *K. lactis* yeast cells on Murine ATDC5 progenitor cell numbers, determined using a hemocytometer, after 3 day culture in the absence and presence of insulin (10 micrograms/mL). The data is expressed as % change relative to control cultures that contained no rhNC4. P<0.01 was statistically significant relative to control cultures.
Figure 30:
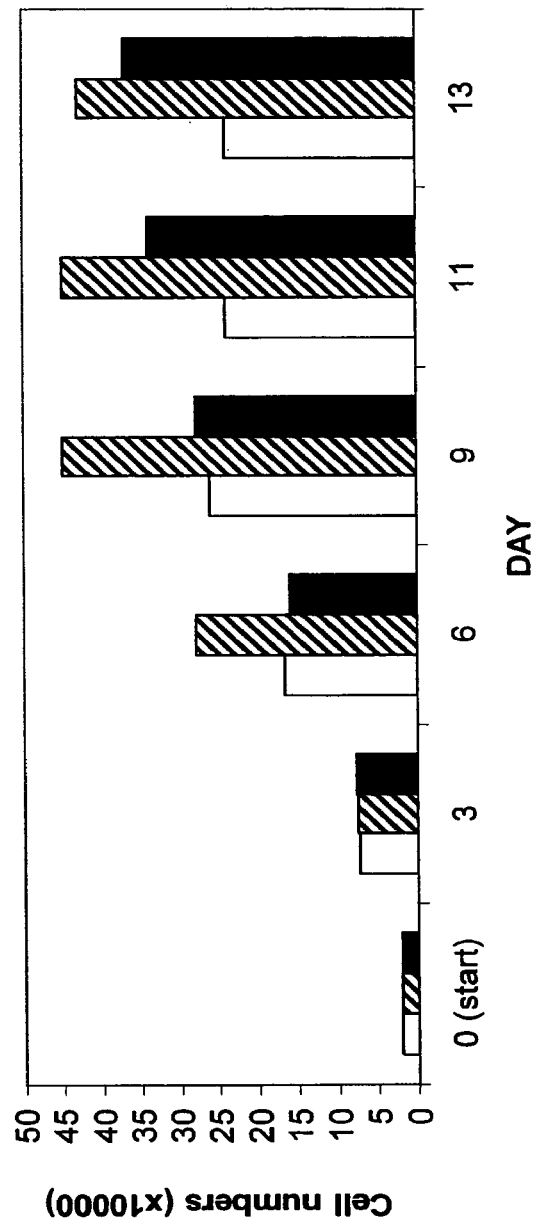
FIG. 30. A bar graph of the kinetics of ATDC5 cell growth induced by rhNC4 (batch PBA-1200P) (5 ug/ml) or Insulin (10 ug/ml) relative to control over 13 days. 20,000 cells per well were seeded at Day 0 (Start) with medium changes every 48 hrs. Insulin treated cultures reached confluence on day 6 and PBA-1200P on day 9. Control cultures also reached confluence on day 9 but in contrast to cultures containing insulin or PBA-1200P ceased to undergo replication.
Figure 31:
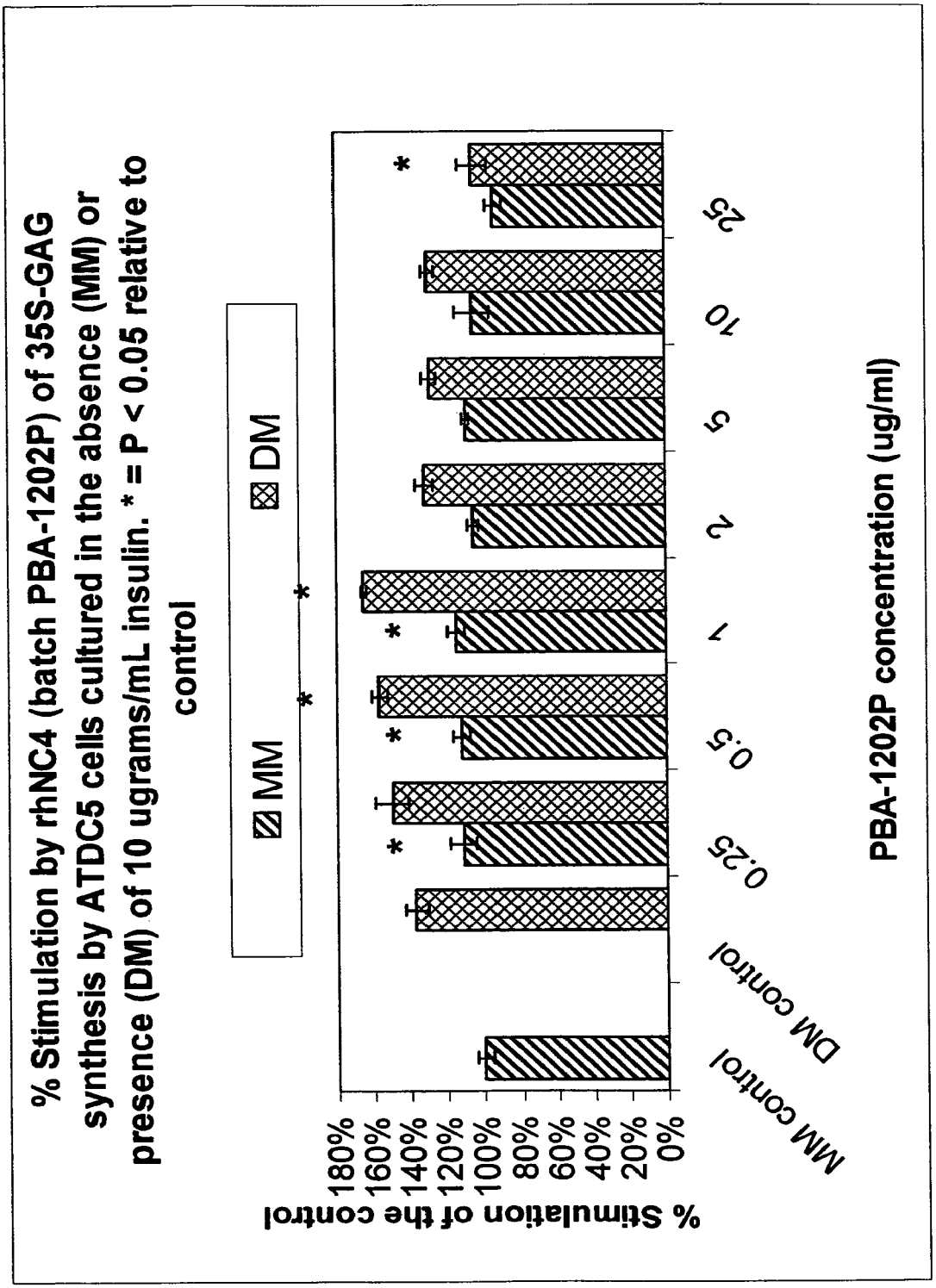
FIG. 31. A bar graph of the concentration dependent effects of rhNC4 (batch PBA-1202P) expressed by *K. lactis*, in the absence (maintenance media, MM) and presence of insulin (10 micrograms/mL) (differentiation media, DM), on the biosynthesis of Proteoglycans (PGs) as determined by the incorporation of radioactively labelled sulfate into the sulfated glycosaminoglycans ($^{35}$S-GAG) of PGs after 3 day culture with Murine ATDC5 progenitor cells. The data was expressed as % change relative to control cultures that contained no rhNC4. P<0.05 was statistically significant relative to control cultures.
Figure 32:
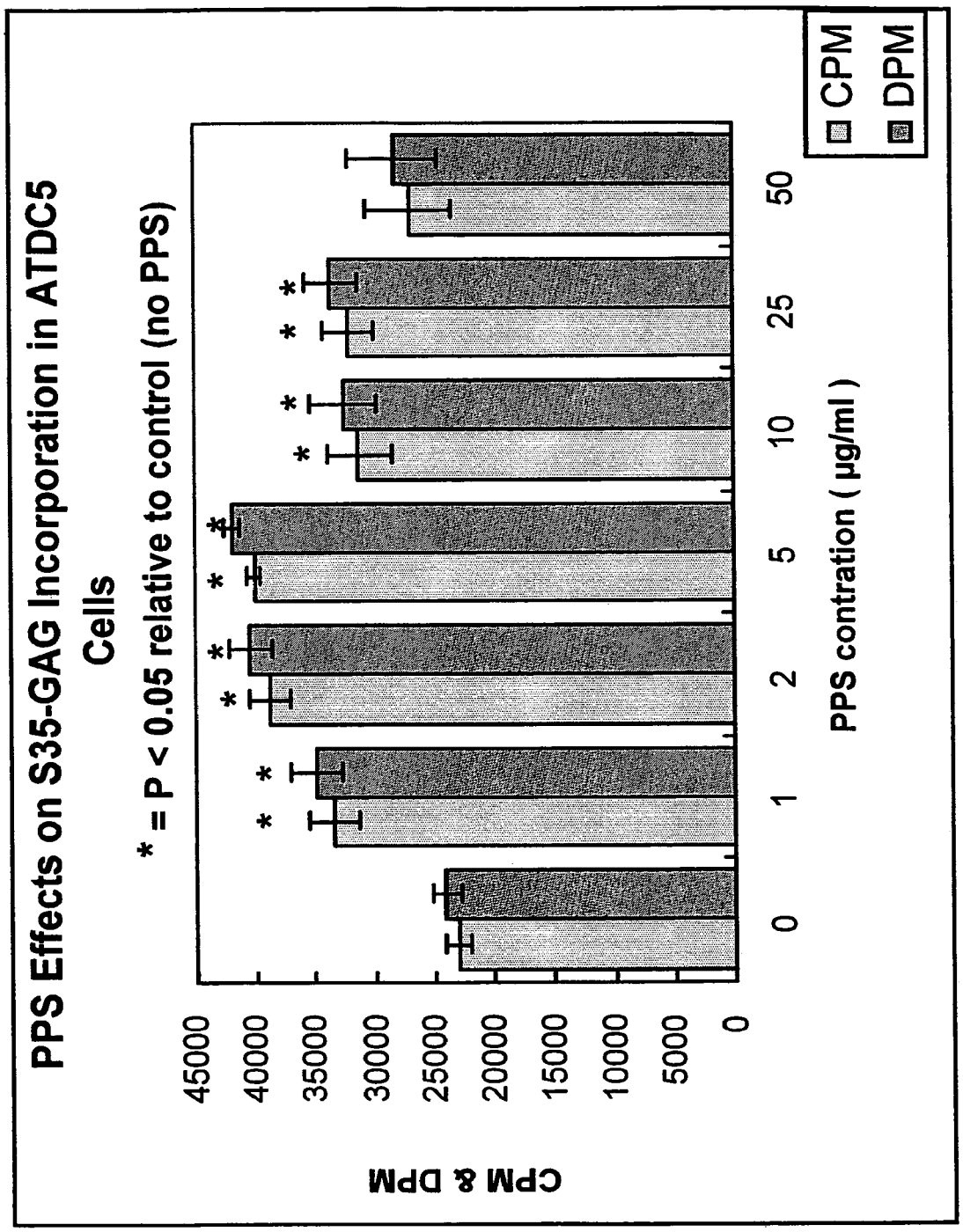
FIG. 32. A bar graph of the concentration dependent effects of Pentosan Polysulfate (PPS), in the presence of insulin (10 micrograms/mL), on the biosynthesis of Proteoglycans PGs) as determined by the incorporation of radioactively labelled sulfate into the sulfated glycosaminoglycans ($^{35}$S-GAG) of PGs after 3 day culture with Murine ATDC5 progenitor cells. The data was expressed as $^{35}$S-GAG radioactivity as counts per minute (CPM) and decays per minute (DPM) relative to control cultures that contained no PPS. P<0.05 was statistically significant relative to control cultures.

These results are shown in FIG. 27. Analysis of the area under the chromatographic profiles before and after digestion with the Streptomyces hyaluronidase (HYALASE) for control cultures containing no PPS showed that 14.3% of the $^3$H-glucosamine was incorporated into HA and 85.7% into the PG subunits. As is evident from the profiles shown in 27A the molecular size of the PG-HA aggrecan complex was larger than the PG monomers which become liberated when the HA is digested away.

Of the concentrations of PPS examined only 0.1 micrograms/mL and 1.0 micrograms/mL showed substantial increases in levels of newly synthesised $^3$H-HA. in the culture media. The proportion of radioactivity present in the post digestion void volume fractions of PG monomers being 50.4% showing that 49.6% was incorporated into HA for 1 microgram/mL FIG. 27C) and 35.5% for 0.1 micrograms/mL (profile not shown). With the lower concentration of PPS (FIG. 27B) 15.1% of radioactivity was found in the HA fractions, while the higher concentration of 2.5 micrograms/mL only incorporated about 11% of $^3$H-glucosamine into HA. Although these data suggest that maximum synthesis of HA by progenitor cells in micromass cultures occurred at the PPS concentration of 1.0 micrograms/mL, the $^3$H-HA levels remaining in the micromass extracellular matrix have yet to be determined. Since parallel studies described herein have shown that PPS stimulates chondrogenic differentiation of progenitor cells and the formation of cartilage proteoglycans, the extracellular matrix surrounding the cells may represent a richer source of the newly synthesised HA in the form of a component of the PG aggrecan complex. Nevertheless, this is the first report which demonstrates that PPS stimulates the biosynthesis of HA by cultured progenitor cells.

Concentration Effects of rhNC4 (Batch PBA-1202p) Alone and in Combination With Sodium Pentosan Polysulfate (PPS on the Biosynthesis of Hyaluronan (HA) by Progenitor Cells by Measuring the Incorporation of $^3$H-Glucosamine Into HA Murine Progenitor cells (cell lines C3H10T1/2 or ATDC5) purchased from RIKEN Cell Bank (Tsukuba, Japan) or human immunoselected Stro-1+ Progenitor cells (Mesoblast Ltd, Melbourne, Australia) will be established in micromass cultures as described above or seeded at $1.5 \times 10^5$ cells/well in 6-well culture plates and allowed to attach for 24 h before addition of compounds. Various concentrations of rhNC4 preparations alone and in combination with PPS (Bene-Arzneimittel, Munich, Germany) will be prepared in DMEM culture medium containing 10% FCS and 50 µg/ml gentamicin at double the concentration required in the cultures, sterilised through a 0.22 µm filter and then serially diluted to give final concentrations of the drugs required for each experiment. Aliquots of each of the test solutions will be added to each well of 24-well culture plates. Stock $^3$H-glucosamine will be diluted in culture medium to give a 1.0 µCi/ml solution which will be immediately added to each well. The plates will be incubated for a further 24 h. At culture termination, media will be collected into 5 ml capped tubes and stored at −20° C. for $^3$H-HA analysis. Cells will be released by trypsinization and centrifuged with washing. Trypsin mobilized radioactively labelled-HA and washing will be analysed as for the media and the cells were then used for extraction of RNA and evaluation of gene expression as described below.

Isolation and Quantitation of $^3$H-Hyaluronan ($^3$H-HA) in Cultures Using Gel Filtration Chromatography Two aliquots of 0.5 ml from each media sample will be labelled A and B. 20 µl of 1 M acetic acid, pH 6.0 will be added to all aliquots. 50 µl of reaction buffer (20 mM Na-acetate and 0.15 M NaCl, pH 6.0) will be added to aliquot A and 50 µl of 5 TRU Streptomyces hyaluronidase in reaction buffer will be added to aliquote B. All samples will be incubated at 60° C. for 3 h followed by boiling for 5 min to inactivate the added hyaluronidase. The samples will be store at −20° C. prior to gel filtration.

Gel filtration columns prepacked with either Superose 6 or Superdex-S200 will be used to isolate and identify $^3$H-HA in culture media. Media samples will be routinely centrifuged at high speed on a bench Microfuge for 10 min immediately before loading to the column. Samples (200 µl of each) will be injected into the column through sample loop and the column will be eluted with PBS buffer (0.15 M NaCl, 0.05 M $Na_2PO_4$, pH 7.2) at the flow rate of 0.2 ml/1 min. The column eluent will be collected at 0.5 ml/fraction for total of 46 fractions and radioactivity will be determined using a ß-scintillation counter.

This experiment will show a concentration dependent stimulation of HA synthesis with optimum effects over the range of 1-5 micrograms/mL of PPS alone and rhNC4 of 5-25 micrograms/mL. In combination 2 micrograms/mL with 5-25 micrograms/mL of rhNC4 will show synergy.

Concentration Effects of rhNC4 (Batch PBA-1202p) Alone and in Combination With Sodium Pentosan Polysulfate (PPS on the Biosynthesis of Hyaluronan (HA) by Progenitor Cells Using a ELISA Murine Progenitor cells (cell lines C3H10T1/2 or ATDC5) purchased from RIKEN Cell Bank (Tsukuba, Japan) or human immunoselected Stro-1+ Progenitor cells (Mesoblast Ltd, Melbourne, Australia) will be seeded at $2 \times 10^5$ cells/well in 24 well culture plates and maintained in 1 ml DMEM/Ham's F-12 medium (Invitrogen) supplemented with 10% FBS (Sigma) and incubated at 37° C. in a 5% CO2/95% moist air atmosphere until the cells reached 80% confluence. The media will then be replaced with DMEM/Ham's F-12 containing various concentrations of the rhNC4 preparations alone and in combination with pentosan polysulfate (Bene-Arzneimittel, Munich, Germany) and the cultures will be maintained at 37° C., in 5% $CO_2$ for a further 24 hours. The media in each well will be separated from the cells and transferred to a 2.0 ml microfuge tube. The monolayer cells remaining in the wells will be detached by trypsinization and then separated from the supernatant by centrifugation at 350 g for 5 min. The supernatant will be collected and combined with the medium. The combined medium and supernatant mixture (200 µl) will be assayed for hyaluronan content using the HA-ELISA as described above. The supernanant from the cell trypsinization will be boiled to denature and inactivate the enzyme and also assayed for HA content using the ELISA. The HA of these fractions will be considered to represent the HA content of the extracellular matrix (ECM).

The results of this experiment will confirm the results found in FIG. 27. The ELISA will demonstrate HA production by progenitor cells in the presence of low doses (including 1-5 microgram/ml) of polysulfated polysaccharides.

Effects of Sodium Pentosan Polysulfate (PPS) on the Differentiation of Human Progenitor Cells in an Osteogenic Media Using In Vitro Mineralisation Assays.

The conditions necessary for the induction of human progenitor cells to develop mineralised bone matrix in vitro have been previously described (Gronthos S, A C Zannettino, S J Hay, S Shi, S E Graves, A Kortesidis and P J Simmons. (2003). Molecular and cellular characterisation of highly purified stromal stem cells derived from human bone marrow. J Cell Sci 116:1827-1835). The osteoinductive media consists of alpha-MEM media supplemented with 2% (v/v) FCS, 1.8 mM KH2PO4, 10-7 dexamethasone sodium phosphate, 50 IU/ml penicillin, 50 µg/mL streptomycin, 1 mM Sodium Pyruvate, 100 µM L-Ascorbic acid 2-phosphate, 2 mM L-glutamine and 10 mM HEPES buffer.

Human progenitor cells were seeded into 96-well plates at $8 \times 10^3$ cells per well and allowed to reach ≥90% confluence prior to the addition of osteoinductive media containing nominated concentrations of PPS (0.0, 1.0, 5.0, 10 micrograms/mL). Cells were cultured at 37° C. in the presence of 5% CO2 for the indicated period. The osteoinductive culture media containing fresh compound was changed twice weekly for a period of 4 weeks.

The results from this experiments can be seen in FIG. 7A. It shows that the presence of PPS suppressed differentiation into osteocytes, particularly at 1 and 10 micrograms PPS/mL Effects of Sodium Pentosan Polysulfate (PPS) on the Differentiation of Human Progenitor Cells in an Osteogenic Media—Analysis of In Vitro Mineral Content Total mineral content per well in the above cultures was assessed by measuring the calcium levels per total DNA in each well. Cell cultures were washed three times with Ca+ and Mg+ free PBS and left to solublize overnight in 0.6M hydrochloric acid (100 µL per well). The acid-solublized mineral 23 was transferred to a new 96-well plate and reacted with o-cresol-phthalein-complexone (Thermal Electron Corporation, USA) to form a purple dye that was measured at 570 nm using an EL 808 Ultra Microplate Reader. The intensity of the purple dye is directly proportional to the calcium concentration in each well. Absolute calcium concentration was extrapolated from a calcium standard curve according to the manufacturer's recommendations. Following this, the acid-solublized cultures were rinsed three times with Ca2+ and Mg2+ free PBS and incubated in a 100 µLs of solution of 100 µg/mL Proteinase K at 37° C. for 2 hours. Digested samples were vigorously pipetted and 50 µL of each well was transferred to a well of a nonfluorescent assay plate, containing 150 µL diluted Hoechst 33258 (2 µg/mL) in DNA assay buffer (2M NaCl and 50 mM Sodium Phosphate). Absolute absorbance was determined by measuring against a series of DNA standards at 350 nm by LS55 Luminescence Spectrometer (Perkin Elmer).

The results from this experiments can be seen in FIG. 7B. The fact that PPS cultures all appear the same as the media indicated that no calcified deposites are present. Normally mineralized deposits stained positively with the Alizarin Red reagent and are formed within 4 weeks of culture of progenitor cells under osteoinductive conditions.

Effects of Sodium Pentosan Polysulfate (PPS) on the Differentiation of Human Progenitor Cells in an Adipogenic Media Using In Vitro Adipogenic Assays The conditions required for the development of lipids from human bone marrow stromal cells in vitro have been previously described (Gimble J. Marrow stromal adipocytes. In: *Marrow stromal cell culture*. J N Beresford, Owen, M. E., ed. Cambridge University Press, Cambridge, pp 67-87 (1998)). Briefly, human progenitor cells were seeded into 96-well plates at a density of $8 \times 10^3$ cells per well in complete alpha-MEM growth media and were allowed to reach >90% confluence prior to addition of inductive media. Cells were cultured in adipogenic-inductive media comprised of complete alpha-MEM supplemented with 0.5 mM 3-Isobutyl-1-methyl-xanthine (IBMX), 60 microM Indomethacin, and 0.5 microM Hydrocortisone in the presence of a titration of PPS (0.0, 1.0, 5.0, 10 micrograms/mL). The inductive media was changed twice weekly for a period of 4 weeks. Cells were stained for the presence of lipid using Oil Red 'O'.

Oil Red 'O' Staining of Lipid

Cells were cultured as described above and gently rinsed in 1×PBS (pH7.4) to avoid disruption of the cell monolayer. Cells were fixed in phosphate buffered formalin for 15 minutes at RT. The fixative was subsequently removed and lipid stained by adding 100 microL of freshly filtered Oil Red O (3 mg/mL; MP Biomedicals, Australia) for ≥2 hours at RT. Cells were rinsed 3 times with RO water and counter stained with Mayer's Haematoxylin (Lillie's modification). Haematoxylin stains were aspirated and replaced by water and the Oil Red O positive adipocytes examined under a light microscope and photographed with the DP20-56 Olympus camera (Olympus, Japan).

These results are shown in FIGS. 8A and B. It can be seen that PPS regulated the differentiation of progenitor cells into adipocytes with upregulation seen at all concentrations.

Effects of Sodium Pentosan Polysulfate (PPS) on the Biosynthesis of Proteoglycans (Measured as $^{35}$S-GAGS) by Progenitor Cells Grown in Collagen Sponges.

Human immunoselected Stro-1+ Progenitor cells (Mesoblast Ltd, Melbourne, Australia) prepared as a suspension containing an average of 100,000 cells in 100 microL of 1:1 high glucose DMEM/Ham's F-12 medium (Invitrogen) supplemented with 10% FBS (Sigma) will be injected using a micropipett into the centre of blocks of prepared collagen sponges placed in the wells of a 24 well culture plate. The collagen sponges will be Sterile Gelfoams (Pharmacia & Upjohn Co., Kalamazoo, Mich.) pre-cut before hand to 0.5 $cm^3$ cubes. To each well will be added 2 mL media+FBS and the plates will be incubated at 37° C., in 5% $CO_2$/95% air for 48 hours. The media will then be replaced with 1:1 high glucose DMEM/Ham's F-12 medium (Invitrogen) supplemented with 10% FBS (Sigma) containing various concentrations of PPS (0, 0.1, 0.5, 1.0, 2.5, 5.0, 10.0, 25.0 µg/ml) for a further 48 hours. All PPS concentrations will be cultured in triplicate. The medium will then be changed to defined medium, which contained the indicated concentrations of PPS and 5 µCi/ml of $^{35}S$—$H_2SO_4$ (Perkin Elmer, USA). The experiments will be terminated after 48 hours incubation when PG biosynthesis will be determined by measuring the incorporation of $^{35}SO_4$ into the PG as ($^{35}S$-GAGs) released into the media and after collagenase digestion of the sponges as described above.

This experiment will demonstrate cartiliage formation within the sponge is enhanced in the presence of polysulfated polysaccharides at similar concentrations to those shown in vitro and described herein. The experiment will confirm that doses of 0.5-1.0 million precursor cells are suitable cell numbers and that concentrations of 1-10 micrograms/ml polysulfated polysaccharides provide a beneficial effect.

Evaluation of De Novo Cartilage Formulation in an Animal Model of Disc Regeneration and Cartilage Repair Using a Formulation of Progenitor Cells and Pentosan Polysulfate (PPS).

Animal Protocol

Two level spinal surgeries will be undertaken at the cervical C3/4 and C4/5 spinal levels of 12 adult Merino/Leicester ewes which will be randomly divided into 2 groups of 6. The procedure will require that the intervertebral discs be surgically removed from these levels and a biodegradable implant filled by a collagen sponge scaffold containing the progenitor cells be implanted between the vertebral bodies previously occupied by the discs. Apart from the different cells injected into the sponges the only other variable in the design of the study will be whether the cartilage end plates (CEP) is mechanically perforated prior to insertion of the implant The duration of the study will be 12 weeks from the time of implantation to sacrifice.

Group A (N=6)

Sterile Gelfoam Gelatin Sponges (Pharmacia & Upjohn Co., Kalamazoo, Mich., USA) will be cut to size using a preformed template, then injected with 100 micro litres of Profreeze® solution using a micro-pipette. The loaded sponge will then be inserted into the specially modified biodegradable cage which will be fixed within the surgically excised cervical disc spaces at the levels indicated. The cages will be secured in place by a means of a commercial vertebral plate.

Group B (N=6)

Sterile Gelfoam Gelatin Collagen Sponges will cut to size using a preformed template and loaded with 100 micro litres of Profreeze® solution containing progenitor cells (1 million ovine progenitor cells) +10 micrograms of PPS. The loaded sponge will then be inserted into a biodegradable cage which will be fixed within the surgically excised cervical disc spaces at the levels indicated. The cages will be secured in place by a means of a commercial vertebral plate.

Evaluation of Experimental Outcomes

Lateral radiographs will be taken of all cervical spines under induction anaesthesia at the following time points: Baseline, Operation, 1, 2 and 3 months following implantation of the test articles and scored for bone formation using the scoring system shown in Table 3.

TABLE 3

| Score | Description |
|---|---|
| 0 | no bony fusion |
| 1 | maximum intervertebral gap in the cranio-caudal direction of more than 5 mm |
| 2 | maximum intervertebral gap in the cranio-caudal direction of less than 5 mm |
| 3 | complete bony fusion. The maximum intervertebral gap in the cranio-caudal direction will be measured directly on lateral radiographs using a ruler |

Animals will also be monitored throughout the study according to animal ethics guidelines for care of chronically prepared sheep using the schedule shown in Table 4.

TABLE 4

Observation of animals following surgery

| Observation | Frequency/Day | Duration |
|---|---|---|
| Weight | x1 | Study entry |
| Behaviour, Posture and Activity | x1 | Study duration |
| Pain and Discomfort | x1 | Study duration |
| Observation of procedural area for local irritation/infection | x1 | Minimum of 3 days post surgery |
| Decreased activity/inability to move | x1 | Study duration |
| Assessment of daily food/water consumption | x1 | Study duration |

Histological Analysis

Following sacrifice intact cervical spines will be dissected from the animals and the C3/4 and C4/5 motion segments cut from the remainder of the spine using a band saw. These two segments will then be cut in the sagital plane into 2 sections and stored in 10% normal buffered formalin. These sections will contain the cage with 3 mm of the superior and inferior vertebral bodies on either side. They will then be decalcified using formic acid and then dehydrated in ascending concentrations of ethanol under agitation. Following clearing in xylene, tissues will be embedded in paraffin, cut and stained with H&E, Alcian Blue, Toludine Blue, Massons Trichrome. The Toluidine Blue stained sections will be used for the histomorphometric analysis using quantitative image analysis to determine optical density of proteoglycan distribution and matrix dimensions using Image J® software (http://rsb.info.nih.gov/ij/) on a personal computer.

Unstained paraffin sections will also be used for immunohistochemical analysis of matrix components. They will be pre-digested with combinations of chondroitinase ABC (0.25 U/ml) in 20 mM Tris-acetate buffer pH 8.0 for 1 h at 37° C., bovine testicular hyaluronidase 1000 U/ml for 1 h at 37° C. in phosphate buffer pH 5.0, followed by three washes in 20 mM Tris-HCl pH 7.2 0.5M NaCl (TBS) or proteinase-K (DAKO 53020) for 6 min at room temperature to expose antigenic epitopes. The tissues will then be blocked for 1 h in 20% normal swine serum and probed with a number of primary antibodies to large and small proteoglycans and collagens (Table 5). Negative control sections will also be processed either omitting primary antibody or substituting an irrelevant isotype matched primary antibody for the authentic primary antibody of interest. Commercial (DAKO) isotype matched mouse IgG (DAKO Code X931) or IgM (DAKO Code X942) control antibodies (as appropriate) will be used for this step. The DAKO products X931 and X942 will be mouse monoclonal IgGi (clone DAK-G01) and monoclonal IgM (clone DAK-G08) antibodies directed against *Aspergillus niger* glucose oxidase, an enzyme that is neither present nor inducible in mammalian tissues. Horseradish peroxidase or alkaline phosphatase conjugated secondary antibodies will be used for the detection using 0.05% 3, 3'-diaminobenzidene dihydrochloride and 0.03% $H_2O_2$ in TBS, Nova RED, nitroblue tetrazolium/5-bromo-4-chloro-3-indolylphosphate/iodonitrotetrazolium violet (NBT/BCIP/INT) or New Fuchsin as substrates. The stained slides will be examined by bright field microscopy and photographed using a Leica MPS 60 photomicroscope digital camera system.

TABLE 5

Primary antibodies to proteoglycan and collagen core protein epitopes

| Primary antibody epitope | Clone (isotype) | References |
|---|---|---|
| Large Proteoglycans | | |
| Aggrecan | AD 11-2A9 (IgG) | a |
| Versican | 12C5 (IgG) | b |
| Collagen | | |
| Type I | I8H5 ($IgG_1$) | b, c |
| Type II | II-4CII ($IgG_1$) | b, c |
| Type IV | CIV-22 ($IgG_1$) | b, c |
| Type VI | Rabbit polyclonal | b, c |
| Type IX | Mouse monoclonals D1-9 ($IgG_1$), B3-1 ($IgG_{2b}$) | d |

(a) Melrose, J., Little, C. B. & Ghosh, P. Detection of aggregatable proteoglycan populations by affinity blotting using biotinylated hyaluronan. *Anal Biochem* 256, 149-157 (1998). Melrose, J., Smith, S. & Ghosh, P. Differential expression of proteoglycan epitopes by ovine intervertebral disc cells. *J Anat* 197 (Pt 2), 189-198 (2000).
(b) Melrose, J., Smith, S., Ghosh, P. & Taylor, T. K. Differential expression of proteoglycan epitopes and growth characteristics of intervertebral disc cells grown in alginate bead culture. *Cells Tissues Organs* 168, 137-146 (2001).
(c). Shen, B., Melrose, J., Ghosh, P. & Taylor, F. Induction of matrix metalloproteinase-2 and -3 activity in ovine nucleus pulposus cells grown in three-dimensional agarose gel culture by interleukin-1beta: a potential pathway of disc degeneration. *Eur Spine J* 12, 66-75 (2003).
(d) Ye, X. J., Terato, K., Nakatani, H., Cremer, M. A. & Yoo, T. J. Monoclonal antibodies against bovine type IX collagen (LMW fragment): production, characterization, and use for immunohistochemical localization studies. *J Histochem Cytochem* 39, 265-271 (1991).

Statistics

The Student t test will be used for pair wise comparisons as indicated. Statistical significance will be given at P less than 0.05. One-way analysis of variance (ANOVA) will be used for multiple comparisons as indicated. Statistical significance between the groups will be determined using the Fisher projected least significance difference test at P less than 0.05.

This experiment will demonstrate that relative to control, the use of polysulfated polysaccharides and progenitor cells will result in greater (more abundant) production of cartilage in the disk space.

In addition, in the excised disc spaces with punctured cartilaginous end plates which had an interface with the collagen sponges containing progenitor cells plus PPS, enhanced infiltration of endogenous blood bourne progenitor cells will be observed accompanied by more complete healing of the mechanically produced cartilage defects.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

SEQUENCE LISTING

```
<160> NUMBER OF SEQ ID NOS: 103

<210> SEQ ID NO 1
<211> LENGTH: 245
<212> TYPE: PRT
<213> ORGANISM: Homo sapiens

<400> SEQUENCE: 1

Ala Val Lys Arg Arg Pro Arg Phe Pro Val Asn Ser Asn Ser Asn Gly
1               5                   10                  15

Gly Asn Glu Leu Cys Pro Lys Ile Arg Ile Gly Gln Asp Asp Leu Pro
            20                  25                  30

Gly Phe Asp Leu Ile Ser Gln Phe Gln Val Asp Lys Ala Ala Ser Arg
        35                  40                  45

Arg Ala Ile Gln Arg Val Val Gly Ser Ala Thr Leu Gln Val Ala Tyr
    50                  55                  60

Lys Leu Gly Asn Asn Val Asp Phe Arg Ile Pro Thr Arg Asn Leu Tyr
65                  70                  75                  80

Pro Ser Gly Leu Pro Glu Glu Tyr Ser Phe Leu Thr Thr Phe Arg Met
```

```
                85                  90                  95
Thr Gly Ser Thr Leu Lys Lys Asn Trp Asn Ile Trp Gln Ile Gln Asp
            100                 105                 110
Ser Ser Gly Lys Glu Gln Val Gly Ile Lys Ile Asn Gly Gln Thr Gln
        115                 120                 125
Ser Val Val Phe Ser Tyr Lys Gly Leu Asp Gly Ser Leu Gln Thr Ala
    130                 135                 140
Ala Phe Ser Asn Leu Ser Ser Leu Phe Asp Ser Gln Trp His Lys Ile
145                 150                 155                 160
Met Ile Gly Val Glu Arg Ser Ser Ala Thr Leu Phe Val Asp Cys Asn
                165                 170                 175
Arg Ile Glu Ser Leu Pro Ile Lys Pro Arg Gly Pro Ile Asp Ile Asp
            180                 185                 190
Gly Phe Ala Val Leu Gly Lys Leu Ala Asp Asn Pro Gln Val Ser Val
        195                 200                 205
Pro Phe Glu Leu Gln Trp Met Leu Ile His Cys Asp Pro Leu Arg Pro
    210                 215                 220
Arg Arg Glu Thr Cys His Glu Leu Pro Ala Arg Ile Thr Pro Ser Gln
225                 230                 235                 240
Thr Thr Asp Glu Arg
                245

<210> SEQ ID NO 2
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Phe Pro Val Asn Ser Asn Ser Asn Gly Gly Asn Glu Leu Cys Pro
1               5                   10                  15
Lys Ile Arg Ile Gly Gln Asp Asp Leu Pro Gly Phe Asp Leu Ile Ser
                20                  25                  30
Gln Phe Gln Val Asp Lys Ala Ala Ser Arg Arg Ala Ile Gln Arg Val
            35                  40                  45
Val Gly Ser Ala Thr Leu Gln Val Ala Tyr Lys Leu Gly Asn Asn Val
        50                  55                  60
Asp Phe Arg Ile Pro Thr Arg Asn Leu Tyr Pro Ser Gly Leu Pro Glu
65                  70                  75                  80
Glu Tyr Ser Phe Leu Thr Thr Phe Arg Met Thr Gly Ser Thr Leu Lys
                85                  90                  95
Lys Asn Trp Asn Ile Trp Gln Ile Gln Asp Ser Ser Gly Lys Glu Gln
                100                 105                 110
Val Gly Ile Lys Ile Asn Gly Gln Thr Gln Ser Val Val Phe Ser Tyr
            115                 120                 125
Lys Gly Leu Asp Gly Ser Leu Gln Thr Ala Ala Phe Ser Asn Leu Ser
        130                 135                 140
Ser Leu Phe Asp Ser Gln Trp His Lys Ile Met Ile Gly Val Glu Arg
145                 150                 155                 160
Ser Ser Ala Thr Leu Phe Val Asp Cys Asn Arg Ile Glu Ser Leu Pro
                165                 170                 175
Ile Lys Pro Arg Gly Pro Ile Asp Ile Asp Gly Phe Ala Val Leu Gly
            180                 185                 190
```

```
Lys Leu Ala Asp Asn Pro Gln Val Ser Val Pro Phe Glu Leu Gln Trp
        195                 200                 205

Met Leu Ile His Cys Asp Pro Leu Arg Pro
    210                 215

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 3

Lys Gln Ser Val Ser Val Ala Glu Phe Ser Tyr Lys Gly
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 4

Lys Ile Leu Met Ile Gly Ser Val Glu Arg Thr Ser Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 5

Lys Leu Gly Asn Asn Val Asp Phe Arg Ile
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 6

Arg Lys Ile Val Glu Ser Thr Leu Pro Asn Ile Lys Pro Arg Lys Gly
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 7

Lys His Asn Tyr Trp Ser Asn Thr Ile Trp Gln Ile Gln Asp Ser Ala
1               5                   10                  15

Gly Lys Arg
```

```
<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 8

Lys Gln Ser Val Ser Val Phe Ser Tyr Lys Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 9

Lys Ile Met Ile Gly Val Glu Arg Thr Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 10

Arg Ile Glu Ser Leu Pro Ile Lys Pro Arg Gly
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 11

Lys His Asn Trp Ser Asn Ile Trp Gln Ile Gln Asp Ser Gly Lys
1               5                   10                  15

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 12

Arg Ile Gly Gln Asp Asp Leu Pro Gly Phe Asp Leu Ile Ser Gln Phe
1               5                   10                  15

Gln Ile Val Asp Lys Ala
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
```

NC4 conserved sequence

<400> SEQUENCE: 13

Arg His Asn Leu Tyr Pro Asn Ser Gly Leu Pro Glu Glu Tyr Ser Phe
1               5                   10                  15

Leu Thr Thr Phe Arg
            20

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 14

Phe Ser Asn Leu Pro Ser Ser Leu Phe Asp Ser Gln Trp His Lys Ile
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 15

Arg Ser Ser Ala Thr Leu Phe Val Asp Cys Asn Arg Ile
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 16

Lys Ser Val Ser Phe Ser Tyr Lys Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 17

Lys Ile Met Ile Gly Val Glu Arg Ser
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 18

Lys Leu Gly Asn Asn Val Asp Phe Arg Ile
1               5                   10

```
<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 19

Arg Ile Glu Ser Leu Pro Ile Lys Pro Arg Gly
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 20

Lys His Trp Ser Ile Trp Gln Ile Gln Asp Ser Ser Gly Lys
1               5                   10

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 21

Arg Ile Gly Gln Asp Asp Leu Pro Gly Phe Asp Leu Ile Ser Gln Phe
1               5                   10                  15

Gln Ile Asp Lys Ala
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 22

Arg His Leu Tyr Pro Asn Gly Leu Pro Glu Glu Tyr Ser Phe Leu Thr
1               5                   10                  15

Thr Phe Arg Met
            20

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 23

Phe Ser Asn Leu Pro Ser Leu Phe Asp Ser Gln Trp His Lys Ile
1               5                   10                  15

<210> SEQ ID NO 24
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      NC4 conserved sequence

<400> SEQUENCE: 24

Arg Ser Ser Ala Thr Leu Phe Val Asp Cys Asn Arg Ile
1               5                   10

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caccatggag aaggccgggg                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gacggacaca ttgggggtat                                                  20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgaagggct acgactggac                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaggaggaat gtggggagtc                                                  20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aggaggtggt actgctggtg                                                  20

<210> SEQ ID NO 30
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tctcactcca gggaactcgt                                                20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agtcaaggga gatcgtggtg                                                20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgtcgtgctg tctcaaggta                                                20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gccctctcca agacatata                                                 19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccatgatcac gtcgatatcc                                                20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acttccgctg gtcagatgga                                                20

<210> SEQ ID NO 36
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctcgtgcca gatcatcacc                                             20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
caacactgcc aacgtccaga t                                           21

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctgcttcgtc cagataggca at                                          22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acacacagct cactcgacct tg                                          22

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggaattctgg ttggtcctct ctt                                         23

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tttgacaaca ggctggtgaa cc                                          22

<210> SEQ ID NO 42
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 42
gtgaaggatc tgcgtctgct tgg					23

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cggcctgttc cccttcttcg tg					22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcgtgtgcta cgctgcggac ca					22

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cacagctgct tatattgttg					20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agtggctgat ttgtctctgc					20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cagcctcctc cagcagttcc					20

<210> SEQ ID NO 48
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 48
taaccgtggc aatgaggaag                                                    20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agctgggaaa atacaagaac c                                                  21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgagctggat ggagaaactg g                                                  21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gagttcgcag cacagcagtt c                                                  21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
caccccagag gatgacacca g                                                  21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccgcctccag tgccctcttc c                                                  21

<210> SEQ ID NO 54
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 54
agcccagccc cagtaacagt g                                              21

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctgttcaggg acagaatgtg ct                                             22

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcgatatgct tcacagttct aggg                                           24

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tcaagttccc cggcgat                                                   17

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgttcaggta ttgcactgcc a                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttttggccat ctcttccttc a                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 60
tgtggatgcc tcttgggtat c                                    21

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgagaaccaa tctcaccgac ag                                   22

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgccacccga gtgtaaccat                                      20

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tcctcttctt gagctggact catt                                 24

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgctctgcaa actggaggtc                                      20

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cagtacgttt ggcaatggag actgc                                25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggtcacattg gaggtgtaga gcttg                                         25

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
catttccgag tctgggccaa                                               20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tggaggcttg agctgagctt                                               20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tgttcagtgc agagccttca                                               20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cttcatactt cggattgacc                                               20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cattcactga tgtggatgtc                                               20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagtgtcttc ttcaccatca                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccgccattaa tgagagtgat                                               20

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agttagttgc ggcaggagaa g                                             21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gataaatcaa cagtgggagc                                               20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cccagatcat ggagtcttta                                               20

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gatccacccc aattccatct gtgc                                          24

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aaccgcgaga atcaaagcca aggcc                                               25

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gaacaggtgc aagctcatct g                                                   21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tctacaacct tgggctgcaa a                                                   21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
caaggtccca tgtgcaacgt                                                     20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
catatgccac caccagtgtc t                                                   21

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tgtcctgcca gcggatgt                                                       18

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84

```
acggaattac tgtacggcct aca                                              23
```

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85

```
tggtatcgtg gaaggactca t                                                21
```

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86

```
gtgggtgtcg ctgttgaagt c                                                21
```

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

```
actctcgaga aaagagctgt caagcgtcgc                                       30
```

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

```
gtcagatctt tatctctcgt cggtggtctg                                       30
```

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89

```
actctcgaga aaagagctgt taagcgtaga ccaagattcc                            40
```

<210> SEQ ID NO 90
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

```
gtcagatctt cattatctct cgtcggtagt ctggcttgga gtaattctgg ctggcagctc      60
```

```
atggcaagtt tctctcctag gtctcagtgg                                          90
```

<210> SEQ ID NO 91
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

```
ctgagatcta ccaggtggac ctcttccatc ggtagtttga c                             41
```

<210> SEQ ID NO 92
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

```
ctgagatctg gtgctggtgc tatgactaag ttacctatac taggttattg g                  51
```

<210> SEQ ID NO 93
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

```
actgtcgact tagtcattaa tgatcagatt ttggaggatg atctccacc                     49
```

<210> SEQ ID NO 94
<211> LENGTH: 268
<212> TYPE: PRT
<213> ORGANISM: Homo sapiens

<400> SEQUENCE: 94

```
Met Lys Thr Cys Trp Lys Ile Pro Val Phe Phe Val Cys Ser Phe
1               5                   10                  15

Leu Glu Pro Trp Ala Ser Ala Ala Val Lys Arg Arg Pro Arg Phe Pro
                20                  25                  30

Val Asn Ser Asn Ser Asn Gly Gly Asn Glu Leu Cys Pro Lys Ile Arg
            35                  40                  45

Ile Gly Gln Asp Asp Leu Pro Gly Phe Asp Leu Ile Ser Gln Phe Gln
        50                  55                  60

Val Asp Lys Ala Ala Ser Arg Arg Ala Ile Gln Arg Val Val Gly Ser
65                  70                  75                  80

Ala Thr Leu Gln Val Ala Tyr Lys Leu Gly Asn Asn Val Asp Phe Arg
                85                  90                  95

Ile Pro Thr Arg Asn Leu Tyr Pro Ser Gly Leu Pro Glu Glu Tyr Ser
            100                 105                 110

Phe Leu Thr Thr Phe Arg Met Thr Gly Ser Thr Leu Lys Lys Asn Trp
        115                 120                 125

Asn Ile Trp Gln Ile Gln Asp Ser Ser Gly Lys Glu Gln Val Gly Ile
    130                 135                 140

Lys Ile Asn Gly Gln Thr Gln Ser Val Val Phe Ser Tyr Lys Gly Leu
145                 150                 155                 160
```

```
Asp Gly Ser Leu Gln Thr Ala Ala Phe Ser Asn Leu Ser Ser Leu Phe
                165                 170                 175

Asp Ser Gln Trp His Lys Ile Met Ile Gly Val Glu Arg Ser Ser Ala
            180                 185                 190

Thr Leu Phe Val Asp Cys Asn Arg Ile Glu Ser Leu Pro Ile Lys Pro
        195                 200                 205

Arg Gly Pro Ile Asp Ile Asp Gly Phe Ala Val Leu Gly Lys Leu Ala
    210                 215                 220

Asp Asn Pro Gln Val Ser Val Pro Phe Glu Leu Gln Trp Met Leu Ile
225                 230                 235                 240

His Cys Asp Pro Leu Arg Pro Arg Glu Thr Cys His Glu Leu Pro
                245                 250                 255

Ala Arg Ile Thr Pro Ser Gln Thr Thr Asp Glu Arg
                260                 265

<210> SEQ ID NO 95
<211> LENGTH: 11
<212> TYPE: PRT
<213> ORGANISM: Homo sapiens

<400> SEQUENCE: 95

Pro Arg Phe Pro Val Asn Ser Asn Ser Asn Gly
1               5                   10

<210> SEQ ID NO 96
<211> LENGTH: 6
<212> TYPE: PRT
<213> ORGANISM: Homo sapiens

<400> SEQUENCE: 96

Asn Glu Leu Cys Pro Lys
1               5

<210> SEQ ID NO 97
<211> LENGTH: 17
<212> TYPE: PRT
<213> ORGANISM: Homo sapiens

<400> SEQUENCE: 97

Arg Ile Gly Gln Asp Asp Leu Pro Gly Phe Asp Leu Ile Ser Gln Phe
1               5                   10                  15

Gln

<210> SEQ ID NO 98
<211> LENGTH: 15
<212> TYPE: PRT
<213> ORGANISM: Homo sapiens

<400> SEQUENCE: 98

Asp Lys Ala Ala Ser Arg Arg Ala Ile Gln Arg Val Val Gly Ser
1               5                   10                  15

<210> SEQ ID NO 99
<211> LENGTH: 14
<212> TYPE: PRT
<213> ORGANISM: Homo sapiens

<400> SEQUENCE: 99

Leu Gln Val Ala Tyr Lys Leu Gly Asn Asn Val Asp Phe Arg
1               5                   10
```

<210> SEQ ID NO 100
<211> LENGTH: 17
<212> TYPE: PRT
<213> ORGANISM: Homo sapiens

<400> SEQUENCE: 100

Pro Glu Glu Tyr Ser Phe Leu Thr Thr Phe Arg Met Thr Gly Ser Thr
1               5                   10                  15
Leu

<210> SEQ ID NO 101
<211> LENGTH: 21
<212> TYPE: PRT
<213> ORGANISM: Homo sapiens

<400> SEQUENCE: 101

Ile Trp Gln Ile Gln Asp Ser Ser Gly Lys Glu Gln Val Gly Ile Lys
1               5                   10                  15
Ile Asn Gly Gln Thr
            20

<210> SEQ ID NO 102
<211> LENGTH: 18
<212> TYPE: PRT
<213> ORGANISM: Homo sapiens

<400> SEQUENCE: 102

Phe Ser Tyr Lys Gly Leu Asp Gly Ser Leu Gln Thr Ala Ala Phe Ser
1               5                   10                  15
Asn Leu

<210> SEQ ID NO 103
<211> LENGTH: 35
<212> TYPE: PRT
<213> ORGANISM: Homo sapiens

<400> SEQUENCE: 103

Ser Leu Phe Asp Ser Gln Trp His Lys Ile Met Ile Gly Val Glu Arg
1               5                   10                  15
Ser Ser Ala Thr Leu Phe Val Asp Cys Asn Arg Ile Glu Ser Leu Pro
            20                  25                  30
Ile Lys Pro
        35

The invention claimed is:

1. A method for treating a disease of the musculoskeletal system or inducing matrix neogenesis, the method comprising administering to a subject in need thereof
   (i) a scaffold comprising pentosan polysulfate (PPS) or a pharmaceutically acceptable salt thereof; and
   (ii) a composition comprising mesenchymal progenitor cells.

2. The method of claim 1, wherein the PPS or pharmaceutically acceptable salt thereof is immobilized on the scaffold.

3. The method of claim 1, wherein the scaffold is a gel scaffold.

4. The method of claim 1, wherein the scaffold is a collagen sponge.

5. The method of claim 1, wherein the mesenchymal progenitor cell is a Stro 1$^{bri}$ cell, and/or a Stro 1$^{bri}$ progeny cell.

6. The method of claim 1, wherein following administration of the (i) scaffold comprising PPS or a pharmaceutically acceptable salt thereof and the (ii) composition comprising mesenchymal progenitor cells, the concentration of the PPS or pharmaceutically acceptable salt thereof is
   about 500 ng/ml/million cells to about 10 mg/ml/million cells.

7. The method of claim 1, wherein the composition comprising mesenchymal progenitor cells further comprises hyaluronic acid.

8. The method of claim 1, wherein the disease of the musculoskeletal system is intervertebral disc degeneration, rheumatoid arthritis or osteoarthritis.

9. The method of claim 1, wherein the disease of the musculoskeletal system is intervertebral disc degeneration.

10. The method of claim 1, wherein contact of the mesenchymal progenitor cells with PPS or a pharmaceutically acceptable salt thereof following administration up regulates chondrogenesis and/or down regulates osteogenesis by the progenitor cells.

11. The method of claim 1, wherein following administration of the (i) scaffold comprising PPS or a pharmaceutically acceptable salt thereof and the (ii) composition comprising mesenchymal progenitor cells, the concentration of the PPS or pharmaceutically acceptable salt thereof is about 500 ng/ml/million cells to about 2000 µg/ml/million cells.

12. The method of claim 1, wherein following administration of the (i) scaffold comprising PPS or a pharmaceutically acceptable salt thereof and the (ii) composition comprising mesenchymal progenitor cells, the concentration of the PPS or pharmaceutically acceptable salt thereof is about 1 µg/ml/million cells to about 1000 µg/ml/million cells.

13. The method of claim 1, wherein the method is for inducing intervertebral disc regeneration.

* * * * *